US012714445B2

(12) United States Patent
Spitler

(10) Patent No.: US 12,714,445 B2
(45) Date of Patent: Aug. 25, 2026

(54) APPARATUS, SYSTEM, AND METHOD FOR PATIENT-SPECIFIC METHODS AND INSTRUMENTATION

(71) Applicant: Treace Medical Concepts, Inc., Ponte Vedra, FL (US)

(72) Inventor: James Q. Spitler, Winter Garden, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 352 days.

(21) Appl. No.: 18/320,768

(22) Filed: May 19, 2023

(65) Prior Publication Data

US 2023/0371966 A1 Nov. 23, 2023

Related U.S. Application Data

(60) Provisional application No. 63/365,126, filed on May 20, 2022.

(51) Int. Cl.
*A61B 17/17* (2006.01)
*A61B 17/064* (2006.01)
(Continued)

(52) U.S. Cl.
CPC ...... *A61B 17/1775* (2016.11); *A61B 17/0644* (2013.01); *A61B 17/064* (2013.01);
(Continued)

(58) Field of Classification Search
CPC ....... A61B 17/17; A61B 17/15; A61B 17/151; A61B 17/152; A61B 17/1775;
(Continued)

(56) References Cited

U.S. PATENT DOCUMENTS

| | | |
|---|---|---|
| 3,664,022 A | 5/1972 | Small |
| 4,069,824 A | 1/1978 | Weinstock |

(Continued)

FOREIGN PATENT DOCUMENTS

| | | |
|---|---|---|
| AU | 2009227957 B2 | 7/2014 |
| AU | 2009222469 B2 | 2/2015 |

(Continued)

OTHER PUBLICATIONS

Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.

(Continued)

*Primary Examiner* — Marcela I. Shirsat
(74) *Attorney, Agent, or Firm* — Fredrikson & Byron, P.A.

(57) ABSTRACT

An apparatus, system, and method is disclosed for correcting a condition present in a patient. In some implementations, the apparatus may include a proximal end. In addition, the apparatus may include a distal end. The apparatus may include a body having a superior side, an inferior side, a medial side, a lateral side, a proximal side, and a distal side. Moreover, the apparatus may include a marker configured to identify a location for a reference feature that corresponds to a model reference for a bone of the patient's foot. Also, the apparatus may include a bone engagement surface configured to register to an anatomical structure of the bone, the bone engagement surface defined based on medical imaging taken of the bone.

15 Claims, 17 Drawing Sheets

(51) Int. Cl.
*A61B 17/15* (2006.01)
*A61B 17/56* (2006.01)
*A61B 17/80* (2006.01)
*A61B 17/88* (2006.01)
*A61B 90/00* (2016.01)

(52) U.S. Cl.
CPC ....... *A61B 17/0642* (2013.01); *A61B 17/0643* (2013.01); *A61B 2017/0645* (2013.01); *A61B 2017/0646* (2013.01); *A61B 17/151* (2013.01); *A61B 17/152* (2013.01); *A61B 17/1728* (2013.01); *A61B 17/1732* (2013.01); *A61B 17/1735* (2013.01); *A61B 2017/565* (2013.01); *A61B 2017/568* (2013.01); *A61B 17/8061* (2013.01); *A61B 17/88* (2013.01); *A61B 17/8866* (2013.01); *A61B 2090/3916* (2016.02); *A61B 2090/3991* (2016.02)

(58) Field of Classification Search
CPC ............ A61B 17/1714; A61B 17/1717; A61B 17/1728; A61B 17/1732; A61B 17/1735; A61B 17/064; A61B 17/0642; A61B 17/0643; A61B 17/0644; A61B 17/80; A61B 17/8061; A61B 17/8866; A61B 17/88; A61B 2017/568; A61B 2017/565; A61B 2017/0645; A61B 2017/0646; A61B 2090/3916; A61B 2090/3991
USPC .......................................................... 606/87
See application file for complete search history.

(56) References Cited

U.S. PATENT DOCUMENTS 4,159,716 A 7/1979 Borchers
4,187,840 A 2/1980 Watanabe
4,335,715 A 6/1982 Kirkley
4,338,927 A 7/1982 Volkov et al.
4,349,018 A 9/1982 Chambers
4,409,973 A 10/1983 Neufeld
4,436,684 A 3/1984 White
4,440,168 A 4/1984 Warren
4,501,268 A 2/1985 Comparetto
4,502,474 A 3/1985 Comparetto
4,509,511 A 4/1985 Neufeld
4,565,191 A 1/1986 Slocum
4,570,624 A 2/1986 Wu
4,627,425 A 12/1986 Reese
4,628,919 A 12/1986 Clyburn
4,632,102 A 12/1986 Comparetto
4,664,102 A 5/1987 Comparetto
4,708,133 A 11/1987 Comparetto
4,736,737 A 4/1988 Fargie et al.
4,750,481 A 6/1988 Reese
4,754,746 A 7/1988 Cox
4,757,810 A 7/1988 Reese
4,839,822 A 6/1989 Dormond et al.
4,895,141 A 1/1990 Koeneman et al.
4,952,214 A 8/1990 Comparetto
4,959,066 A 9/1990 Dunn et al.
4,978,347 A 12/1990 Ilizarov
4,988,349 A 1/1991 Pennig
4,995,875 A 2/1991 Coes
5,021,056 A 6/1991 Hofmann et al.
5,035,698 A 7/1991 Comparetto
5,042,983 A 8/1991 Rayhack
5,049,149 A 9/1991 Schmidt
5,053,039 A 10/1991 Hofmann et al.
5,078,719 A 1/1992 Schreiber
5,112,334 A 5/1992 Alchermes et al.
5,147,364 A 9/1992 Comparetto
5,176,685 A 1/1993 Rayhack
5,207,676 A 5/1993 Canadell et al.
5,246,444 A 9/1993 Schreiber
5,254,119 A 10/1993 Schreiber
5,312,412 A 5/1994 Whipple
5,358,504 A 10/1994 Paley et al.
5,364,402 A 11/1994 Mumme et al.
5,374,271 A 12/1994 Hwang
5,413,579 A 5/1995 Tom
5,417,694 A 5/1995 Marik et al.
5,449,360 A 9/1995 Schreiber
5,470,335 A 11/1995 Du
5,490,854 A 2/1996 Fisher et al.
5,529,075 A 6/1996 Clark
5,540,695 A 7/1996 Levy
5,578,038 A 11/1996 Slocum
5,586,564 A 12/1996 Barrett et al.
5,601,565 A 2/1997 Huebner
5,613,969 A 3/1997 Jenkins
5,620,442 A 4/1997 Bailey et al.
5,620,448 A 4/1997 Puddu
5,643,270 A 7/1997 Combs
5,667,510 A 9/1997 Combs
H1706 H 1/1998 Mason
5,722,978 A 3/1998 Jenkins
5,749,875 A 5/1998 Puddu
5,779,709 A 7/1998 Harris et al.
5,788,695 A 8/1998 Richardson
5,803,924 A 9/1998 Oni et al.
5,810,822 A 9/1998 Mortier
5,839,438 A 11/1998 Graettinger et al.
5,843,085 A 12/1998 Graser
5,893,553 A 4/1999 Pinkous
5,911,724 A 6/1999 Wehrli
5,935,128 A 8/1999 Carter et al.
5,941,877 A 8/1999 Megas et al.
5,951,556 A 9/1999 Faccioli et al.
5,957,927 A 9/1999 Magee et al.
5,980,526 A 11/1999 Johnson et al.
5,984,931 A 11/1999 Greenfield
6,007,535 A 12/1999 Rayhack et al.
6,027,504 A 2/2000 McGuire
6,030,391 A 2/2000 Brainard et al.
6,162,223 A 12/2000 Orsak et al.
6,171,309 B1 1/2001 Huebner
6,203,545 B1 3/2001 Stoffella
6,248,109 B1 6/2001 Stoffella
6,391,031 B1 5/2002 Toomey
6,416,465 B2 7/2002 Brau
6,478,799 B1 11/2002 Williamson
6,511,481 B2 1/2003 Von et al.
6,547,793 B1 4/2003 McGuire
6,676,662 B1 1/2004 Bagga et al.
6,719,773 B1 4/2004 Boucher et al.
6,743,233 B1 6/2004 Baldwin et al.
6,755,838 B2 6/2004 Trnka
6,796,986 B2 9/2004 Duffner
6,859,661 B2 2/2005 Tuke
6,944,518 B2 9/2005 Roose
6,964,645 B1 11/2005 Smits
7,018,383 B2 3/2006 McGuire
7,033,361 B2 4/2006 Collazo
7,097,647 B2 8/2006 Segler
7,112,204 B2 9/2006 Justin et al.
7,153,310 B2 12/2006 Ralph et al.
7,182,766 B1 2/2007 Mogul
7,241,298 B2 7/2007 Nemec et al.
7,282,054 B2 10/2007 Steffensmeier et al.
7,351,203 B2 4/2008 Jelliffe et al.
7,377,924 B2 5/2008 Raistrick et al.
7,465,303 B2 12/2008 Riccione et al.
7,540,874 B2 6/2009 Trumble et al.
7,572,258 B2 8/2009 Stiernborg
7,618,451 B2 11/2009 Fitz et al.
7,641,660 B2 1/2010 Lakin et al.
D610,257 S 2/2010 Horton
7,686,811 B2 3/2010 Byrd et al.
7,691,108 B2 4/2010 Lavallee
7,763,026 B2 7/2010 Egger et al.
D629,900 S 12/2010 Fisher
7,967,823 B2 6/2011 Ammann et al.
7,972,338 B2 7/2011 Obrien

(56) References Cited

U.S. PATENT DOCUMENTS

D646,389 S 10/2011 Claypool et al.
8,057,478 B2 11/2011 Kuczynski et al.
8,062,301 B2 11/2011 Ammann et al.
D651,315 S 12/2011 Bertoni et al.
D651,316 S 12/2011 May et al.
8,080,010 B2 12/2011 Schulz et al.
8,080,045 B2 12/2011 Wotton
8,083,745 B2 12/2011 Lang et al.
8,083,746 B2 12/2011 Novak
8,105,330 B2 1/2012 Fitz et al.
8,123,753 B2 2/2012 Poncet
8,137,406 B2 3/2012 Novak et al.
8,147,530 B2 4/2012 Strnad et al.
8,160,345 B2 4/2012 Pavlovskaia et al.
8,167,918 B2 5/2012 Strnad et al.
8,172,848 B2 5/2012 Tomko et al.
8,192,441 B2 6/2012 Collazo
8,197,487 B2 6/2012 Poncet et al.
8,231,623 B1 7/2012 Jordan
8,231,663 B2 7/2012 Kay et al.
8,236,000 B2 8/2012 Ammann et al.
8,246,561 B1 8/2012 Agee et al.
8,246,680 B2 8/2012 Betz et al.
D666,721 S 9/2012 Wright et al.
8,262,664 B2 9/2012 Justin et al.
8,277,459 B2 10/2012 Sand et al.
8,282,644 B2 10/2012 Edwards
8,282,645 B2 10/2012 Lawrence et al.
8,287,541 B2 10/2012 Nelson et al.
8,292,966 B2 10/2012 Morton
8,298,237 B2 10/2012 Schoenefeld et al.
8,303,596 B2 11/2012 Plabetaky et al.
8,313,492 B2 11/2012 Wong et al.
8,323,288 B2 12/2012 Zajac
8,323,289 B2 12/2012 Re
8,337,501 B2 12/2012 Fitz et al.
8,337,503 B2 12/2012 Lian
8,343,159 B2 1/2013 Bennett
8,366,771 B2 2/2013 Burdulis et al.
8,377,105 B2 2/2013 Buescher
D679,395 S 4/2013 Wright et al.
8,409,209 B2 4/2013 Ammann et al.
8,435,246 B2 5/2013 Fisher et al.
8,475,462 B2 7/2013 Thomas et al.
8,475,463 B2 7/2013 Lian
8,484,001 B2 7/2013 Glozman et al.
8,496,662 B2 7/2013 Novak et al.
8,518,045 B2 8/2013 Szanto
8,523,870 B2 9/2013 Green et al.
8,529,571 B2 9/2013 Horan et al.
8,540,777 B2 9/2013 Ammann et al.
8,545,508 B2 10/2013 Collazo
8,551,102 B2 10/2013 Fitz et al.
8,556,906 B2 10/2013 Steines et al.
8,561,278 B2 10/2013 Fitz et al.
8,585,708 B2 11/2013 Fitz et al.
D694,884 S 12/2013 Mooradian et al.
D695,402 S 12/2013 Dacosta et al.
8,634,617 B2 1/2014 Tsougarakis et al.
8,652,142 B2 2/2014 Geissler
8,657,820 B2 2/2014 Kubiak et al.
8,657,827 B2 2/2014 Fitz et al.
D701,303 S 3/2014 Cook
8,672,945 B2 3/2014 Lavallee et al.
8,682,052 B2 3/2014 Fitz et al.
8,696,716 B2 4/2014 Kartalian et al.
8,702,686 B2 4/2014 Geebelen et al.
8,702,715 B2 4/2014 Ammann et al.
D705,929 S 5/2014 Frey
8,715,363 B2 5/2014 Ratron et al.
8,728,084 B2 5/2014 Berelsman et al.
8,758,354 B2 6/2014 Habegger et al.
8,764,760 B2 7/2014 Metzger et al.
8,764,763 B2 7/2014 Wong et al.
8,768,028 B2 7/2014 Lang et al.
8,771,279 B2 7/2014 Philippon et al.
8,777,948 B2 7/2014 Bernsteiner
8,784,427 B2 7/2014 Fallin et al.
8,784,457 B2 7/2014 Graham
8,795,286 B2 8/2014 Sand et al.
8,801,719 B2 8/2014 Park et al.
8,801,727 B2 8/2014 Chan et al.
8,808,301 B1 8/2014 Nofsinger
8,808,303 B2 8/2014 Stemniski et al.
8,821,499 B2 9/2014 Iannotti et al.
8,828,012 B2 9/2014 May et al.
8,828,063 B2 9/2014 Blitz et al.
8,838,263 B2 9/2014 Sivak et al.
8,858,602 B2 10/2014 Weiner et al.
8,882,778 B2 11/2014 Ranft
8,882,816 B2 11/2014 Kartalian et al.
8,888,785 B2 11/2014 Ammann et al.
D720,456 S 12/2014 Dacosta et al.
8,900,247 B2 12/2014 Tseng et al.
8,906,026 B2 12/2014 Ammann et al.
8,945,132 B2 2/2015 Plaby et al.
8,965,088 B2 2/2015 Tsougarakis et al.
8,983,813 B2 3/2015 Miles et al.
8,998,903 B2 4/2015 Price et al.
8,998,904 B2 4/2015 Zeetser et al.
9,011,452 B2 4/2015 Iannotti et al.
9,014,835 B2 4/2015 Azernikov et al.
9,017,336 B2 4/2015 Park et al.
9,023,052 B2 5/2015 Lietz et al.
9,044,250 B2 6/2015 Olsen et al.
9,055,953 B2 6/2015 Lang et al.
9,060,822 B2 6/2015 Lewis et al.
9,066,727 B2 6/2015 Catanzarite et al.
9,089,376 B2 7/2015 Medoff et al.
9,095,353 B2 8/2015 Burdulis et al.
9,101,421 B2 8/2015 Blacklidge
9,107,715 B2 8/2015 Blitz et al.
9,113,920 B2 8/2015 Ammann et al.
9,131,945 B2 9/2015 Aram et al.
D740,424 S 10/2015 Dacosta et al.
9,186,154 B2 11/2015 Li
9,198,678 B2 12/2015 Frey et al.
9,216,025 B2 12/2015 Fitz et al.
9,220,509 B2 12/2015 Lavallee et al.
9,289,221 B2 3/2016 Gelaude et al.
9,351,744 B2 5/2016 Kunz et al.
9,358,019 B2 6/2016 Gibson et al.
9,361,410 B2 6/2016 Davison et al.
9,402,636 B2 8/2016 Collazo
9,402,640 B2 8/2016 Reynolds et al.
9,411,939 B2 8/2016 Furrer et al.
9,414,847 B2 8/2016 Kurtz
D765,844 S 9/2016 Dacosta
D766,434 S 9/2016 Dacosta
D766,437 S 9/2016 Dacosta
D766,438 S 9/2016 Dacosta
D766,439 S 9/2016 Dacosta
9,433,452 B2 9/2016 Weiner et al.
9,439,767 B2 9/2016 Bojarski et al.
9,452,050 B2 9/2016 Miles et al.
9,452,057 B2 9/2016 Dacosta et al.
9,456,902 B2 10/2016 Hacking et al.
9,492,182 B2 11/2016 Keefer
9,495,483 B2 11/2016 Steines et al.
9,498,234 B2 11/2016 Goldstein et al.
9,522,023 B2 12/2016 Haddad et al.
9,579,110 B2 2/2017 Bojarski et al.
9,579,112 B2 2/2017 Catanzarite et al.
9,592,084 B2 3/2017 Grant
9,615,834 B2 4/2017 Agnihotri et al.
9,622,805 B2 4/2017 Santrock et al.
9,622,820 B2 4/2017 Baloch et al.
9,652,889 B2 5/2017 Young et al.
9,662,127 B2 5/2017 Meridew et al.
9,668,747 B2 6/2017 Metzger et al.
9,687,250 B2 6/2017 Dayton et al.
9,687,259 B2 6/2017 Pavlovskaia et al.
9,707,044 B2 7/2017 Davison et al.
9,717,508 B2 8/2017 Iannotti et al.

(56) References Cited

U.S. PATENT DOCUMENTS 9,737,367 B2 8/2017 Steines et al.
9,743,935 B2 8/2017 Smith et al.
9,750,538 B2 9/2017 Soffiatti et al.
9,785,747 B2 10/2017 Geebelen
9,786,022 B2 10/2017 Aram et al.
9,795,394 B2 10/2017 Bonutti
9,814,474 B2 11/2017 Montoya et al.
9,872,773 B2 1/2018 Lang et al.
9,888,931 B2 2/2018 Bake
9,907,561 B2 3/2018 Luna et al.
9,918,769 B2 3/2018 Provencher et al.
9,924,950 B2 3/2018 Couture et al.
9,925,068 B2 3/2018 Bays et al.
9,980,760 B2 5/2018 Dacosta et al.
9,993,256 B2 6/2018 Lipman et al.
10,002,227 B2 6/2018 Netravali et al.
10,010,431 B2 7/2018 Eraly et al.
10,022,170 B2 7/2018 Leemrijse et al.
10,028,750 B2 7/2018 Rose
10,045,807 B2 8/2018 Santrock et al.
10,052,114 B2 8/2018 Keppler et al.
10,055,536 B2 8/2018 Maes et al.
10,064,631 B2 9/2018 Dacosta et al.
10,089,413 B2 10/2018 Wirx-Speetjens et al.
10,123,807 B2 11/2018 Geebelen
10,149,722 B2 12/2018 Aram et al.
10,159,499 B2 12/2018 Dacosta et al.
10,182,832 B1 1/2019 Saltzman et al.
10,201,357 B2 2/2019 Aram et al.
10,206,692 B2 2/2019 Sanders
10,231,745 B2 3/2019 Geebelen et al.
10,262,084 B2 4/2019 Lavallee et al.
10,265,080 B2 4/2019 Hughes et al.
10,282,488 B2 5/2019 Eash
10,292,713 B2 5/2019 Fallin et al.
10,327,785 B2 6/2019 Bake et al.
10,327,829 B2 6/2019 Dacosta et al.
10,342,590 B2 7/2019 Bays et al.
10,357,261 B2 7/2019 Kugler et al.
10,363,052 B2 7/2019 Park et al.
10,376,268 B2 8/2019 Fallin et al.
10,398,510 B2 9/2019 Goto
10,467,356 B2 11/2019 Davison et al.
10,470,779 B2 11/2019 Fallin et al.
10,512,470 B1 12/2019 Bays et al.
10,524,808 B1 1/2020 Hissong et al.
10,548,668 B2 2/2020 Furrer et al.
10,561,426 B1 2/2020 Dayton et al.
10,575,862 B2 3/2020 Bays et al.
10,603,046 B2 3/2020 Dayton et al.
10,610,241 B2 4/2020 Wagner et al.
10,675,063 B2 6/2020 Pavlovskaia et al.
10,687,856 B2 6/2020 Park et al.
10,779,867 B2 9/2020 Penzimer et al.
10,779,890 B2 9/2020 Weir
10,786,291 B2 9/2020 Weiner et al.
10,828,046 B2 11/2020 Rose et al.
10,849,631 B2 12/2020 Hatch et al.
10,849,665 B2 12/2020 Singh et al.
10,849,670 B2 12/2020 Santrock et al.
10,856,886 B2 12/2020 Dacosta et al.
10,856,925 B1 12/2020 Pontell
10,881,416 B2 1/2021 Couture et al.
10,881,417 B2 1/2021 Mahfouz
10,888,335 B2 1/2021 Dayton et al.
10,888,340 B2 1/2021 Awtrey et al.
10,898,211 B2 1/2021 Fallin et al.
10,912,571 B2 2/2021 Pavlovskaia et al.
10,939,922 B2 3/2021 Dhillon
10,939,939 B1 3/2021 Gil et al.
10,973,529 B2 4/2021 Lavallee et al.
10,987,176 B2 4/2021 Poltaretskyi et al.
11,000,327 B2 5/2021 Schlotterback et al.
11,033,333 B2 6/2021 Singh et al.
11,058,546 B2 7/2021 Hollis et al.
11,065,011 B2 7/2021 Bake et al.
11,074,688 B2 7/2021 Chabin et al.
11,090,069 B2 8/2021 Park
11,116,518 B2 9/2021 Hafez et al.
11,129,678 B2 9/2021 Park
11,147,568 B2 10/2021 Fitz et al.
11,154,362 B2 10/2021 Kim et al.
11,172,945 B1 11/2021 Lian
11,213,305 B2 1/2022 Iannotti et al.
11,213,406 B2 1/2022 Rodriguez et al.
11,219,526 B2 1/2022 Mahfouz
11,224,448 B2 1/2022 Bailey
11,259,817 B2 3/2022 Fallin et al.
11,278,337 B2 3/2022 Bays et al.
11,278,413 B1 3/2022 Lang
11,304,705 B2 4/2022 Fallin et al.
11,426,184 B2 8/2022 Rivet-Sabourin et al.
11,497,557 B2 11/2022 Haslam et al.
11,633,197 B2 4/2023 Denham et al.
2002/0099381 A1 7/2002 Maroney
2002/0107519 A1 8/2002 Dixon et al.
2002/0165552 A1 11/2002 Duffner
2002/0198531 A1 12/2002 Millard et al.
2004/0010259 A1 1/2004 Keller et al.
2004/0039394 A1 2/2004 Conti et al.
2004/0097946 A1 5/2004 Dietzel et al.
2004/0138669 A1 7/2004 Horn
2005/0004676 A1 1/2005 Schon et al.
2005/0059978 A1 3/2005 Sherry et al.
2005/0070909 A1 3/2005 Egger et al.
2005/0075641 A1 4/2005 Singhatat et al.
2005/0101961 A1 5/2005 Huebner et al.
2005/0149042 A1 7/2005 Metzger
2005/0228389 A1 10/2005 Stiernborg
2005/0251147 A1 11/2005 Novak
2005/0267482 A1 12/2005 Hyde
2005/0273112 A1 12/2005 McNamara
2006/0129163 A1 6/2006 McGuire
2006/0206044 A1 9/2006 Simon
2006/0217733 A1 9/2006 Plassky et al.
2006/0229621 A1 10/2006 Cadmus
2006/0241607 A1 10/2006 Myerson et al.
2006/0241608 A1 10/2006 Myerson et al.
2006/0264961 A1 11/2006 Murray-Brown
2007/0010818 A1 1/2007 Stone et al.
2007/0123857 A1 5/2007 Deffenbaugh et al.
2007/0213726 A1 9/2007 McGarity et al.
2007/0233138 A1 10/2007 Figueroa et al.
2007/0265634 A1 11/2007 Weinstein
2007/0276383 A1 11/2007 Rayhack
2008/0009863 A1 1/2008 Bond et al.
2008/0015603 A1 1/2008 Collazo
2008/0039850 A1 2/2008 Rowley et al.
2008/0091197 A1 4/2008 Coughlin
2008/0140081 A1 6/2008 Heavener et al.
2008/0147073 A1 6/2008 Ammann et al.
2008/0172054 A1 7/2008 Claypool et al.
2008/0195215 A1 8/2008 Morton
2008/0208252 A1 8/2008 Holmes
2008/0262500 A1 10/2008 Collazo
2008/0269908 A1 10/2008 Warburton
2008/0288004 A1 11/2008 Schendel
2009/0036893 A1 2/2009 Kartalian et al.
2009/0036931 A1 2/2009 Pech et al.
2009/0054899 A1 2/2009 Ammann et al.
2009/0087276 A1 4/2009 Rose
2009/0088755 A1 4/2009 Aker et al.
2009/0093849 A1 4/2009 Grabowski
2009/0105767 A1 4/2009 Reiley
2009/0118733 A1 5/2009 Orsak et al.
2009/0125114 A1 5/2009 May et al.
2009/0198244 A1 8/2009 Leibel
2009/0198279 A1 8/2009 Zhang et al.
2009/0210010 A1 8/2009 Strnad et al.
2009/0216089 A1 8/2009 Davidson
2009/0222047 A1 9/2009 Graham
2009/0254092 A1 10/2009 Albiol
2009/0254126 A1 10/2009 Orbay et al.
2009/0287309 A1 11/2009 Walch et al.

(56) References Cited

U.S. PATENT DOCUMENTS

2010/0023010 A1 1/2010 Nelson et al.
2010/0069910 A1 3/2010 Hasselman
2010/0121334 A1 5/2010 Couture et al.
2010/0130981 A1 5/2010 Richards
2010/0152782 A1 6/2010 Stone et al.
2010/0168799 A1 7/2010 Schumer
2010/0185245 A1 7/2010 Paul et al.
2010/0217270 A1 8/2010 Polinski et al.
2010/0217338 A1 8/2010 Carroll et al.
2010/0249779 A1 9/2010 Hotchkiss et al.
2010/0256479 A1 10/2010 Park et al.
2010/0256687 A1 10/2010 Neufeld et al.
2010/0274534 A1 10/2010 Steines et al.
2010/0318088 A1 12/2010 Warne et al.
2010/0324556 A1 12/2010 Tyber et al.
2011/0009865 A1 1/2011 Orfaly
2011/0093084 A1 4/2011 Morton
2011/0118739 A1 5/2011 Tyber et al.
2011/0178524 A1 7/2011 Lawrence et al.
2011/0213376 A1 9/2011 Maxson et al.
2011/0245835 A1 10/2011 Dodds et al.
2011/0288550 A1 11/2011 Orbay et al.
2011/0301648 A1 12/2011 Lofthouse et al.
2012/0016426 A1 1/2012 Robinson
2012/0065689 A1 3/2012 Prasad et al.
2012/0078258 A1 3/2012 Lo et al.
2012/0109135 A1 5/2012 Bailey
2012/0123420 A1 5/2012 Honiball
2012/0123484 A1 5/2012 Lietz et al.
2012/0130376 A1 5/2012 Loring et al.
2012/0130382 A1 5/2012 Iannotti et al.
2012/0130383 A1 5/2012 Budoff
2012/0130434 A1 5/2012 Stemniski
2012/0184961 A1 7/2012 Johannaber
2012/0185056 A1 7/2012 Warburton
2012/0191199 A1 7/2012 Raemisch
2012/0239045 A1 9/2012 Li
2012/0253350 A1 10/2012 Anthony et al.
2012/0265301 A1 10/2012 Demers et al.
2012/0277745 A1 11/2012 Lizee
2012/0303033 A1 11/2012 Weiner et al.
2012/0330135 A1 12/2012 Millahn et al.
2013/0012949 A1 1/2013 Fallin et al.
2013/0035694 A1 2/2013 Grimm et al.
2013/0085499 A1 4/2013 Lian
2013/0085502 A1 4/2013 Harrold
2013/0096563 A1 4/2013 Meade et al.
2013/0119579 A1 5/2013 Iannotti et al.
2013/0131821 A1 5/2013 Cachia
2013/0150900 A1 6/2013 Haddad et al.
2013/0150903 A1 6/2013 Vincent
2013/0158556 A1 6/2013 Jones et al.
2013/0165936 A1 6/2013 Myers
2013/0165938 A1 6/2013 Chow et al.
2013/0172942 A1 7/2013 Lewis et al.
2013/0184714 A1 7/2013 Kaneyama et al.
2013/0190765 A1 7/2013 Harris et al.
2013/0190766 A1 7/2013 Harris et al.
2013/0204259 A1 8/2013 Zajac
2013/0226248 A1 8/2013 Hatch et al.
2013/0226252 A1 8/2013 Mayer
2013/0231668 A1 9/2013 Olsen et al.
2013/0236874 A1 9/2013 Iannotti et al.
2013/0237987 A1 9/2013 Graham
2013/0237989 A1 9/2013 Bonutti
2013/0267956 A1 10/2013 Terrill et al.
2013/0292870 A1 11/2013 Roger
2013/0296865 A1 11/2013 Aram et al.
2013/0310836 A1 11/2013 Raub et al.
2013/0325019 A1 12/2013 Thomas et al.
2013/0325076 A1 12/2013 Palmer et al.
2013/0331845 A1 12/2013 Horan et al.
2013/0338785 A1 12/2013 Wong
2014/0005672 A1 1/2014 Edwards et al.
2014/0025127 A1 1/2014 Richter et al.
2014/0039501 A1 2/2014 Schickendantz et al.
2014/0039561 A1 2/2014 Weiner et al.
2014/0046387 A1 2/2014 Waizenegger
2014/0074099 A1 3/2014 Vigneron et al.
2014/0074101 A1 3/2014 Collazo
2014/0094861 A1 4/2014 Fallin
2014/0094924 A1 4/2014 Hacking et al.
2014/0100579 A1 4/2014 Kelman et al.
2014/0135775 A1 5/2014 Maxson et al.
2014/0142710 A1 5/2014 Lang
2014/0163563 A1 6/2014 Reynolds et al.
2014/0163570 A1 6/2014 Reynolds et al.
2014/0171953 A1 6/2014 Gonzalvez et al.
2014/0180342 A1 6/2014 Lowery et al.
2014/0188139 A1 7/2014 Fallin et al.
2014/0194884 A1 7/2014 Martin et al.
2014/0194999 A1 7/2014 Orbay et al.
2014/0207144 A1 7/2014 Lee et al.
2014/0228860 A1 8/2014 Steines et al.
2014/0249537 A1 9/2014 Wong et al.
2014/0257308 A1 9/2014 Johannaber
2014/0257509 A1 9/2014 Dacosta et al.
2014/0276815 A1 9/2014 Riccione
2014/0276853 A1 9/2014 Long et al.
2014/0277176 A1 9/2014 Buchanan et al.
2014/0277214 A1 9/2014 Helenbolt et al.
2014/0288562 A1 9/2014 Von Zabern et al.
2014/0296995 A1 10/2014 Reiley et al.
2014/0303621 A1 10/2014 Gerold et al.
2014/0336658 A1 11/2014 Luna et al.
2014/0343555 A1 11/2014 Russi et al.
2014/0350561 A1 11/2014 Dacosta et al.
2014/0371897 A1 12/2014 Lin et al.
2015/0032168 A1 1/2015 Orsak et al.
2015/0032217 A1 1/2015 Bojarski et al.
2015/0045801 A1 2/2015 Axelson et al.
2015/0045839 A1 2/2015 Dacosta et al.
2015/0051650 A1 2/2015 Verstreken et al.
2015/0057665 A1 2/2015 Neal et al.
2015/0057667 A1 2/2015 Ammann et al.
2015/0066094 A1 3/2015 Prandi et al.
2015/0112446 A1 4/2015 Melamed et al.
2015/0119944 A1 4/2015 Geldwert
2015/0142000 A1 5/2015 Seedhom et al.
2015/0142064 A1 5/2015 Perez et al.
2015/0150608 A1 6/2015 Sammarco
2015/0182273 A1 7/2015 Stemniski et al.
2015/0223851 A1 8/2015 Hill et al.
2015/0230843 A1 8/2015 Palmer et al.
2015/0245858 A1 9/2015 Weiner et al.
2015/0305752 A1 10/2015 Eash
2015/0342756 A1 12/2015 Bays et al.
2015/0351916 A1 12/2015 Kosarek et al.
2016/0015426 A1 1/2016 Dayton
2016/0022315 A1 1/2016 Soffiatti et al.
2016/0030196 A1 2/2016 Eraly et al.
2016/0135858 A1 5/2016 Dacosta et al.
2016/0151165 A1 6/2016 Fallin et al.
2016/0175089 A1 6/2016 Fallin et al.
2016/0192949 A1 7/2016 Robichaud et al.
2016/0192950 A1 7/2016 Dayton et al.
2016/0192951 A1 7/2016 Gelaude et al.
2016/0199076 A1 7/2016 Fallin et al.
2016/0206331 A1 7/2016 Fitz et al.
2016/0206379 A1 7/2016 Flett et al.
2016/0213384 A1 7/2016 Fallin et al.
2016/0235414 A1 8/2016 Hatch et al.
2016/0242791 A1 8/2016 Fallin et al.
2016/0256204 A1 9/2016 Patel et al.
2016/0270855 A1 9/2016 Kunz et al.
2016/0324532 A1 11/2016 Montoya et al.
2016/0324555 A1 11/2016 Brumfield et al.
2016/0331467 A1 11/2016 Slamin et al.
2016/0354127 A1 12/2016 Lundquist et al.
2016/0361071 A1 12/2016 Mahfouz
2017/0000498 A1 1/2017 Grant et al.
2017/0007408 A1 1/2017 Fitz et al.
2017/0014143 A1 1/2017 Dayton et al.
2017/0014173 A1 1/2017 Smith et al.

(56) References Cited

U.S. PATENT DOCUMENTS

2017/0020537 A1 1/2017 Tuten
2017/0027593 A1 2/2017 Bojarski et al.
2017/0042598 A1 2/2017 Santrock et al.
2017/0042599 A1 2/2017 Bays et al.
2017/0056183 A1 3/2017 Steines et al.
2017/0065347 A1 3/2017 Bojarski et al.
2017/0079669 A1 3/2017 Bays et al.
2017/0119531 A1 5/2017 Bojarski et al.
2017/0143511 A1 5/2017 Cachia
2017/0164989 A1 6/2017 Weiner et al.
2017/0164990 A1 6/2017 Weiner et al.
2017/0231645 A1 8/2017 Metzger et al.
2017/0245906 A1 8/2017 Kugler et al.
2017/0245935 A1 8/2017 Kugler et al.
2017/0249440 A1 8/2017 Lang et al.
2017/0290614 A1 10/2017 Weiner et al.
2017/0360578 A1 12/2017 Shin et al.
2018/0021145 A1 1/2018 Seavey et al.
2018/0033338 A1 2/2018 Iannotti et al.
2018/0036019 A1 2/2018 Iannotti et al.
2018/0049758 A1 2/2018 Amis et al.
2018/0085133 A1 3/2018 Lavallee et al.
2018/0110530 A1 4/2018 Wagner et al.
2018/0116804 A1 5/2018 Hafez et al.
2018/0125504 A1 5/2018 Dayton et al.
2018/0132868 A1 5/2018 Dacosta et al.
2018/0146970 A1 5/2018 Luna et al.
2018/0185097 A1 7/2018 Langhorn et al.
2018/0235641 A1 8/2018 Mcauliffe et al.
2018/0235765 A1 8/2018 Welker et al.
2018/0271569 A1 9/2018 Verstreken et al.
2018/0289380 A1 10/2018 Mauldin et al.
2018/0289423 A1 10/2018 Singh et al.
2018/0317986 A1 11/2018 Jackman et al.
2018/0317992 A1 11/2018 Santrock et al.
2018/0344326 A1 12/2018 Chan et al.
2018/0344334 A1 12/2018 Kim et al.
2018/0344409 A1 12/2018 Bonny et al.
2019/0000629 A1 1/2019 Winslow
2019/0008532 A1 1/2019 Fitz et al.
2019/0015113 A1 1/2019 Morvan
2019/0059913 A1 2/2019 Saltzman et al.
2019/0099189 A1 4/2019 Fallin et al.
2019/0117286 A1 4/2019 Tyber et al.
2019/0146458 A1 5/2019 Roh et al.
2019/0175237 A1 6/2019 Treace et al.
2019/0254681 A1 8/2019 Couture et al.
2019/0274745 A1 9/2019 Smith et al.
2019/0282302 A1 9/2019 Park
2019/0307495 A1 10/2019 Geldwert
2019/0328435 A1 10/2019 Bays et al.
2019/0328436 A1 10/2019 Bays et al.
2019/0336140 A1* 11/2019 Dacosta ............. A61B 17/1682
2019/0350602 A1 11/2019 Stemniski et al.
2019/0357919 A1 11/2019 Fallin et al.
2019/0365419 A1 12/2019 Rhodes et al.
2019/0374237 A1 12/2019 Metzger et al.
2019/0388240 A1 12/2019 Courtis et al.
2020/0015856 A1 1/2020 Treace et al.
2020/0015874 A1 1/2020 Hartson et al.
2020/0046374 A1 2/2020 Luttrell et al.
2020/0054351 A1 2/2020 Meridew et al.
2020/0060739 A1 2/2020 Nachtrab et al.
2020/0085452 A1 3/2020 Siegler
2020/0085588 A1 3/2020 Mauldin et al.
2020/0129213 A1 4/2020 Singh et al.
2020/0155176 A1 5/2020 Bays et al.
2020/0188134 A1 6/2020 Mullen et al.
2020/0237386 A1 7/2020 Stemniski et al.
2020/0243199 A1 7/2020 Farley et al.
2020/0246027 A1 8/2020 Robichaud et al.
2020/0253641 A1 8/2020 Treace et al.
2020/0253740 A1 8/2020 Puncreobutr et al.
2020/0258227 A1 8/2020 Liao et al.
2020/0275976 A1 9/2020 Mckinnon et al.
2020/0297495 A1 9/2020 Gemon et al.
2020/0315708 A1 10/2020 Mosnier et al.
2020/0334871 A1 10/2020 Su et al.
2020/0349699 A1 11/2020 Shah
2020/0352580 A1 11/2020 Saltzman et al.
2020/0352582 A1 11/2020 Larche et al.
2020/0356073 A1 11/2020 Tokushima
2020/0367910 A1 11/2020 Hafez et al.
2020/0390452 A1 12/2020 Bojarski et al.
2021/0007760 A1 1/2021 Reisin
2021/0015527 A1 1/2021 Singh et al.
2021/0038212 A1 2/2021 May et al.
2021/0042458 A1 2/2021 Dayal et al.
2021/0059691 A1 3/2021 Zille
2021/0068846 A1 3/2021 Langhorn et al.
2021/0077131 A1 3/2021 Denham et al.
2021/0077192 A1* 3/2021 Perler ..................... G06F 30/10
2021/0090248 A1 3/2021 Choi et al.
2021/0093328 A1 4/2021 Dayton et al.
2021/0093365 A1 4/2021 Dayton et al.
2021/0106372 A1 4/2021 Tyber et al.
2021/0113222 A1 4/2021 Khatibi et al.
2021/0121251 A1 4/2021 Aljuri et al.
2021/0121297 A1 4/2021 Cavanagh et al.
2021/0137613 A1 5/2021 Chi
2021/0145456 A1 5/2021 Dhillon
2021/0145461 A1 5/2021 Mcginley et al.
2021/0145518 A1 5/2021 Mosnier et al.
2021/0153948 A1 5/2021 Stifter et al.
2021/0161543 A1 6/2021 Mcauliffe et al.
2021/0186704 A1 6/2021 Fitz et al.
2021/0196290 A1 7/2021 Iannotti et al.
2021/0205099 A1 7/2021 Parr
2021/0210189 A1 7/2021 Casey et al.
2021/0212705 A1 7/2021 Reynolds et al.
2021/0244477 A1 8/2021 Singh et al.
2021/0251670 A1 8/2021 Sayger et al.
2021/0259713 A1 8/2021 Trabish et al.
2021/0267730 A1 9/2021 Azernikov et al.
2021/0272134 A1 9/2021 Indani et al.
2021/0275196 A1 9/2021 Wodajo
2021/0282790 A1 9/2021 Sellman et al.
2021/0290319 A1 9/2021 Poltaretskyi et al.
2021/0307796 A1 10/2021 Marien et al.
2021/0307833 A1 10/2021 Farley et al.
2021/0315593 A1 10/2021 Mauldin et al.
2021/0322034 A1 10/2021 Athwal et al.
2021/0330311 A1 10/2021 Denham et al.
2021/0330336 A1 10/2021 Courtis et al.
2021/0330339 A1 10/2021 Robichaud et al.
2021/0330468 A1 10/2021 Mimnaugh et al.
2021/0338450 A1 11/2021 Hollis et al.
2021/0346091 A1 11/2021 Haslam et al.
2021/0353304 A1 11/2021 Robichaud et al.
2021/0353312 A1 11/2021 Robichaud et al.
2021/0361297 A1 11/2021 Luna et al.
2021/0361300 A1 11/2021 Mcginley et al.
2021/0361330 A1 11/2021 Mcaleer et al.
2021/0361437 A1 11/2021 Lang et al.
2021/0369289 A1 12/2021 Lee
2021/0369305 A1 12/2021 Rhodes et al.
2021/0378687 A1 12/2021 Mcginley et al.
2021/0378752 A1 12/2021 Paul et al.
2021/0391058 A1 12/2021 Kostrzewski et al.
2021/0393304 A1 12/2021 Geldwert
2022/0000556 A1 1/2022 Casey et al.
2022/0008085 A1 1/2022 Carroll et al.
2022/0015861 A1 1/2022 Basta
2022/0022894 A1 1/2022 Allard et al.
2022/0031396 A1 2/2022 Ryan et al.
2022/0031475 A1 2/2022 Deransart et al.
2022/0079645 A1 3/2022 Smith et al.
2022/0079678 A1 3/2022 Mckinnon et al.
2022/0084651 A1 3/2022 Farley et al.
2022/0087822 A1 3/2022 Radermacher et al.
2022/0087827 A1 3/2022 Bojarski et al.
2022/0110685 A1 4/2022 Mcguan et al.
2022/0125515 A1 4/2022 Mcguan et al.
2022/0133484 A1 5/2022 Lang

(56) References Cited

U.S. PATENT DOCUMENTS

| | | | | |
|---|---|---|---|---|
| 2022/0156942 | A1 | 5/2022 | Chaoui et al. | |
| 2022/0160430 | A1 | 5/2022 | Landon et al. | |
| 2022/0211387 | A1* | 7/2022 | Perler | A61B 17/1775 |
| 2022/0249143 | A1* | 8/2022 | Hollis | A61B 17/8061 |
| 2022/0398817 | A1 | 12/2022 | Chaoui et al. | |
| 2023/0019873 | A1 | 1/2023 | Landon et al. | |

FOREIGN PATENT DOCUMENTS

| | | | |
|---|---|---|---|
| AU | 2015203808 | B2 | 9/2017 |
| AU | 2016323600 | A1 | 4/2018 |
| AU | 2019246771 | A1 | 10/2019 |
| AU | 2020220169 | B2 | 9/2021 |
| AU | 2021286392 | A1 | 1/2022 |
| CA | 1291825 | C | 11/1991 |
| CA | 2491824 | A1 | 9/2005 |
| CA | 2854997 | A1 | 5/2013 |
| CA | 2995627 | A1 | 2/2017 |
| CA | 2998481 | A1 | 3/2017 |
| CH | 695846 | A5 | 9/2006 |
| CN | 2930668 | Y | 8/2007 |
| CN | 201558162 | U | 8/2010 |
| CN | 201572172 | U | 9/2010 |
| CN | 201586060 | U | 9/2010 |
| CN | 201912210 | U | 8/2011 |
| CN | 101237835 | B | 11/2012 |
| CN | 202801773 | U | 3/2013 |
| CN | 103462675 | A | 12/2013 |
| CN | 103505276 | A | 1/2014 |
| CN | 203458450 | U | 3/2014 |
| CN | 102860860 | B | 5/2014 |
| CN | 203576647 | U | 5/2014 |
| CN | 104490460 | A | 4/2015 |
| CN | 104510523 | A | 4/2015 |
| CN | 104523327 | A | 4/2015 |
| CN | 104546102 | A | 4/2015 |
| CN | 204379413 | U | 6/2015 |
| CN | 204410951 | U | 6/2015 |
| CN | 204428143 | U | 7/2015 |
| CN | 204428144 | U | 7/2015 |
| CN | 204428145 | U | 7/2015 |
| CN | 204446081 | U | 7/2015 |
| CN | 106236185 | A | 12/2016 |
| CN | 205924106 | U | 2/2017 |
| CN | 206151532 | U | 5/2017 |
| CN | 105105853 | B | 7/2017 |
| CN | 108030532 | A | 5/2018 |
| CN | 207721902 | U | 8/2018 |
| CN | 109223098 | A | 1/2019 |
| CN | 112914724 | B | 2/2022 |
| DE | 2910627 | A1 | 9/1980 |
| DE | 202006010241 | U1 | 2/2007 |
| DE | 102007053058 | B3 | 4/2009 |
| EP | 0097001 | A1 | 12/1983 |
| EP | 0685206 | A1 | 12/1995 |
| EP | 1508316 | B1 | 5/2007 |
| EP | 1897509 | B1 | 7/2009 |
| EP | 2124772 | A1 | 12/2009 |
| EP | 2124832 | B1 | 8/2012 |
| EP | 2632349 | A1 | 9/2013 |
| EP | 2665428 | A1 | 11/2013 |
| EP | 2742878 | A1 | 6/2014 |
| EP | 2750617 | A1 | 7/2014 |
| EP | 2844162 | A2 | 3/2015 |
| EP | 2849684 | A1 | 3/2015 |
| EP | 2856951 | A1 | 4/2015 |
| EP | 2685914 | B1 | 9/2015 |
| EP | 2624764 | B1 | 12/2015 |
| EP | 3023068 | A2 | 5/2016 |
| EP | 3000443 | A3 | 7/2016 |
| EP | 2713921 | B1 | 10/2017 |
| EP | 2083758 | B1 | 11/2017 |
| EP | 3384865 | A1 | 10/2018 |
| EP | 3013256 | B1 | 11/2018 |
| EP | 3171795 | B1 | 11/2018 |
| EP | 3349674 | A4 | 5/2019 |
| EP | 3672535 | A1 | 7/2020 |
| EP | 3307182 | B1 | 11/2020 |
| EP | 3740141 | B1 | 11/2020 |
| EP | 2558010 | B1 | 5/2021 |
| EP | 3714844 | A4 | 8/2021 |
| EP | 3745969 | A4 | 10/2021 |
| EP | 3926639 | A1 | 12/2021 |
| EP | 3948895 | A1 | 2/2022 |
| EP | 3810019 | A4 | 3/2022 |
| FR | 2362616 | A1 | 3/1978 |
| FR | 2764183 | B1 | 11/1999 |
| FR | 2953120 | B1 | 1/2012 |
| FR | 3030221 | A1 | 6/2016 |
| GB | 2154143 | A | 9/1985 |
| GB | 2154144 | A | 9/1985 |
| GB | 2334214 | B | 1/2003 |
| GB | 2515510 | | 8/2013 |
| GB | 2589960 | A | 10/2020 |
| JP | S635739 | A | 1/1988 |
| JP | 2004174265 | A | 6/2004 |
| JP | 2006158972 | A | 6/2006 |
| JP | 4134243 | B2 | 6/2008 |
| JP | 4162380 | B2 | 8/2008 |
| JP | 2011092405 | A | 5/2011 |
| JP | 4796943 | B2 | 8/2011 |
| JP | 5466647 | B2 | 1/2014 |
| JP | 2014511207 | A | 5/2014 |
| JP | 2014521384 | A | 8/2014 |
| JP | 5628875 | B2 | 10/2014 |
| KR | 100904142 | B1 | 6/2009 |
| KR | 101952368 | B1 | 2/2019 |
| MD | 756 | Z | 11/2014 |
| RU | 2098036 | C1 | 12/1997 |
| RU | 2195892 | C2 | 1/2003 |
| RU | 2320287 | C1 | 3/2008 |
| RU | 2321366 | C2 | 4/2008 |
| RU | 2321369 | C1 | 4/2008 |
| RU | 2346663 | C2 | 2/2009 |
| RU | 2412662 | C1 | 2/2011 |
| RU | 182499 | U1 | 8/2018 |
| SU | 1333328 | A2 | 8/1987 |
| WO | 0166022 | A1 | 9/2001 |
| WO | 03075775 | A1 | 9/2003 |
| WO | 2004089227 | A2 | 10/2004 |
| WO | 2008051064 | A1 | 5/2008 |
| WO | 2008076559 | A1 | 6/2008 |
| WO | 2009001083 | A1 | 12/2008 |
| WO | 2009029798 | A1 | 3/2009 |
| WO | 2009032101 | A2 | 3/2009 |
| WO | 2009045960 | A1 | 4/2009 |
| WO | 2009105196 | A1 | 8/2009 |
| WO | 2010099231 | A2 | 9/2010 |
| WO | 2010099231 | A3 | 11/2010 |
| WO | 2011005327 | A1 | 1/2011 |
| WO | 2011037885 | A1 | 3/2011 |
| WO | 2012024317 | A2 | 2/2012 |
| WO | 2012029008 | A1 | 3/2012 |
| WO | 2012088036 | A1 | 6/2012 |
| WO | 2012176077 | A1 | 12/2012 |
| WO | 2013041618 | A1 | 3/2013 |
| WO | 2013090392 | A1 | 6/2013 |
| WO | 2013134387 | A1 | 9/2013 |
| WO | 2013156816 | A2 | 10/2013 |
| WO | 2013169475 | A1 | 11/2013 |
| WO | 2014020561 | A1 | 2/2014 |
| WO | 2014022055 | A1 | 2/2014 |
| WO | 2014035991 | A1 | 3/2014 |
| WO | 2014085882 | A1 | 6/2014 |
| WO | 2014147099 | A1 | 9/2014 |
| WO | 2014152219 | A2 | 9/2014 |
| WO | 2014152535 | A1 | 9/2014 |
| WO | 2014154266 | A1 | 10/2014 |
| WO | 2014177783 | A1 | 11/2014 |
| WO | 2014200017 | A1 | 12/2014 |
| WO | 2015003284 | A2 | 1/2015 |
| WO | 2015003284 | A3 | 4/2015 |
| WO | 2015094409 | A1 | 6/2015 |
| WO | 2015105880 | A1 | 7/2015 |

(56) References Cited

FOREIGN PATENT DOCUMENTS

| | | | |
|---|---|---|---|
| WO | 2015127515 | A2 | 9/2015 |
| WO | 2016012731 | A1 | 1/2016 |
| WO | 2016102025 | A1 | 6/2016 |
| WO | 2016134160 | A1 | 8/2016 |
| WO | 2017031000 | A1 | 2/2017 |
| WO | 2018167369 | A1 | 9/2018 |
| WO | 2019060780 | A2 | 3/2019 |
| WO | 2019052622 | A4 | 5/2019 |
| WO | 2019091537 | A1 | 5/2019 |
| WO | 2020163314 | A1 | 8/2020 |
| WO | 2020239909 | A3 | 2/2021 |
| WO | 2021054518 | A1 | 3/2021 |
| WO | 2021028636 | A3 | 4/2021 |
| WO | 2021118733 | A1 | 6/2021 |
| WO | 2021127625 | A1 | 6/2021 |
| WO | 2021236838 | A1 | 11/2021 |
| WO | 2021240290 | A1 | 12/2021 |
| WO | 2022033648 | A1 | 2/2022 |

OTHER PUBLICATIONS

Dayton et al., "The Extended Knee Hemilithotomy Position for Gastrocnemius Recession," The Journal of Foot and Ankle Surgery, vol. 49, 2010, pp. 214-216.
Wienke et al., "Bone Stimulation For Nonunions: What the Evidence Reveals," Podiatry Today, vol. 24, No. 9, Sep. 2011, pp. 52-57.
Dayton et al., "Hallux Varus as Complication of Foot Compartment Syndrome," The Journal of Foot and Ankle Surgery, vol. 50, 2011, pp. 504-506.
Dayton et al., "Measurement of Mid-Calcaneal Length on Plain Radiographs: Reliability of a New Method," Foot and Ankle Specialist, vol. 4, No. 5, Oct. 2011, pp. 280-283.
Dayton et al., "A User-Friendly Method of Pin Site Management for External Fixators," Foot and Ankle Specialist, Sep. 16, 2011, 4 pages.
Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.
Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.
Dayton et al., "Technique for Minimally Invasive Reduction of Calcaneal Fractures Using Small Bilateral External Fixation," The Journal of Foot and Ankle Surgery, Article in Press, 2014, 7 pages.
Dayton et al., "Clarification of the Anatomic Definition of the Bunion Deformity," The Journal of Foot and Ankle Surgery, vol. 53, 2014, pp. 160-163.
Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.
Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.
Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.
Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.
Dayton et al., "Principles of Management of Growth Plate Fractures in the Foot and Ankle," Clinics in Podiatric Medicine and Surgery, Pediatric Foot Deformities, Oct. 2013, 17 pages.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, Article in Press, 2014, 4 pages.
Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.
Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.
Catanese et al., "Measuring Sesamoid Position in Hallux Valgus: When Is the Sesamoid Axial View Necessary," Foot and Ankle Specialist, 2014, 3 pages.
Dayton et al., "Comparison of Complications for Internal and External Fixation for Charcot Reconstruction: A Systematic Review," The Journal of Foot and Ankle Surgery, Article in Press, 2015, 4 pages.
Dayton et al., "A new triplanar paradigm for bunion management," Lower Extremity Review, Apr. 2015, 9 pages.
Dayton et al., "American College of Foot and Ankle Surgeons' Clinical Consensus Statement: Perioperative Prophylactic Antibiotic Use in Clean Elective Foot Surgery," The Journal of Foot and Ankle Surgery, Article in Press, 2015, 7 pages.
Dayton et al., "Complications of Metatarsal Suture Techniques for Bunion Correction: A Systematic Review of the Literature," The Journal of Foot and Ankle Surgery, Article in Press, 2015, 3 pages.
DeCarbo et al., "The Weil Osteotomy: A Refresher," Techniques in Foot and Ankle Surgery, vol. 13, No. 4, Dec. 2014, pp. 191-198.
DeCarbo et al., "Resurfacing Interpositional Arthroplasty for Degenerative Joint Diseas of the First Metatarsalphalangeal Joint," Podiatry Management, Jan. 2013, pp. 137-142.
DeCarbo et al., "Locking Plates: Do They Prevent Complications?," Podiatry Today, Apr. 2014, 7 pages.
Easley et al., "Current Concepts Review: Hallux Valgus Part II: Operative Treatment," Foot and Ankle International, vol. 28, No. 6, Jun. 2007, pp. 748-758.
Kim et al., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.
Easley et al., "Current Concepts Review: Hallux Valgus Part I: Pathomechanics, Clinical Assessment, and Nonoperative Management," Foot and Ankle International, vol. 28, No. 5, May 2007, pp. 654-659.
Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.
Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.
Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.
Easley et al., "What is the Best Treatment for Hallux Valgus?," Evidence-Based Orthopaedics—The Best Answers to Clinical Questions, Chapter 73, 2009, pp. 479-491.
Shurnas et al., "Proximal Metatarsal Opening Wedge Osteotomy," Operative Techniques in Foot and Ankle Surgery, Section I, Chapter 13, 2011, pp. 73-78.
Coetzee et al., "Revision Hallux Valgus Correction," Operative Techniques in Foot and Ankle Surgery, Section I, Chapter 15, 2011, pp. 84-96.
Le et al., "Tarsometatarsal Arthrodesis," Operative Techniques in Foot and Ankle Surgery, Section II, Chapter 40, 2011, pp. 281-285.
Collan et al., "The biomechanics of the first metatarsal bone in hallux valgus: A preliminary study utilizing a weight bearing extremity CT," Foot and Ankle Surgery, vol. 19, 2013, pp. 155-161.
Eustace et al., "Hallux valgus, first metatarsal pronation and collapse of the medial longitudinal arch—a radiological correlation," Skeletal Radiology, vol. 23, 1994, pp. 191-194.

(56) References Cited

OTHER PUBLICATIONS

Mizuno et al., "Detorsion Osteotomy of the First Metatarsal Bone in Hallux Valgus," Japanese Orthopaedic Association, Tokyo, 1956; 30:813-819.
Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.
Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664-670.
D'Amico et al., "Motion of the First Ray: Clarification Through Investigation," Journal of the American Podiatry Association, vol. 69, No. 1, Jan. 1979, pp. 17-23.
Groves, "Operative Report," St. Tammany Parish Hospital, Date of Procedure, Mar. 26, 2014, 2 pages.
Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.
Crawford et al., "Metatarsus Adductus: Radiographic and Pathomechanical Analysis," Chapter 5, 2014, 6 pages.
Chesser et al., "New Advances With The Tarsometatarsal Arthrodesis," Podiatry Today, vol. 30, No. 10, Sep. 27, 2017, 15 pages.
Ferrari et al., "A Radiographic Study of the Relationship Between Metatarsus Adductus and Hallux Valgus," The Journal of Foot and Ankle Surgery, vol. 42, No. 1, 2003, pp. 9-14.
Ghali et al., "The Management of Metatarsus Adductus et Supinatus," The Journal of Bone and Joint Surgery, vol. 66-B, No. 3, May 1984, pp. 376-380.
"Arthrodesis of the Tarsometatarsal Joint," Retrieved from https://musculoskeletalkey.com/arthrodesis-of-the-tarsometatarsal-joint/, posted Apr. 18, 2019, 11 pages.
Dayton, "Tarsal-Metatarsal Joint: Primary & Revision Arthrodesis," Apr. 2014, 38 pages.
Nagy et al., "The AO Ulnar Shortening Osteotomy System Indications and Surgical Technique," Journal of Wrist Surgery, vol. 3, No. 2, 2014, pp. 91-97.
NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.
Odenbring et al., "A guide instrument for high tibial osteotomy," Acta Orthopaedica Scandinavica, vol. 60, No. 4, 1989, pp. 449-451.
Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.
Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.
Otsuki et al., "Developing a novel custom cutting guide for curved per-acetabular osteotomy," International Orthopaedics (SICOT), vol. 37, 2013, pp. 1033-1038.
Patel et al., "Modified Lapidus Arthrodesis: Rate of Nonunion in 227 Cases," The Journal of Foot & Ankle Surgery, vol. 43, No. 1, Jan./Feb. 2004, pp. 37-42.
"Patient to Patient Precision, Accu-Cut, Osteotomy Guide System," BioPro, Foot & Ankle International Journal, vol. 23, No. 8, Aug. 2002, 2 pages.
Peters et al., "Flexor Hallucis Longus Tendon Laceration as a Complication of Total Ankle Arthroplasty," Foot & Ankle International, vol. 34, No. 1, 2013, pp. 148-149.
"Prophecy Inbone Preoperative Navigation Guides," Wright Medical Technology, Inc., Nov. 2013, 6 pages.
"Rayhack Ulnar Shortening Generation II Low-Profile Locking System Surgical Technique," Wright Medical Technology, Inc., Dec. 2013, 20 pages.
Rx-Fix Mini Rail External Fixator, Wright Medical Technology, Brochure, Aug. 15, 2014, 2 pages.
Saltzman et al., "Prospective Controlled Trial of STAR Total Ankle Replacement Versus Ankle Fusion: Initial Results," Foot & Ankle International, vol. 30, No. 7, Jul. 2009, pp. 579-596.
Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).
Scranton Jr. et al., "Anatomic Variations in the First Ray: Part I. Anatomic Aspects Related to Bunion Surgery," Clinical Orthopaedics and Related Research, vol. 151, Sep. 1980, pp. 244-255.
Siddiqui et al. "Fixation Of Metatarsal Fracture With Bone Plate In A Dromedary Heifer," Open Veterinary Journal, vol. 3, No. 1, 2013, pp. 17-20.
Sidekick Stealth Rearfoot Fixator, Wright Medical Technology, Surgical Technique, Dec. 2, 2013, 20 pages.
Simpson et al., "Computer-Assisted Distraction Ostegogenesis By Ilizarov's Method," International Journal of Medical Robots and Computer Assisted Surgery, vol. 4, No. 4, Dec. 2008, pp. 310-320, (Abstract Only).
Small Bone External Fixation System, Acumed, Surgical Technique, Effective date Sep. 2014, 8 pages.
"Smith & Nephew scores a HAT-TRICK with its entry into the high-growth hammer toe repair market," Smith & Nephew, Jul. 31, 2014, 2 pages.
Stableloc External Fixation System, Acumed, Product Overview, Effective date Sep. 2015, 4 pages.
Stahl et al., "Derotation Of Post-Traumatic Femoral Deformities By Closed Intramedullary Sawing," Injury, vol. 37, No. 2, Feb. 2006, pp. 145-151, (Abstract Only).
Talbot et al.,"Assessing Sesamoid Subluxation: How Good is the AP Radiograph?," Foot and Ankle International, vol. 19, No. 8, Aug. 1998, pp. 547-554.
TempFix Spanning the Ankle Joint Half Pin and Transfixing Pin Techniques, Biomet Orthopedics, Surgical Technique, 2012, 16 pages.
Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.
Tricot et al., "3D-corrective osteotomy using surgical guides for posttraumatic distal humeral deformity," Acta Orthopaedica Belgica, vol. 78, No. 4, 2012, pp. 538-542.
Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.
Vitek, "Neue Techniken in der Fuβchirurgie Das V-tek-System," ABW Wissenschaftsverlag GmbH, 2009, 11 pages, including English Abstract.
Weber et al., "A Simple System For Navigation Of Bone Alignment Osteotomies Of The Tibia," International Congress Series, vol. 1268, Jan. 2004, pp. 608-613, (Abstract Only).
Weil et al., "Anatomic Plantar Plate Repair Using the Weil Metatarsal Osteotomy Approach," Foot & Ankle Specialist, vol. 4, No. 3, 2011, pp. 145-150.
Wendl et al., "Navigation in der Knieendoprothetik," OP-Journal, vol. 17, 2002, pp. 22-27, including English Abstract.
Whipple et al., "Zimmer Herbert Whipple Bone Screw System: Surgical Techniques for Fixation of Scaphoid and Other Small Bone Fractures," Zimmer, 2003, 59 pages.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Yasuda et al., "Proximal Supination Osteotomy of the First Metatarsal for Hallux Valgus," Foot and Ankle International, vol. 36, No. 6, Jun. 2015, pp. 696-704.
Conti et al., "Effect of the Modified Lapidus Procedure for Hallux Valgus on Foot Width," Foot & Ankle International, Feb. 1, 2020, published online: Oct. 30, 2019, 6 pages.
Cruz et al., "Does Hallux Valgus Exhibit a Deformity Inherent to the First Metatarsal Bone?" The Journal of Foot & Ankle Surgery, vol. 58, No. 6, Nov. 2019, pp. 1210-1214.

(56) References Cited

OTHER PUBLICATIONS

Dahlgren et al., "First Tarsometatarsal Fusion Using Saw Preparation vs. Standard Preparation of the Joint: A Cadaver Study," Foot & Ankle Orthopaedics, vol. 4, No. 4, Oct. 2019, 2 pages.
Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.
Hatch et al., "Triplane Hallux Abducto Valgus Classification," The Journal of Foot & Ankle Surgery, vol. 57, No. 5, Sep./Oct. 2018, published online: May 18, 2018, pp. 972-981.
Langan et al., "Maintenance of Correction of the Modified Lapidus Procedure With a First Metatarsal to Intermediate Cuneiform Cross-Screw Technique," Foot & Ankle International, vol. 41, No. 4, Apr. 1, 2020, published online: Dec. 26, 2019, pp. 426-436.
Li et al., "Evolution of Thinking of the Lapidus Procedure and Fixation," Foot and Ankle Clinics, vol. 25, No. 1, Mar. 2020, published online: Dec. 16, 2019, pp. 18 pages.
Lopez et al., "Metatarsalgia: Assessment Algorithm and Decision Making," Foot and Ankle Clinics, vol. 24, No. 4, Dec. 2019, published online: Sep. 25, 2019, pp. 561-569.
Ray et al., "Multicenter Early Radiographic Outcomes of Triplanar Tarsometatarsal Arthrodesis With Early Weightbearing," Foot & Ankle International, vol. 40, No. 8, Aug. 1, 2019, published online: May 5, 2019, 7 pages.
Walker et al., "The Role of First Ray Insufficiency in the Development of Metatarsalgia," Foot and Ankle Clinics, vol. 24, No. 4, Dec. 2019, published online: Sep. 5, 2019, pp. 641-648.
Dayton et al., "Comparison of Radiographic Measurements Before and After Triplane Tarsometatarsal Arthrodesis for Hallux Valgus," The Journal of Foot & Ankle Surgery, vol. 59, 2020, pp. 291-297.
Dayton et al., "Evidence-Based Bunion Surgery: A Critical Examination of Current and Emerging Concepts and Techniques," Springer International Publishing, 2017, 254 pages.
Dayton et al., "Comparison of Tibial Sesamoid Position on Anteroposterior and Axial Radiographs Before and After Triplane Tarsal Metatarsal Joint Arthrodesis," The Journal of Foot & Ankle Surgery, vol. 56, 2017, pp. 1041-1046.
Dayton et al., "Biomechanical Characteristics of Biplane Multiplanar Tension-Side Fixation for Lapidus Fusion," The Journal of Foot & Ankle Surgery, vol. 57, 2018, pp. 761-765.
Dayton et al., "Progression of Healing on Serial Radiographs Following First Ray Arthrodesis in the Foot Using a Biplanar Plating Technique Without Compression," The Journal of Foot & Ankle Surgery, 2018, 7 pages.
Vaida et al., "Effect on Foot Width With Triplanar Tarsometatarsal Arthrodesis for Hallux Valgus," Foot & Ankle Orthopaedics, vol. 5, No. 3, 2020, pp. 1-5.
"Patient-specific surgical methods and instrumentation", Treace Medical Concepts, European Patent Application No. 20862480.9, Extended European Search Report mailed Apr. 9, 2023, 8 pages.
Aiyer et al., "Prevalence of Metatarsus Adductus in Patients Undergoing Hallux Valgus Surgery," Foot & Ankle International, vol. 35, No. 12, 2014, pp. 1292-1297.
Bennett et al., "Intraosseous Sliding Plate Fixation Used in Double Osteotomy Bunionectomy," Foot & Ankle International, vol. 40, No. 1, 2019, pp. 85-88.
Buda et al., "Effect of Fixation Type and Bone Graft on Tarsometatarsal Fusion," Foot & Ankle International, vol. 39, No. 12, 2018, pp. 1394-1402.
Chomej et al., "Lateralising Dmmo (Mis) for simultaneous correction of a pes adductus during surgical treatment of a hallux valgus," The Foot, vol. 45, Dec. 2020, 33 pages.
Cichero et al., "Different fixation constructs and the risk of non-union following first metatarsophalangeal joint arthrodesis," Foot and Ankle Surgery, vol. 27, 2021, pp. 789-792.
Curran et al., "Functional Capabilities After First Metatarsal Phalangeal Joint Arthrodesis Using a Locking Plate and Compression Screw Construct," The Journal of Foot & Ankle Surgery, vol. 61, No. 1, Jan./Feb. 2022, pp. 79-83.
Dalat et al., "Does arthrodesis of the first metatarsophalangeal joint correct the intermetatarsal M1M2 angle? Analysis of a continuous series of 208 arthrodeses fixed with plates," Orthopaedics & Traumatology: Surgery & Research, vol. 101, 2015, pp. 709-714.
DeHeer et al., "Procedure-Specific Hardware Removal After Evans Osteotomy," Journal of the American Podiatric Medical Association, vol. 110, No. 2, Mar./Apr. 2020, 7 pages.
Fazal et al., "First metatarsophalangeal joint arthrodesis with two orthogonal two hole plates," Acta Orthopaedica et Traumatologica Turcica, vol. 52, 2018, pp. 363-366.
Ferreyra et al., "Can we correct first metatarsal rotation and sesamoid position with the 3D Lapidus procedure?," Foot and Ankle Surgery, vol. 28, No. 3, Apr. 2022, pp. 313-318.
Flavin et al., "Arthrodesis of the First Metatarsophalangeal Joint Using a Dorsal Titanium Contoured Plate," Foot & Ankle International, vol. 25, No. 11, Nov. 2004, pp. 783-787.
Fraissler et al., "Treatment of hallux valgus deformity," Efort Open Reviews, vol. 1, Aug. 2016, pp. 295-302.
Gould et al., "A Prospective Evaluation of First Metatarsophalangeal Fusion Using an Innovative Dorsal Compression Plating System," The Journal of Foot & Ankle Surgery, vol. 60, 2021, pp. 891-896.
Gutteck et al., "Comparative study of Lapidus bunionectomy using different osteosynthesis methods," Foot and Ankle Surgery, vol. 19, 2013, pp. 218-221.
Gutteck et al., "Is it feasible to rely on intraoperative X ray in correcting hallux valgus?," Archives of Orthopaedic and Trauma Surgery, vol. 133, 2013, pp. 753-755.
Ho et al., "Hallux rigidus," Efort Open Reviews, vol. 2, Jan. 2017, pp. 13-20.
Hunt et al., "Locked Versus Nonlocked Plate Fixation For Hallux MTP Arthrodesis," Foot and Ankle International, vol. 32, No. 7, Jul. 2011, pp. 704-709.
Jackson III et al., "The Surgical Learning Curve for Modified Lapidus Procedure for Hallux Valgus Deformity," Foot & Ankle Specialist, Jul. 2021, 5 pages.
Jeuken et al., "Long-term Follow-up of a Randomized Controlled Trial Comparing Scarf to Chevron Osteotomy in Hallux Valgus Correction," Foot & Ankle International, vol. 37, No. 7, 2016, pp. 687-695.
Klos et al., "Modified Lapidus arthrodesis with plantar plate and compression screw for treatment of hallux valgus with hypermobility of the first ray: A preliminary report," Foot and Ankle Surgery, vol. 19, 2013, pp. 239-244.
Kurup et al., "Midfoot arthritis- current concepts review," Journal of Clinical Orthopaedics and Trauma, vol. 11, 2020, pp. 399-405.
La Reaux et al., "Metatarsus adductus and hallux abducto valgus: their correlation," The Journal of Foot Surgery, vol. 26, No. 4, Jul. 1987, pp. 304-308, Abstract Only.
Latif et al., "First metatarsophalangeal fusion using joint specific dorsal plate with interfragmentary screw augmentation: Clinical and radiological outcomes," Foot and Ankle Surgery, vol. 25, 2019, pp. 132-136.
Little, "Joint Arthrodesis For Hallux Valgus," Clinics in Podiatric Medicine and Surgery, Hallux Abducto Valgus Surgery, updated Apr. 19, 2014, retrieved online from <https://www.footankleinstitute.com/first-metatarsophalangeal-joint-arthrodesis-in-the-treatment-of-hallux-valgus>, 7 pages.
Machacek Jr. et al., "Salvage of a Failed Keller Resection Arthroplasty," The Journal of Bone and Joint Surgery, vol. 86A, No. 6, Jun. 2004, pp. 1131-1138.
Marshall et al., "The identification and appraisal of assessment tools used to evaluate metatarsus adductus: a systematic review of their measurement properties," Journal of Foot and Ankle Research, vol. 11, No. 25, 2018, 10 pages.
McAleer et al., "Radiographic Outcomes Following Triplanar Correction of Combined Hallux Valgus and Metatarsus Adductus Deformities," ACFAS Scientific Conference, Poster, Feb. 2022, 1 page.

(56) References Cited

OTHER PUBLICATIONS

McCabe et al., "Anatomical reconstruction of first ray instability hallux valgus with a medial anatomical TMTJ1 plate," Foot and Ankle Surgery, vol. 27, No. 8, Dec. 2021, pp. 869-873.
Mehtar et al., "Outcomes of bilateral simultaneous hallux MTPJ fusion," Foot and Ankle Surgery, vol. 27, 2021, pp. 213-216.
Miller et al., "Variable Angle Locking Compression Plate as Alternative Fixation for Jones Fractures: A Case Series," Kansas Journal of Medicine, vol. 12, No. 2, May 2019, pp. 28-32.
Nix et al., "Prevalence of hallux valgus in the general population: a systematic review and meta-analysis," Journal of Foot and Ankle Research, vol. 3, No. 21, 2010, 9 pages.
Park et al., "Comparative analysis of clinical outcomes of fixed-angle versus variable-angle locking compression plate for the treatment of Lisfranc injuries," Foot and Ankle Surgery, vol. 26, 2020, pp. 338-342.
Pentikainen et al., "Preoperative Radiological Factors Correlated to Long-Term Recurrence of Hallux Valgus Following Distal Chevron Osteotomy," Foot & Ankle International, vol. 35, No. 12, 2014, pp. 1262-1267.
Shima et al., "Operative Treatment for Hallux Valgus With Moderate to Severe Metatarsus Adductus," Foot & Ankle International, vol. 40, No. 6, 2019, pp. 641-647.
Simons et al., "Short-Term Clinical Outcome of Hemiarthroplasty Versus Arthrodesis for End-Stage Hallux Rigidus," The Journal of Foot & Ankle Surgery, vol. 54, 2015, pp. 848-851.
Weigelt et al., "Risk Factors for Nonunion After First Metatarsophalangeal Joint Arthrodesis With a Dorsal Locking Plate and Compression Screw Construct: Correction of Hallux Valgus Is Key," The Journal of Foot & Ankle Surgery, vol. 60, No. 6, Nov./Dec. 2021, pp. 1179-1183.
Williams et al., "Metatarsus adductus: Development of a non-surgical treatment pathway," Journal of Paediatrics and Child Health, vol. 49, 2013, pp. E428-433.
Hatch et al., "Analysis of Shortening and Elevation of the First Ray With Instrumented Triplane First Tarsometatarsal Arthrodesis," Foot & Ankle Orthopaedics, vol. 5, No. 4, 2020, pp. 1-8.
Ray et al., "Hallux Valgus," Foot & Ankle Orthopaedics, vol. 4, No. 2, 2019, pp. 1-12.
Santrock et al., "Hallux Valgus Deformity and Treatment: A Three-Dimensional Approach: Lapiplasty," Foot & Ankle Clinics, vol. 23, No. 2, 2018, pp. 281-295.
International Patent Application No. PCT/US2021/033256, International Search Report and Written Opinion mailed Sep. 7, 2021, 9 pages.
Smith et al., "Intraoperative Multiplanar Alignment System to Guide Triplanar Correction of Hallux Valgus Deformity," Techniques in Foot & Ankle Surgery, 2017, 8 pages.
Smith et al., "Understanding Frontal Plane Correction in Hallux Valgus Repair," Clinics in Podiatric Medicine and Surgery, vol. 35, 2018, pp. 27-36.
DiNapoli et al., "Metatarsal Osteotomy for the Correction of Metatarsus Adductus," Reconstructive Surgery of the Foot and Leg, 1989, pp. 242-250.
McAleer et al., "A systematic approach to the surgical correction of combined hallux valgus and metatarsus adductus deformities," The Journal of Foot & Ankle Surgery, May 21, 2021, 6 pages.
"Accu-Cut Osteotomy Guide System," BioPro, Brochure, Oct. 2018, 2 pages.
"Acumed Osteotomiesystem Operationstechnik," Acumed, 2014, 19 pages (including 3 pages English translation).
Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.
Alvine et al., "Peg and Dowel Fusion of the Proximal Interphalangeal Joint," Foot & Ankle, vol. 1, No. 2, 1980, pp. 90-94.
Anderson et al., "Uncemented STAR Total Ankle Prostheses," The Journal of Bone and Joint Surgery, vol. 86(1, Suppl 2), Sep. 2004, pp. 103-111, (Abstract Only).
Bednarz et al., "Modified Lapidus Procedure for the Treatment of Hypermobile Hallux Valgus," Foot & Ankle International, vol. 21, No. 10, Oct. 2000, pp. 816-821.
Blomer, "Knieendoprothetik—Herstellerische Probleme und technologische Entwicklungen," Orthopade, vol. 29, 2000, pp. 688-696, including English Abstract on p. 689.
Bouaicha et al., "Fixation of Maximal Shift Scarf Osteotomy with Inside-Out Plating: Technique Tip," Foot & Ankle International, vol. 32, No. 5, May 2011, pp. 567-569.
Carr et al., "Correctional Osteotomy for Metatarsus Primus Varus and Hallux Valgus," The Journal of Bone and Joint Surgery, vol. 50-A, No. 7, Oct. 1968, pp. 1353-1367.
Coetzee et al., "The Lapidus Procedure: A Prospective Cohort Outcome Study," Foot & Ankle International, vol. 25, No. 8, Aug. 2004, pp. 526-531.
Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.
Dayton et al., "Relationship Of Frontal Plane Rotation Of First Metatarsal To Proximal Articular Set Angle And Hallux Alignment In Patients Undergoing Tarsometatarsal Arthrodesis For Hallux Abducto Valgus: A Case Series And Critical Review Of The Literature," The Journal of Foot and Ankle Surgery, vol. 52, No. 3, May/Jun. 2013, pp. 348-354.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.
DiDomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.
Dobbe et al. "Patient-Tailored Plate For Bone Fixation And Accurate 3D Positioning In Corrective Osteotomy," Medical and Biological Engineering and Computing, vol. 51, No. 1-2, Feb. 2013, pp. 19-27, (Abstract Only).
Doty et al., "Hallux valgus and hypermobility of the first ray: facts and fiction," International Orthopaedics, vol. 37, 2013, pp. 1655-1660.
EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.
Boffeli et al., "Can We Abandon Saw Wedge Resection in Lapidus Fusion? A Comparative Study of Joint Preparation Techniques Regarding Correction of Deformity, Union Rate, and Preservation of First Ray Length," The Journal of Foot and Ankle Surgery, vol. 58, No. 6, Nov. 2019, published online: Sep. 25, 2019, pp. 1118-1124.
"Futura Forefoot Implant Arthroplasty Products," Tornier, Inc., 2008, 14 pages.
Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, published online: Nov. 21, 2014, pp. 437-440.
Garthwait, "Accu-Cut System Facilitates Enhanced Precision," Podiatry Today, vol. 18, No. 6, Jun. 2005, 6 pages.
Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.

(56) References Cited

OTHER PUBLICATIONS

Gotte, "Entwicklung eines Assistenzrobotersystems für die Knieendoprothetik," Forschungsberichte, Technische Universitat Munchen, 165, 2002, 11 pages, including partial English Translation.
Gregg et al., "Plantar plate repair and Weil osteotomy for metatarsophalangeal joint instability," Foot and Ankle Surgery, vol. 13, 2007, pp. 116-121.
Grondal et al., "A Guide Plate for Accurate Positioning of First Metatarsophalangeal Joint during Fusion," Operative Orthopädie Und Traumatologie, vol. 16, No. 2, 2004, pp. 167-178 (Abstract Only).
"HAT-TRICK Lesser Toe Repair System," Smith & Nephew, Brochure, Aug. 2014, 12 pages.
"HAT-TRICK Lesser Toe Repair System, Foot and Ankle Technique Guide, Metatarsal Shortening Osteotomy Surgical Technique," Smith & Nephew, 2014, 16 pages.
Hetherington et al., "Evaluation of surgical experience and the use of an osteotomy guide on the apical angle of an Austin osteotomy," The Foot, vol. 18, 2008, pp. 159-164.
Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.
"Hoffmann II Compact External Fixation System," Stryker, Brochure, Literature No. 5075-1-500, 2006, 12 pages.
"Hoffmann II Micro Lengthener," Stryker, Operative Technique, Literature No. 5075-2-002, 2008, 12 pages.
"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.
Conti et al., "Effect of the Modified Lapidus Procedure on Pronation of the First Ray in Hallux Valgus," Foot & Ankle International, Feb. 1, 2020, published online: Oct. 16, 2019, 8 pages.
Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.
"Lag Screw Target Bow," Stryker Leibinger GmbH & Co. KG, Germany 2004, 8 pages.
Lapidus, "The Author's Bunion Operation From 1931 to 1959," Clinical Orthopaedics, vol. 16, 1960, pp. 119-135.
Lieske et al., "Implantation einer Sprunggelenktotalendo-prothese vom Typ Salto 2," Operative Orthopädie und Traumatologie, vol. 26, No. 4, 2014, pp. 401-413, including English Abstract on p. 403.
MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.
Magin, "Computernavigierter Gelenkersatz am Knie mit dem Orthopilot," Operative Orthopädie und Traumatologie, vol. 22, No. 1, 2010, pp. 63-80, including English Abstract on p. 64.
Magin, "Die belastungsstabile Lapidus-Arthrodese bei Hallux-valgus-Deformität mittels IVP-Plattenfixateur (V-TEK- System)," Operative Orthopädie und Traumatologie, vol. 26, No. 2, 2014, pp. 184-195, including English Abstract on p. 186.
Michelangelo Bunion System, Surgical Technique, Instratek Incorporated, publication date unknown, 4 pages.
Mini Joint Distractor, Arthrex, retrieved Dec. 19, 2014, from the Internet: <http://www.arthrex.com/foot-ankle/mini-joint-distractor/products>, 2 pages.
MiniRail System, Small Bone Innovations, Surgical Technique, 2010, 24 pages.
Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.
Modular Rail System: External Fixator, Smith & Nephew, Surgical Technique, 2013, 44 pages.
Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).
Moore et al., "Effect Of Ankle Flexion Angle On Axial Alignment Of Total Ankle Replacement," Foot and Ankle International, vol. 31, No. 12, Dec. 2010, pp. 1093-1098, (Abstract Only).
Mortier et al., "Axial Rotation of the First Metatarsal Head in a Normal Population and Hallux Valgus Patients," Orthopaedics and Traumatology: Surgery and Research, vol. 98, 2012, pp. 677-683.
Defendant Fusion Orthopedics LLC's Invalidity Contentions, No. CV-22-00490-PHX-SRB, US District Court for the District of Arizona, Aug. 27, 2022, 41 pages.
Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.
Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.
Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.
Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.
Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.
Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.
Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.
Obviousness Chart, Exhibit C of Defendant Fusion Orthopedics LLC's Invalidity Contentions, No. CV-22-00490-PHX-SRB, US District Court for the District of Arizona, Aug. 27, 2022, 153 pages.
"Foot and Ankle Instrument Set," Smith & Nephew, 2013, 2 pages.
"Lapidus Pearls: Gaining Joint Exposure to Decrease Non-Union," Youtube, Retrieved online from <https://www.youtube.com/watch?v =-jqJyE7pj-Y>, dated Nov. 2, 2009, 3 pages.
"Reconstructive Surgery of the Foot & Ankle," The Podiatry Institute, Update 2015, Conference Program, May 2015, 28 pages.
"Speed Continuous Active Compression Implant," BioMedical Enterprises, Inc., A120-029 Rev. 3, 2013, 4 pages.
"Visionaire: Patient Matched Cutting Blocks Surgical Procedure," Smith & Nephew, Inc., 2009, 2 pages.
Arthrex, "Comprehensive Foot System," Retrieved online from <https://www.arthrex.com/resources/animation/8U3iaPvY6kO8bwFAwZF50Q/comprehensive-foot-system?referringTeam=foot_and_ankle>, dated Aug. 27, 2013, 3 pages.

(56) References Cited

OTHER PUBLICATIONS

Baravarian, "Why the Lapidus Procedure is Ideal for Bunions," Podiatry Today, Retrieved online from <https://www.hmpglobal-learhmpgloballe.com/site/podipodi/article/5542>, dated May 2006, 8 pages.
Bauer et al., "Offset-V Osteotomy of the First Metatarsal Shaft in Hallux Abducto Valgus," McGlamry's Comprehensive Textbook of Foot and Ankle Surgery, Fourth Edition, vol. 1, Chapter 29, 2013, 26 pages.
Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
Coughlin, "Fixation of the Lapidus Arthrodesis with a Plantar Interfragmentary Screw and Medial Low Profile Locking Plate, "Orthopaedics and Traumatology, vol. 7, 1999, pp. 133-143.
Dayton et al., "Observed Changes in Radiographic Measurements of the First Ray after Frontal Plane Rotation of the First Metatarsal in a Cadaveric Foot Model," The Journal of Foot & Ankle Surgery, vol. 53, 2014, pp. 274-278.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.
DiDomenico et al., "Lapidus Bunionectomy: First Metatarsal-Cuneiform Arthrodesis," McGlamry's Comprehensive Textbook of Foot and Ankle Surgery, Fourth Edition, vol. 1, Chapter 31, 2013, 24 pages.
Fallin et al., US Provisional Application Entitled Indexed Tri-Planar Osteotomy Guide and Method, U.S. Appl. No. 62/118,378, filed Feb. 19, 2015, 62 pages.
Fishco, "A Straightforward Guide To The Lapidus Bunionectomy, "Podiatry Today, Retrieved online from <https:// www.hmpgloballearningnetwork.com/site/podiatry/blogged/straightforward-guide-lapidus-bunionectomy>, dated Sep. 6, 2013, 5 pages.
Fishco, "Making the Lapidus Easy," The Podiatry Institute, Update 2014, Chapter 14, 2014, pp. 91-93.
Fleming et al., "Results of Modified Lapidus Arthrodesis Procedure Using Medial Eminence as an Interpositional Autograft," The Journal of Foot & Ankle Surgery, vol. 50, 2011, pp. 272-275.
Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.
Gerard et al., "The Modified Lapidus Procedure," Orthopedics, vol. 31, No. 3, Mar. 2008, 7 pages.
Giannoudis et al., "Hallux Valgus Correction," Practical Procedures in Elective Orthopaedic Surgery, Pelvis and Lower Extremity, Chapter 38, 2012, 22 pages.
Greiner, "The Jargon of Pedal Movements," Foot & Ankle International, vol. 28, No. 1, Jan. 2007, pp. 109-125.
Groves, "Functional Position Joint Sectioning: Pre-Load Method for Lapidus Arthrodesis," The Podiatry Institute, Update 2015, Chapter 6, 2015, pp. 23-29.
Hardy et al., "Observations on Hallux Valgus," The Journal of Bone and Joint Surgery, vol. 33B, No. 3, Aug. 1951, pp. 376-391.
Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.
Integra, "Integra Large Qwix Positioning and Fixation Screw, Surgical Technique," 2012, 16 pages.
Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.
Lee et al., "Technique Tip: Lateral Soft-Tissue Release for Correction of Hallux Valgus Through a Medial Incision Using A Dorsal Flap Over the First Metatarsal," Foot & Ankle International, vol. 28, No. 8, Aug. 2007, pp. 949-951.
Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.
Myerson, "Cuneiform-Metatarsal Arthrodesis," The Foot and Ankle, Chapter 9, 1997, pp. 107-117.
Sammarco, "Surgical Strategies: Mau Osteotomy for Correction of Moderate and Severe Hallux Valgus Deformity," Foot & Ankle International, vol. 28, No. 7, Jul. 2007, pp. 857-864.
Schon et al., "Cuneiform-Metatarsal Arthrodesis for Hallux Valgus, "The Foot and Ankle, Second Edition, Chapter 8, 2002, pp. 99-117.
Sokoloff, "Lapidus Procedure," Textbook of Bunion Surgery, Chapter 15, 1981, pp. 277-287.
Stamatis et al., "Mini Locking Plate as "Medial Buttress" for Oblique Osteotomy for Hallux Valgus," Foot & Ankle International, vol. 31, No. 10, Oct. 2010, pp. 920-922.
Stewart, "Use for BME Speed Nitinol Staple Fixation for the Lapidus Procedure," date unknown, 1 page.
Wukich et al., "Hypermobility of the First Tarsometatarsal Joint," Foot and Ankle Clinics, vol. 10, No. 1, Mar. 2005, pp. 157-166.
Dayton et al., "Biwinged Excision for Round Pedal Lesions," The Journal of Foot and Ankle Surgery, vol. 35, No. 3, 1996, pp. 244-249.
Dayton et al., "Medial Incision Approach to the First Metatarsophalangeal Joint," The Journal of Foot and Ankle Surgery, vol. 40, No. 6, Nov./Dec. 2001, pp. 414-417.
Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.
Dayton et al., "Use of the Z Osteotomy for Tailor Bunionectomy," The Journal of Foot and Ankle Surgery, vol. 42, No. 3, May/Jun. 2003, pp. 167-169.
Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.
"International Search Report and Written Opinion dated Dec. 17, 2020", For International Application No. PCT/US2020/050764, Dec. 17, 2020.
Additive, Orthopaedics , "The First and Only FDA Approved Patient Specific Talus Spacer", Additive Orthopaedics, "The First and Only FDA Approved Patient Specific Talus Spacer", 2021, 11 pgs https://totaltalusreplacement.com/, 2021, 11 pgs.
Arthrex , "Distal Tibia Allograft Workstation for Glenoid Bone Loss, Surgical Technique", Arthrex, Distal Tibia Allograft Workstation for Glenoid Bone Loss, Surgical Technique, 2018, 8 pp. 2018, 8 pgs.
De Carvalho , et al., "Automated three-dimensional distance and coverage mapping of hallux valgus: a case-control study", De Carvalho et al., "Automated three-dimensional distance and coverage mapping of hallux valgus: a case-control study", J Foot Ankle. 2022;16(1):41-45 https://jfootankle.com/JournalFootAnkle/article/view/1629/1821 retrieved May 26, 2022, May 26, 2022, 41-45.
Disior , "Bonelogic foot & ankle module", Disior, "Bonelogic foot & ankle module", 2022, 6pgs. https://www.disior.com/foot--ankle.html, 2022, 6 pgs.
Dubovik , "Talonavicular joint artrodesis and medial displacement calcaneal osteotomy for treatment of patients with planovalgus deformity", Traumatology and Orthopedics of Russia, 2012:3(65), 83-88 (English Abstract Only), 2012.
Wright Medical , "How Blueprint Works—from CT to 3D [CAW-9389]", Wright Med, "How Blueprint Works—from CT to 3D [CAW-9389]", 2021 https://www.wrightmeded.com/videos/how-blueprint-works-from-ct-to-3d-caw-9389 video at top of page teaches auto segmentation.see time Mark 32 sec to 48 sec, 2021, time 32 s. to 48 s.
Kls Martin Group , "IPS Implants", KLS Martin Group, IPS Implants, 2022, 8 pgs. https://www.klsmartin.com/en-na/products/individual-patient-solutions/ips-implants/, 2022, 8 pgs.
Nyska, Synergy 3D Med , "Anatomical Model: Calcaneus", NYSKA, Synergy 3D Med "Anatomical Model: Calcaneus", 2022, 2022.
Synopsys, Simpleware Automated Solution Mo , "Medical Image Segmentation with Machine Learning", Synopsys, Simpleware Auto-

(56) References Cited

OTHER PUBLICATIONS mated Solution Modules, "Medical Image Segmentation with Machine Learning" 2022, 12 pgs https://www.synopsys.com/simpleware/software/auto-segmenter-modules.html#simpleware-as-ortho, 2022, 12 pgs.
Tornier Technology , "Tornier Blueprint 3D Planning + PSI", Tornier Technology, "Tornier Blueprint 3D Planning + PSI", Feb. 2017, 12 pgs. https://www.wrightemedia.com/ProductFiles/Files/PDFs/CAW-8609_EN_HR_LE.pdf, Feb. 2017, 12 pages.
Total Ankle Institute , "Prophecy: Preoperative Navigation Guides", Total Ankle Institute, "Prophecy: Preoperative Navigation Guides", 2019, 6 pgs https://www.totalankleinstitute.com/infinity-products/prophecy-preoperative-navigation-guides/, 2019, 6 pgs.
Treace Medical Concepts, Inc. , "Adductoplasty Midfoot Correction System", Treace Medical Concepts, Inc. "Adductoplasty Midfoot Correction System" 2022, 9 pgs. https://www.lapiplasty.com/surgeons/other-products/adductoplasty-system/, 2022, 9 pgs.
Virzì, et al., "Comprehensive Review of 3D Segmentation Software Tools for MRI Usable for Pelvic Surgery Planning", Virzì, et al. "Comprehensive Review of 3D Segmentation Software Tools for MRI Usable for Pelvic Surgery Planning." Journal of digital imaging vol. 33,1 (2020): 99-110. doi:10.1007/s10278-019-00239-7, 2020, 99-110.

* cited by examiner

Figure 4:
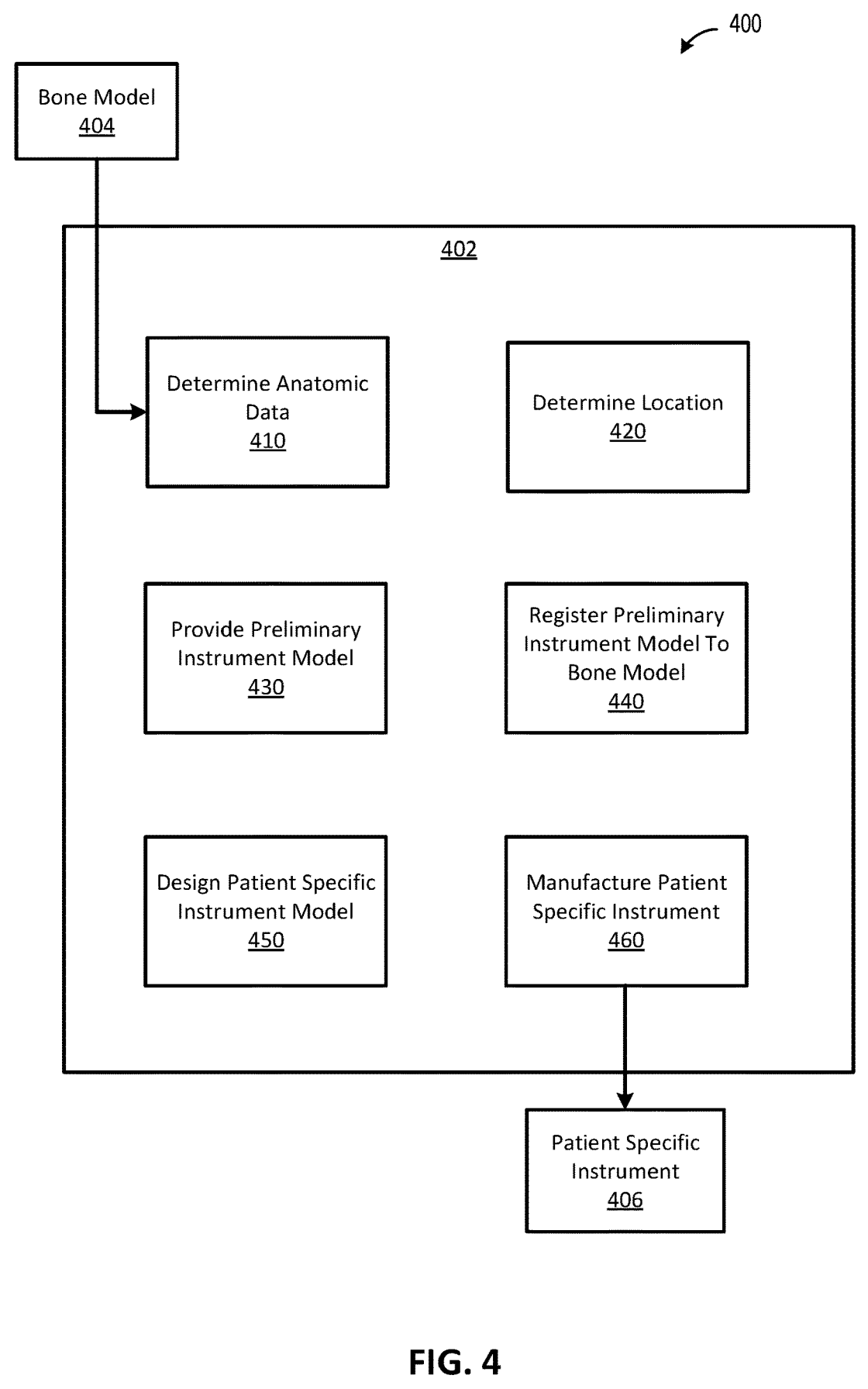

400

Bone Model
404

402

Determine Anatomic Data
410

Determine Location
420

Provide Preliminary Instrument Model
430

Register Preliminary Instrument Model To Bone Model
440

Design Patient Specific Instrument Model
450

Manufacture Patient Specific Instrument
460

Patient Specific Instrument
406

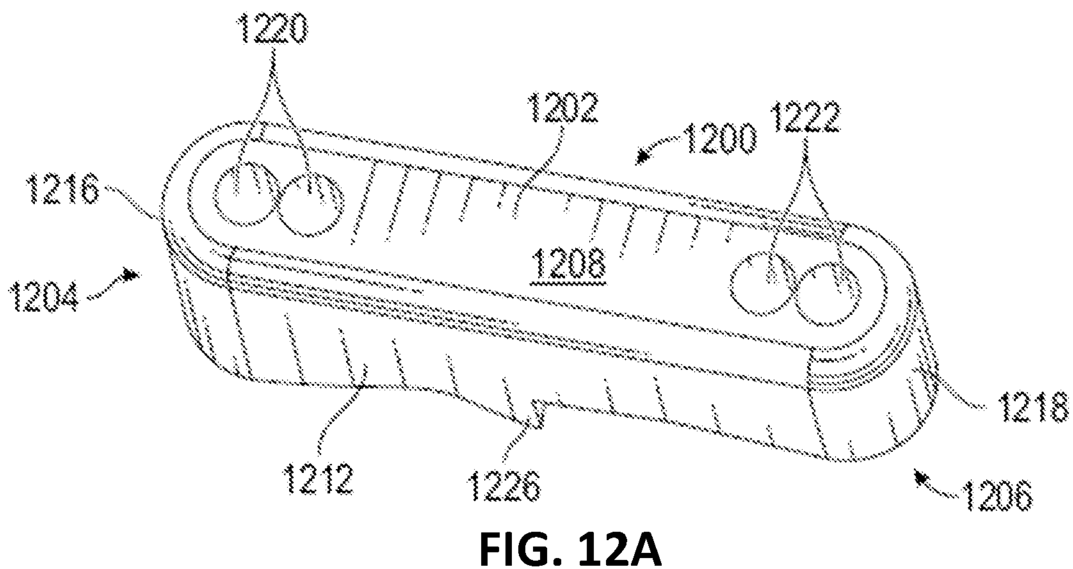
FIG. 12A
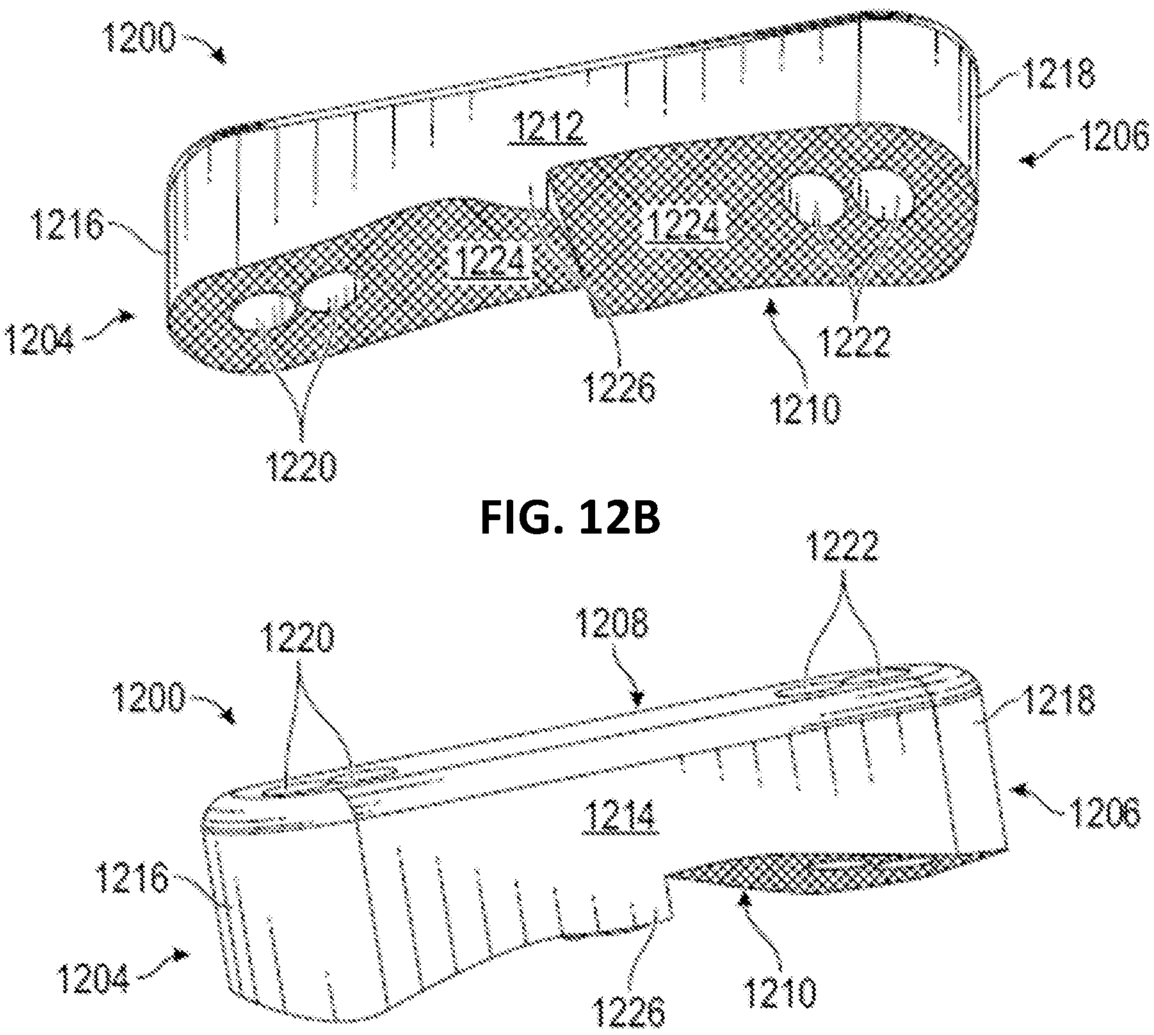
FIG. 12B
FIG. 12C 928
840
930
202
208

928
840
930
202
208

928
930
202
208

928
820a
930
202
208

928
820b
930
202
208

928
1200
930
810c
202
208

APPARATUS, SYSTEM, AND METHOD FOR PATIENT-SPECIFIC METHODS AND INSTRUMENTATION

CROSS-REFERENCE TO RELATED APPLICATIONS

This application claims the benefit of U.S. Provisional Application No. 63/365,126, filed May 20, 2022, which is hereby incorporated by reference in its entirety.

TECHNICAL FIELD

The present disclosure relates to surgical devices, systems, instruments, and methods. More specifically, the present disclosure relates to patient-specific instruments, implants, instruments, and/or methods of designing and using the same.

BACKGROUND

Various bone conditions may be corrected using surgical procedures, in which one or more tendons, ligaments, and/or bones may be cut, replaced, repositioned, reoriented, reattached, fixated and/or fused. These surgical procedures require the surgeon to properly locate, position, and/or orient one or more osteotomy cuts, fixation guides, fixators, bone tunnels, points of attachment for ends of grafts or soft tissue and the like. Determining and locating an optimal location and trajectory for one or more steps of the surgical procedures and/or securing instruments that can guide or assist in steps of the surgical procedures such as performing osteotomies, deploying fixation, and the like, can be challenging, given conventional techniques and instruments. One of the challenges with conventional techniques is how to translate, map, or convert from a model of a patient's anatomy and/or virtual instrumentation to the real, physical world for performing a surgical procedure. Furthermore, surgical procedures can be extra challenging when working on anatomy such as bones of a patient's foot or hand which have much smaller bones that called for extra precision in comparison to larger bones such as a femur. What is needed is one or more instruments to facilitate locating, aligning, orienting, planning, mapping from virtual models to physical anatomy, preparing for, initiating, executing, and/or completing such surgical procedures. In addition, what is needed is methods, apparatus, implants and/or instrumentation that is customized to a specific patient. Existing solutions for guiding orthopedic surgical procedures are inadequate and error prone.

SUMMARY

The various apparatus, devices, systems, and/or methods of the present disclosure have been developed in response to the present state of the art, and in particular, in response to the problems and needs in the art that have not yet been fully solved by currently available technology.

One general aspect of the present disclosure may include an apparatus that may include a proximal end. An apparatus that may also include a distal end. An apparatus that may furthermore include a body having a superior side, an inferior side, a medial side, a lateral side, a proximal side, and a distal side. An apparatus that may in addition include a marker configured to identify a location for a reference feature that corresponds to a model reference for a bone of the patient's foot. An apparatus that may moreover include a bone engagement surface configured to register to an anatomical structure of the bone, the bone engagement surface defined based on medical imaging taken of the bone.

Implementations may also include one or more of the following features. An apparatus where the marker may include: a set of proximal guide pins; a set of distal guide pins; a proximal set of holes that extend from the superior side to the inferior side, the proximal set of holes configured to receive the set of proximal guide pins; a distal set of holes that extend from the superior side to the inferior side, distal set of holes configured to receive the set of distal guide pins; and where the reference feature may include one of the set of proximal guide pins deployed in the bone and the set of distal guide pins deployed in the bone. An apparatus where: the proximal set of holes is spaced from the distal set of holes longitudinally along a long axis of the bone and offset about the long axis by an angle alpha measured in degrees; and where the angle alpha ranges between about 3 degrees and about 100 degrees. An apparatus where the reference feature may include: a first reference feature having the set of proximal guide pins deployed in a bone; and a second reference feature having the set of distal guide pins deployed in a bone. An apparatus where the first reference feature may include a proximal alignment feature and the second reference feature may include a distal alignment feature. An apparatus where the first reference feature may include a proximal resection guide anchor and the second reference feature may include a distal resection guide anchor. An apparatus where: the bone is a metatarsal bone; the body is configured to span a tarsometatarsal (TMT) joint; the inferior side is configured to interface with a cuneiform bone and the metatarsal bone; where the reference feature may include a set of proximal guide pins deployed in the cuneiform bone and a set of distal guide pins deployed in the metatarsal bone; and where the apparatus further may include a coupler between the proximal end and the distal end, the coupler configured to hold the proximal end and the distal end together until an user operates the coupler to separate the proximal end and the distal end. An apparatus may include a frangible section between the proximal end and the distal end, the frangible section configured to separate the proximal end from the distal end by dividing the body in response to a force delivered by a user to the frangible section. An apparatus may include a registration key on the inferior side of the body, the registration key having a protrusion that engages an opening between two bones of a joint. An apparatus may include a bone engagement opening on the inferior side of the body, the bone engagement opening configured to receive at least a portion of the bone when the apparatus is deployed for use.

One general aspect of the present disclosure may include a system that may include a set of proximal guide pins. A system that may also include a set of distal guide pins. A system that may furthermore include a navigation guide having: a proximal end; a distal end; a body between the proximal end and the distal end, the body having: a superior side, an inferior side, a medial side, a lateral side, a proximal side, and a distal side; a set of proximal bone attachment features configured to identify a location for a proximal reference feature on a cuneiform of the patient's foot that corresponds to a proximal model reference on a cuneiform model of the cuneiform and to receive the set of proximal guide pins that serve as the proximal reference feature; a set of distal bone attachment features configured to identify a location for a distal reference feature on a metatarsal of the patient's foot that corresponds to a distal model reference on a metatarsal model of the metatarsal and to receive the set of distal guide pins that serve as the distal reference feature; where the set of proximal guide pins serve as a proximal resection guide anchor and as a proximal alignment feature and the set of distal guide pins serve as a distal resection guide anchor and as a distal alignment feature; a registration key on the inferior side of the body, the registration key having a protrusion that engages an opening between the cuneiform and the metatarsal of a tarsometatarsal (TMT) joint. A system that may in addition include a proximal resection guide configured to engage the set of proximal guide pins, the proximal resection guide having a cuneiform resection feature configure to guide resection of the cuneiform to form a cut face of the cuneiform for a correction of a condition present in a patient's foot. A system that may moreover include a distal resection guide configured to engage the set of distal guide pins, the distal resection guide having a metatarsal resection feature configure to guide resection of the metatarsal to form a cut face of the metatarsal for the correction of the condition present in the patient's foot. A system that may also include a positioning guide configured to engage the proximal alignment feature and the distal alignment feature as the positioning guide is deployed, the positioning guide configured to translate and rotate the metatarsal such that the cut face of the metatarsal contacts the cut face of the cuneiform.

Implementations may also include one or more of the following features. A system where the navigation guide may include a bone engagement surface configured to register to an anatomical structure of at least one of the cuneiform, the metatarsal, and the TMT joint, the bone engagement surface defined based on medical imaging taken of the metatarsal and the cuneiform of the patient's foot. A system where at least one of the navigation guide, the proximal resection guide, the distal resection guide, and the positioning guide may include a bone engagement surface configured to register to an anatomical structure of the patient's foot. A system where the navigation guide may include a coupler between the proximal end and the distal end of the navigation guide, the coupler having: a bolt having a head and a shaft, the head having a drive feature and the shaft having a set of threads on an external surface of the shaft; a head opening in one of the proximal end and the distal end configured to receive the head of the bolt; and a shaft opening in the other one of the proximal end and the distal end configured to receive the shaft of the bolt, the shaft opening having internal threads configured to engage the set of threads on the external surface of the shaft. A system where the navigation guide may include a plurality of sets of distal bone attachment features, each set of distal bone attachment features positioned radially about a long axis of the metatarsal at a different angle relative to the set of proximal bone attachment features. A system where the different angles differ by about 5 degrees relative to each other. A system where the positioning guide may include: a positioning guide body having: a set of proximal holes configured to accept and slide over the proximal alignment feature; a set of distal holes configured to accept and slide over the distal alignment feature; and where the set of proximal holes and the set of distal holes are positioned relative to each other such that as the positioning guide body moves towards the metatarsal and the cuneiform, one of the metatarsal and the cuneiform move and close an osteotomy of at least one of the metatarsal and the cuneiform. A system where the set of proximal holes and the set of distal holes are positioned in the positioning guide body such that moving the positioning guide body along the proximal alignment feature and distal alignment feature towards the metatarsal and the cuneiform compresses the cut face of the metatarsal against the cut face of the cuneiform.

One general aspect of the present disclosure may include a method that may include deploying a navigation guide onto a cuneiform and a metatarsal across a tarsometatarsal (TMT) joint of a patient, the navigation guide having: two proximal holes configured to accept and identify a location for two proximal guide pins that provide a proximal reference feature on the cuneiform for a proximal model reference on a cuneiform model of the cuneiform; two distal holes configured to accept and identify a location for two distal guide pins that provide a distal reference feature on the metatarsal for a distal model reference on a metatarsal model of the metatarsal; a coupler configured to connect the two proximal holes and the two distal holes across the TMT until an user operates the coupler to separate the two proximal holes and the two distal holes. A method that may also include deploying the two proximal guide pins into the two proximal holes and the two distal guide pins into the two distal holes. A method that may furthermore include operating the coupler to separate the two proximal holes and the two distal holes. A method that may in addition include removing the navigation guide. A method that may moreover include sliding a proximal resection guide over the two proximal guide pins until the proximal resection guide contacts the cuneiform, the proximal resection guide having a cuneiform resection feature configure to guide resection of the cuneiform. A method that may also include inserting a cutting tool into the cuneiform resection feature to create an osteotomy of the cuneiform. A method that may furthermore include sliding a distal resection guide over the two distal guide pins until the distal resection guide contacts the metatarsal, the distal resection guide having a metatarsal resection feature configure to guide resection of the metatarsal. A method that may in addition include inserting a cutting tool into the metatarsal resection feature to create an osteotomy of the metatarsal. A method that may moreover include sliding a positioning guide over the two proximal guide pins and the two distal guide pins until the positioning guide contacts the cuneiform and the metatarsal, where the positioning guide causes a cut face of the osteotomy of the cuneiform to contact a cut face of the osteotomy of the metatarsal. A method that may also include deploying fixation secured the cuneiform to the metatarsal.

Implementations may also include one or more of the following features. A method where the distal resection guide may include a first distal resection guide and where sliding the first distal resection guide further may include replacing the first distal resection guide with a second resection guide, the second resection guide configured to guide resection of the metatarsal at an angle that extends more distal from a proximal end of the metatarsal than the metatarsal resection feature of the first distal resection guide.

BRIEF DESCRIPTION OF THE DRAWINGS

The advantages, nature, and additional features of exemplary embodiments of the disclosure will become more fully apparent from the following description and appended claims, taken in conjunction with the accompanying drawings. Understanding that these drawings depict only exemplary embodiments and are, therefore, not to be considered limiting of the disclosure's scope, the exemplary embodiments of the disclosure will be described with additional specificity and detail through use of the accompanying drawings.

FIG. 4 illustrates an exemplary system configured to generate one or more patient-specific instruments, according to one embodiment.

FIG. 12A illustrates a top perspective view of a positioning guide from a medial side according to one embodiment.

FIG. 12B illustrates a bottom perspective view of a positioning guide according to one embodiment.

FIG. 12C illustrates a perspective view of a positioning guide from a lateral side according to one embodiment.

DETAILED DESCRIPTION

Figures 1A, 1B:
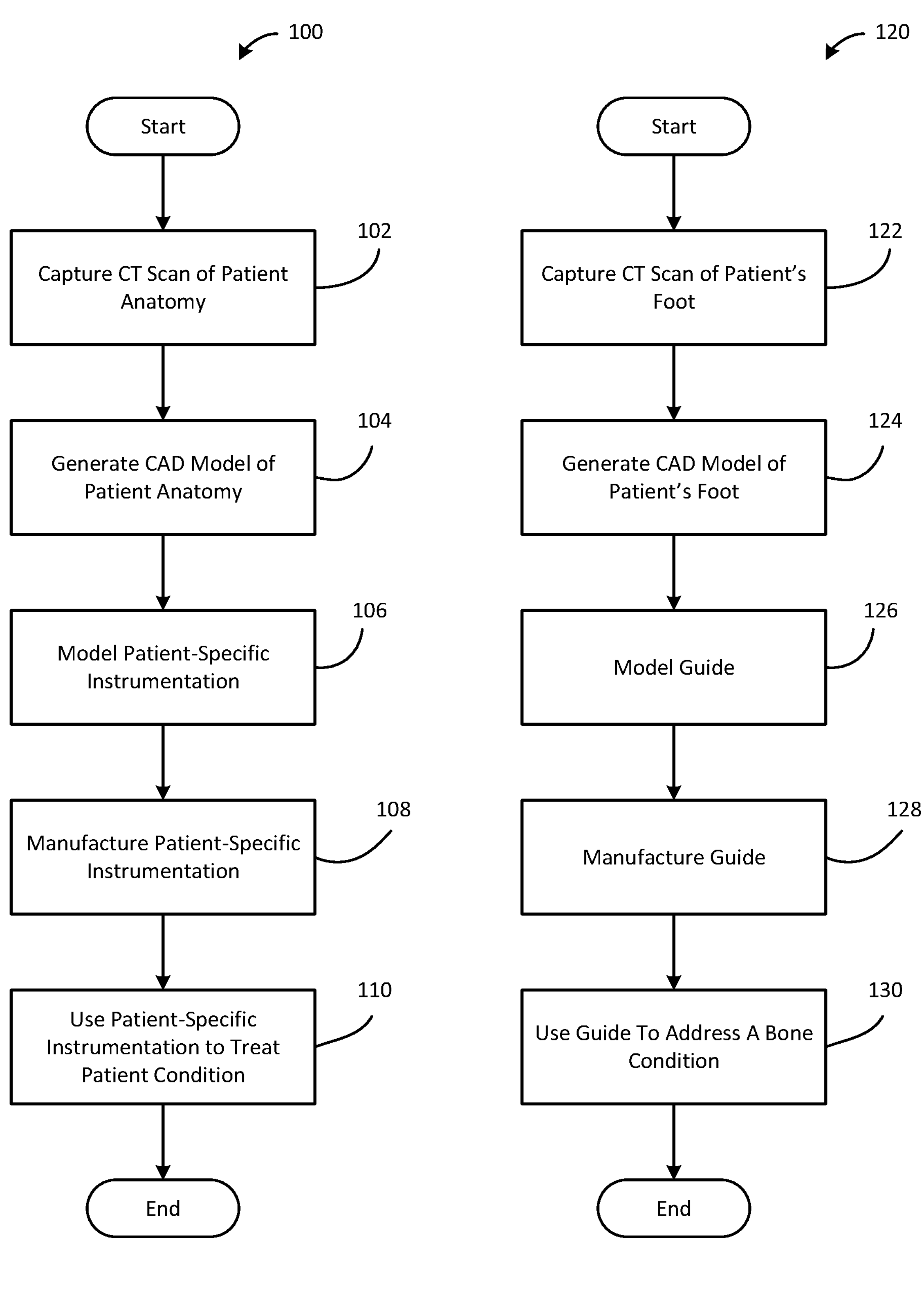
FIG. 1A is a flowchart diagram depicting a method for remediating a condition, according to one embodiment.
FIG. 1B is a flowchart diagram depicting a method for remediating a condition, according to one embodiment.

Exemplary embodiments of the disclosure will be best understood by reference to the drawings, wherein like parts are designated by like numerals throughout. It will be readily understood that the components, as generally described and illustrated in the Figures herein, could be arranged and designed in a wide variety of different configurations. Thus, the following more detailed description of the embodiments of the apparatus, system, and method is not intended to limit the scope of the disclosure but is merely representative of exemplary embodiments.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature can pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this disclosure. While these terms are commonly used to refer to the human body, certain terms are applicable to physical objects in general. A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body from the side which has a particular condition or structure. Proximal means toward the trunk of the body. Proximal may also mean toward a user, viewer, or operator. Distal means away from the trunk. Distal may also mean away from a user, viewer, or operator. Dorsal means toward the top of the foot or other body structure. Plantar means toward the sole of the foot or toward the bottom of the body structure.

Antegrade means forward moving from a proximal location/position to a distal location/position or moving in a forward direction. Retrograde means backward moving from a distal location/position to a proximal location/position or moving in a backwards direction. Sagittal refers to a midline of a patient's anatomy, which divides the body into left or right halves. The sagittal plane may be in the center of the body, splitting it into two halves. Prone means a body of a person lying face down. Supine means a body of a person lying face up.

As used herein, "coupling", "coupling member", or "coupler" refers to a mechanical device, apparatus, member, component, system, assembly, or structure, that is organized, configured, designed, arranged, or engineered to connect, or facilitate the connection of, two or more parts, objects, or structures. In certain embodiments, a coupling can connect adjacent parts or objects at their ends. In certain embodiments, a coupling can be used to connect two shafts together at their ends for the purpose of transmitting power. In other embodiments, a coupling can be used to join two pieces of rotating equipment while permitting some degree of misalignment or end movement or both. In certain embodiments, couplings may not allow disconnection of the two parts, such as shafts during operation. (Search "coupling" on Wikipedia.com Jul. 26, 2021. CC-BY-SA 3.0 Modified. Accessed Jul. 27, 2021.) A coupler may be flexible, semi-flexible, pliable, elastic, or rigid. A coupler may join two structures either directly by connecting directly to one structure and/or directly to the other or indirectly by connecting indirectly (by way of one or more intermediary structures) to one structure, to the other structure, or to both structures.

"Patient specific" refers to a feature, an attribute, a characteristic, a structure, function, structure, device, guide, tool, instrument, apparatus, member, component, system, assembly, module, or subsystem or the like that is adjusted, tailored, modified, organized, configured, designed, arranged, engineered, and/or fabricated to specifically address the anatomy, physiology, condition, abnormalities, needs, or desires of a particular patient or surgeon serving the particular patient. In one aspect, a patient specific attribute or feature is unique to a single patient and may include features unique to the patient such as a number of cut channels, a number of bone attachment features, a number of bone engagement surfaces, a number of resection features, a depth of one or more cutting channels, an angle for one or more resection channels, a surface contour, component position, component orientation, a trajectory for an instrument, implant, or anatomical part of a patient, a lateral offset, and/or other features.

"Patient-specific instrument" refers to an instrument, implant, or guide designed, engineered, and/or fabricated for use with a specific patient. In one aspect, a patient-specific instrument is unique to a patient and may include features unique to the patient such as a surface contour or other features.

"Patient-specific positioning guide" or "Patient-specific positioner" refers to an instrument, implant, positioner, structure, or guide designed, engineered, and/or fabricated for use as a positioner with a specific patient. In one aspect, a patient-specific positioning guide is unique to a patient and may include features unique to the patient such as patient-specific offsets, translation distances, openings, angles, orientations, anchor a surface contour or other features.

"Patient-specific cutting guide" refers to a cutting guide designed, engineered, and/or fabricated for use with a specific patient. In one aspect, a patient-specific cutting guide is unique to a patient and may include features unique to the patient such as a surface contour or other features.

"Patient-specific resection guide" refers to a guide designed, engineered, and/or fabricated for use in resection for a specific patient. In one aspect, a patient-specific resection guide is unique to a patient and may include features unique to the patient such as a surface contour or other features.

"Patient-specific trajectory guide" refers to a trajectory guide designed, engineered, and/or fabricated for use with a specific patient. In one aspect, a patient-specific trajectory guide is unique to a single patient and may include features unique to the patient such as a surface contour or other features.

"Patient specific instrument" (PSI) refers to a structure, device, guide, tool, instrument, apparatus, member, component, system, assembly, module, or subsystem that is adjusted, tailored, modified, organized, configured, designed, arranged, engineered, and/or fabricated to specifically address the anatomy, physiology, condition, abnormalities, needs, or desires of a particular patient. In certain aspects, one patient. In one aspect, a patient specific instrument is unique to a single patient and may include features unique to the patient such as a surface contour, component position, component orientation, and/or other features. In other aspects, one patient specific instrument may be useable with a number of patients having a particular class of characteristics.

As used herein, a "handle" or "knob" refers to a structure used to hold, control, or manipulate a device, apparatus, component, tool, or the like. A "handle" may be designed to be grasped and/or held using one or two hands of a user. In certain embodiments, a handle or knob may be an elongated structure. In one embodiment, a knob may be a shorter stubby structure.

As used herein, "implant" refers to a medical device manufactured to replace a missing biological structure, support a damaged biological structure, or enhance an existing biological structure. Often medical implants are man-made devices, but implants can also be natural occurring structures. The surface of implants that contact the body may be made of, or include a biomedical material such as titanium, cobalt chrome, stainless steel, carbon fiber, another metallic alloy, silicone, polymer, Synthetic polyvinyl alcohol (PVA) hydrogels, biomaterials, biocompatible polymers such as PolyEther Ether Ketone (PEEK) or a polylactide polymer (e.g. PLLA) and/or others, or apatite, or any combination of these depending on what is functional and/or economical. Implants can have a variety of configurations and can be wholly, partially, and/or include a number of components that are flexible, semiflexible, pliable, elastic, supple, semi-rigid, or rigid. In some cases implants contain electronics, e.g. artificial pacemaker and cochlear implants. Some implants are bioactive, such as subcutaneous drug delivery devices in the form of implantable pills or drug-eluting stents. Orthopedic implants may be used to alleviate issues with bones and/or joints of a patient's body. Orthopedic implants can be used to treat bone fractures, osteoarthritis, scoliosis, spinal stenosis, discomfort, and pain. Examples of orthopedic implants include, but are not limited to, a wide variety of pins, rods, screws, anchors, spacers, sutures, all-suture implants, ball all-suture implants, self-locking suture implants, cross-threaded suture implants, plates used to anchor fractured bones while the bones heal or fuse together, and the like. (Search "implant (medicine)" on Wikipedia.com May 26, 2021. CC-BY-SA 3.0 Modified. Accessed Jun. 30, 2021.)

As used herein, a "body" refers to a main or central part of a structure. The body may serve as a structural component to connect, interconnect, surround, enclose, and/or protect one or more other structural components. A body may be made from a variety of materials including, but not limited to, metal, plastic, ceramic, wood, fiberglass, acrylic, carbon, biocompatible materials, biodegradable materials or the like. A body may be formed of any biocompatible materials, including but not limited to biocompatible metals such as Titanium, Titanium alloys, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others. In one embodiment, a body may include a housing or frame or framework for a larger system, component, structure, or device. A body may include a modifier that identifies a particular function, location, orientation, operation, and/or a particular structure relating to the body. Examples of such modifiers applied to a body, include, but are not limited to, "inferior body," "superior body," "lateral body," "medial body," and the like.

As used herein, "bone engagement surface" refers to a surface of an object, instrument, or apparatus, such as an implant that is oriented toward or faces one or more bones of a patient. In one aspect, the bone engagement surface may abut, touch, or contact a surface of a bone. In another aspect, the bone engagement surface or parts of the bone engagement surface may be close to, but not abut, touch, or contact a surface of the bone. In certain aspects, the bone engagement surface can be configured to engage with a surface of one or more bones. Such a bone engagement surface may include projections and recesses that correspond to and match projections and recesses of the one or more bone surfaces.

"Frangible" refers to a type of material designed, engineered, and/or configured to break easily under an expected force. Frangible objects may be designed to break easily under the expected force to provide a safety feature, a convenience feature, or the like. Frangible objects can be made from metal, plastic, ceramics, wood, paper, or the like. Frangible also includes something that is breakable or fragile; especially something that is intentionally made so. (Search "frangible" on wordhippo.com. WordHippo, 2023. Web. Accessed 11 May 2023. Modified.)

As used herein, "side" refers to a structure or part of a structure including, but not limited to: one of a longer bounding surfaces or lines of an object especially contrasted with the ends, a line or surface forming a border or face of an object, either surface of a thin object, a bounding line or structure of a geometric figure or shape, and the like. (search "side" on Merriam-Webster.com. Merriam-Webster, 2021. Web. 3 Aug. 2021. Modified.) A side can also refer to a geometric edge of a polygon (two-dimensional shape) and/or a face or surface of a polyhedron (three-dimensional shape). (Search "side" on Wikipedia.com Jul. 21, 2021. CC-BY-SA 3.0 Modified. Accessed Aug. 3, 2021.) Side can also refer to a location on a structure. For example, a side can be a location on a structure at, or near, a furthest position away from a central axis of the structure. As used herein, the term "side" can include one or more modifiers that define and/or orient and/or distinguish the side of an object from others based on based on where and/or how the object is deployed within or in relation to a second object. For example, in the context of an implant for a patient, sides of the implant may be labeled based on where the sides are relative to the patient when the implant is deployed. As one example, an "anterior side" of an implant refers to a side that is anterior to other sides of the implant in relation to a patient when the implant is deployed in the patient. As another example, in the context of an instrument used with a patient, sides of the instrument may be labeled based on where the sides are when the instrument is being used for its purpose. As one example, a "front side" of an instrument refers to a side that is facing a user of the instrument when the instrument is in use.

As used herein, a "deploy" or "deployment" refers to an act, action, process, system, method, means, or apparatus for inserting an implant or prosthesis into a part, body part, and/or patient. "Deploy" or "deployment" can also refer to an act, action, process, system, method, means, or apparatus for placing something into therapeutic use. A device, system, component, medication, drug, compound, or nutrient may be deployed by a human operator, a mechanical device, an automated system, a computer system or program, a robotic system, or the like.

"Joint" or "Articulation" refers to the connection made between bones in a human or animal body which link the skeletal system to form a functional whole. Joints may be biomechanically classified as a simple joint, a compound joint, or a complex joint. Joints may be classified anatomically into groups such as joints of hand, elbow joints, wrist joints, axillary joints, sternoclavicular joints, vertebral articulations, temporomandibular joints, sacroiliac joints, hip joints, knee joints, articulations of foot, and the like. (Search "joint" on Wikipedia.com Dec. 19, 2021. CC-BY-SA 3.0 Modified. Accessed Jan. 20, 2022.)

"Topographical" refers to the physical distribution of parts, structures, or features on the surface of, or within, an organ or other anatomical structure, or organism. (Search "define topographical" on google.com. Oxford Languages, Copyright 2022. Oxford University Press. Web., Modified. Accessed 15 Feb. 2022.)

"Landmark registration features" or "Landmark" refers to a structure configured to engage with a feature, aspect, attribute, or characteristic of a first object to orient and/or position a second object that includes the landmark registration feature with respect to the first object. A variety of structures can serve as a landmark registration feature. For example, a landmark registration feature may include a protrusion, a projection, a tuberosity, a cavity, a void, a divot, a tab, an extension, a hook, a curve, or the like. In the context of bones of a patient a landmark registration feature can include any protuberance, void, divot, concave section, sesamoid, bone spur or other feature on, or extending from, a bone of a patient.

"Probe bone engagement surface" refers to a bone engagement surface on one surface of a probe or part of a probe.

"Bone attachment feature" refers to a structure, feature, component, aspect configured to securely connect, couple, attach, and/or engage a structure, component, object, or body with a bone and/or a bone fragment. Examples of a bone attachment feature, include, but are not limited to, a pin, K-wire, screw, or other fastener alone, or in combination with, a hole, passage, and/or opening.

As used herein, "patient-specific osteotomy procedure" refers to an osteotomy procedure that has been adjusted, tailored, modified, or configured to specifically address the needs or desires or a particular patient. In certain aspects, one patient-specific osteotomy procedure may be useable in connection with only one patient. In other aspects, one patient-specific osteotomy procedure may be useable with a number of patients having a particular class of characteristics.

As used herein, a "stop" refers to an apparatus, instrument, structure, member, device, component, system, or assembly structured, organized, configured, designed, arranged, or engineered to prevent, limit, impede, stop, or restrict motion or movement and/or operation of the another object, member, structure, component, part, apparatus, system, or assembly.

As used herein, a “fastener”, “fixation device”, or “fastener system” refers to any structure configured, designed, or engineered to join two structures. Fasteners may be made of a variety of materials including metal, plastic, composite materials, metal alloys, plastic composites, and the like. Examples of fasteners include, but are not limited to screws, rivets, bolts, nails, snaps, hook and loop, set screws, bone screws, nuts, posts, pins, thumb screws, and the like. Other examples of fasteners include, but are not limited to wires, Kirschner wires (K-wire), anchors, bone anchors, plates, bone plates, intramedullary nails or rods or pins, implants, sutures, soft sutures, soft anchors, tethers, interbody cages, fusion cages, and the like.

In certain embodiments, the term fastener may refer to a fastener system that includes two or more structures configured to combine to serve as a fastener. An example of a fastener system is a rod or shaft having external threads and an opening or bore within another structure having corresponding internal threads configured to engage the external threads of the rod or shaft.

In certain embodiments, the term fastener may be used with an adjective that identifies an object or structure that the fastener may be particularly configured, designed, or engineered to engage, connect to, join, contact, or couple together with one or more other structures of the same or different types. For example, a “bone fastener” may refer to an apparatus for joining or connecting one or more bones, one or more bone portions, soft tissue and a bone or bone portion, hard tissue and a bone or bone portion, an apparatus and a bone or portion of bone, or the like.

In certain embodiments, a fastener may be a temporary fastener. A temporary fastener is configured to engage and serve a fastening function for a relatively short period of time. Typically, a temporary fastener is configured to be used until another procedure or operation is completed and/or until a particular event. In certain embodiments, a user may remove or disengage a temporary fastener. Alternatively, or in addition, another structure, event, or machine may cause the temporary fastener to become disengaged.

As used herein, a “fixator” refers to an apparatus, instrument, structure, device, component, member, system, assembly, or module structured, organized, configured, designed, arranged, or engineered to connect two bones or bone fragments or a single bone or bone fragment and another fixator to position and retain the bone or bone fragments in a desired position and/or orientation. Examples of fixators include both those for external fixation as well as those for internal fixation and include, but are not limited to pins, wires, Kirschner wires, screws, anchors, bone anchors, plates, bone plates, intramedullary nails or rods or pins, implants, interbody cages, fusion cages, and the like. Fixation refers to the act of deploying or using a fixator to fix two structures together.

As used herein, an “anchor” refers to an apparatus, instrument, structure, member, part, device, component, system, or assembly structured, organized, configured, designed, arranged, or engineered to secure, retain, stop, and/or hold, an object to or at a fixed point, position, or location. Often, an anchor is coupled and/or connected to a flexible member such as a tether, chain, rope, wire, thread, suture, suture tape, or other like object. Alternatively, or in addition, an anchor may also be coupled, connected, and/or joined to a rigid object or structure. In certain embodiments, an anchor can be a fixation device. Said another way, a fixation device can function as an anchor. In certain embodiments, the term anchor may be used as an adjective that describes a function, feature, or purpose for the noun the adjective ‘anchor’ describes. For example, an anchor hole is a hole that serves as or can be used as an anchor.

“Connector” refers to any structure configured, engineered, designed, adapted, and/or arranged to connect one structure, component, element, or apparatus to another structure, component, element, or apparatus. A connector can be rigid, pliable, elastic, flexible, and/or semiflexible. Examples of a connector include but are not limited to any fastener.

“Clearance” refers to a space or opening that provides an unobstructed area to permit one object to move freely in relation to another object.

“Correction,” in a medical context, refers to a process, procedure, device, instrument, apparatus, system, implant, or the like that is configured, designed, developed, fabricated, configured, and/or organized to adjust, translate, move, orient, rotate, or otherwise change an anatomical structure from an original position, location, and/or orientation to a new position, location, and/or orientation that provides a benefit to a patient. The benefit may be one of appearance, anatomical function, pain relief, increased mobility, increased strength, and the like.

“Uniplanar correction” refers to a medical correction, which can include an osteo correction, in one plane (e.g., one of a sagittal plane, a transverse plane, and a coronal/frontal plane) of an anatomical structure such as a foot, hand, or body of a patient.

“Biplanar correction” refers to a medical correction, which can include an osteo correction, in two planes (e.g., two of a sagittal plane, a transverse plane, and a coronal/frontal plane) of an anatomical structure such as a foot, hand, or body of a patient.

“Triplane correction” refers to a medical correction, which can include an osteo correction, in three planes (e.g., all three planes of a sagittal plane, a transverse plane, and a coronal/frontal plane) of an anatomical structure such as a foot, hand, or body of a patient.

“Probe” refers to a medical instrument used to explore, identify, locate, or register to, wounds, organs, and/or anatomical structures including a joint or an articular surface. In certain embodiments, a probe can be thin and/or pointed. In one embodiment, a probe is connected, integrated with, and/or coupled to another structure or instrument. In such an embodiment, the probe may serve to facilitate proper positioning of the another structure or instrument. For example, the probe may be used to identify and/or locate a particular anatomical structure and the positioning of the probe may then cause the connected structure or instrument to also be positioned in a desired location relative to one or more anatomical structures.

As used herein, “manufacturing tool” or “fabrication tool” refers to a manufacturing or fabrication process, tool, system, or apparatus which creates an object, device, apparatus, feature, or component using one or more source materials. A manufacturing tool or fabrication tool can use a variety of manufacturing processes, including but not limited to additive manufacturing, subtractive manufacturing, forging, casting, and the like. The manufacturing tool can use a variety of materials including polymers, thermoplastics, metals, biocompatible materials, biodegradable materials, ceramics, biochemicals, and the like. A manufacturing tool may be operated manually by an operator, automatically using a computer numerical controller (CNC), or a combination of these techniques.

"Friction fit" refers to a type of joint or connection that is created between two components by means of friction. A joint or connection that is formed using a friction fit may or may not include the use of additional fasteners such as screws, bolts, or adhesives. In a friction fit, the components are designed or configured to fit tightly together, creating enough friction between the surfaces to hold them securely in place, at least temporarily. The friction force is generated by the compressive force that is experienced between the components, and can be strong enough to prevent the components from separating under normal conditions. (© ChatGPT March 23 Version, Modified, accessed chat.openai.com/chat May 2, 2023).

As used herein, "osteotomy procedure" or "surgical osteotomy" or "osteotomy" refers to a surgical operation in which one or more bones are cut to shorten or lengthen them or to change their alignment. The procedure can include removing one or more portions of bone and/or adding one or more portions of bone or bone substitutes. (Search "osteotomy" on Wikipedia.com Feb. 3, 22, 2021. CC-BY-SA 3.0 Modified. Accessed Feb. 15, 2022.) As used herein, "patient-specific osteotomy procedure" refers to an osteotomy procedure that has been adjusted, tailored, modified, or configured to specifically address the anatomy, physiology, condition, abnormalities, needs, or desires of a particular patient. In certain aspects, one patient-specific osteotomy procedure may be useable in connection with only one patient. In other aspects, one patient-specific osteotomy procedure may be useable with a number of patients having a particular class of characteristics. In certain aspects, a patient-specific osteotomy procedure may refer to a non-patient-specific osteotomy procedure that includes one or more patient-specific implants and/or instrumentation. In another aspects, a patient-specific osteotomy procedure may refer to a patient-specific osteotomy procedure that includes one or more patient-specific implants, patient-specific surgical steps, and/or patient-specific instrumentation.

"Wedge osteotomy" refers to an osteotomy procedure in which one or more wedges are used as part of the procedure. Generally, wedge osteotomies can be of one of two types, open wedge and closing wedge. The type of osteotomy refers to how the procedure changes the relation between two parts of a bone involved in the osteotomy. In an open wedge osteotomy a wedge of bone or graft or other material is inserted in between two parts of a bone. Consequently, a wedge shape is "opened" in the bone. In a close wedge osteotomy or closing wedge osteotomy a wedge of bone is removed from a bone. Consequently, a wedge shape formed in the bone is "closed."

"Metatarsal" is a bone of a foot of a human or animal. In a human, a foot typically includes five metatarsals which are identified by number starting from the most medial metatarsal, which is referred to as a first metatarsal and moving laterally the next metatarsal is the second metatarsal, and the naming continues in like manner for the third, fourth, and fifth metatarsal. The metatarsal bone includes three parts a base which is a part that is at a proximal end of the metatarsal, a head which is a part that is at a distal end of the metatarsal, and a shaft or neck connects the base to the head.

"Epiphyses" refers to the rounded end of a long bone, at long bone's joint with adjacent bone(s). Between the epiphysis and diaphysis (the long midsection of the long bone) lies the metaphysis, including the epiphyseal plate (growth plate). At the joint, the epiphysis is covered with articular cartilage; below that covering is a zone similar to the epiphyseal plate, known as subchondral bone. (Search 'epiphysis' on Wikipedia.com 17 Jun. 2022. Modified. Accessed Aug. 1, 2022.) "Metaphysis" refers to the neck portion of a long bone between the epiphysis and the diaphysis. The metaphysis contains the growth plate, the part of the bone that grows during childhood, and as the metaphysis grows the metaphysis ossifies near the diaphysis and the epiphyses. (Search 'metaphysis' on Wikipedia.com 17 Jun. 2022. Modified. Accessed Aug. 1, 2022.) "Diaphysis" refers to the main or midsection (shaft) of a long bone. The diaphysis is made up of cortical bone and usually contains bone marrow and adipose tissue (fat). The diaphysis is a middle tubular part composed of compact bone which surrounds a central marrow cavity which contains red or yellow marrow. In diaphysis, primary ossification occurs. (Search 'diaphysis' on Wikipedia.com 17 Jun. 2022. Modified. Accessed Aug. 1, 2022.)

"Metaphyseal Diaphyseal Junction" or "MDJ" refers to an area of a long bone between the Metaphysis and the Diaphysis. This area can also include or be referred to as the epiphyseal plate (growth) plate. For certain surgical procedures, performing an osteotomy at or near the metaphyseal diaphyseal junction may be advantageous and desirable to promote rapid fusion of two cut faces formed in the osteotomy and bone growth to close the osteotomy, and/or may mitigate the risk of a nonunion of the osteotomy.

As used herein, a "base" refers to a main or central structure, component, or part of a structure. A base is often a structure, component, or part upon which, or from which other structures extend into, out of, away from, are coupled to, or connect to. A base may have a variety of geometric shapes and configurations. A base may be rigid or pliable. A base may be solid or hollow. A base can have any number of sides. In one embodiment, a base may include a housing, frame, or framework for a larger system, component, structure, or device. In certain embodiments, a base can be a part at the bottom or underneath a structure designed to extend vertically when the structure is in a desired configuration or position. Certain bones such as a metatarsal bone can include a base as one structural component of the bone.

As used herein, "anatomic data" refers to data identified, used, collected, gathered, and/or generated in connection with an anatomy of a human or animal. Examples of anatomic data may include location data for structures, both independent, and those connected to other structures within a coordinate system. Anatomic data may also include data that labels or identifies one or more anatomical structures. Anatomic data can include volumetric data, material composition data, and/or the like. Anatomic data can be generated based on medical imaging data or measurements using a variety of instruments including monitors and/or sensors. Anatomic data can be gathered, measured, or collected from anatomical models and/or can be used to generate, manipulate, or modify anatomical models.

A bone model or anatomic model of a patient's body or body part(s) may be generated by computing devices that analyze medical imaging images. Structures of a patient's body can be determined using a process called segmentation.

"Positioner" or "positioning guide" refers to any structure, apparatus, surface, device, system, feature, or aspect configured to position, move, translate, manipulate, or arrange one object in relation to another. In certain embodiments, a positioner can be used for one step in surgical procedure to position, arrange, orient, and/or reduce one bone or bone fragment relative to another. In such embodiments, the positioner may be referred to as a bone positioner. In certain embodiments, the term positioner or positioning guide may be preceded by an adjective that identifies the structure, implement, component, or instrument that may be used with, positioned by, and/or guided by with the positioner. For example, a "pin positioner" may be configured to accept a pin or wire such as a K-wire and serve to position or place the pin relative to another structure such as a bone.

"Reduction guide" or "reducer" refers to any structure, apparatus, surface, device, system, feature, or aspect configured, designed, engineered, or fabricated to reduce or aide a user in the reduction of one bone or bone fragment or implant in relation to another bone or bone fragment or implant.

"Rotation guide" or "rotator" refers to any structure, apparatus, surface, device, system, feature, or aspect configured, designed, engineered, or fabricated to rotate or aid a user in the rotation of one structure relative to another structure. In certain embodiments, a rotation guide or rotator may be used to help a surgeon rotate one or more bones, parts of bones, bone fragment, an implant, or other anatomical structure, either alone or in relation to another one or more bones, parts of bones, bone fragments, implants, or other anatomical structures.

"Trajectory guide" or "trajectory indicator" or "targeting guide" refers to any structure, apparatus, surface, device, system, feature, or aspect configured to indicate, identify, guide, place, position, or otherwise assist in marking or deploying a fastener or other structure along a desired trajectory for one or more subsequent steps in a procedure.

"Metatarsal base resection guide" refers to a resection guide designed, engineered, fabricated, or intended for use with, one, in, or about a base part, section, surface, portion, or aspect of a metatarsal for one or more steps of a medical procedure. The metatarsal base resection guide may be used to form an osteotomy, to resect a wedge for a closing wedge procedure, resect a bone wedge that preserves a cortical layer of bone opposite the resected bone wedge, form an osteotomy that uniplanar wedge, a biplanar wedge, or a triplane wedge. Various embodiments of a metatarsal base resection guide may be used on a medial surface, a dorsal surface, a lateral surface, or a plantar surface of a single metatarsal. Alternatively, or in addition, various embodiments of a metatarsal base resection guide can be used on two or more metatarsals.

As used herein, a "guard" refers to an apparatus, instrument, structure, member, device, component, system, or assembly structured, organized, configured, designed, arranged, or engineered to prevent, limit, impede, stop, or restrict motion, action, or movement and/or operation of the another object, member, structure, component, part, apparatus, system, or assembly beyond a certain parameter such as a boundary. Said another way, a "guard" refers to an apparatus, instrument, structure, member, device, component, system, or assembly structured, organized, configured, designed, arranged, or engineered to retain, maintain, hold, keep, or restrict motion, action, or movement and/or operation of the another object, member, structure, component, part, apparatus, system, or assembly within or at one or more parameters such as a boundary.

As used herein, "artificial intelligence" refers to intelligence demonstrated by machines, unlike the natural intelligence displayed by humans and animals, which involves consciousness and emotionality. The distinction between artificial intelligence and natural intelligence categories is often revealed by the acronym chosen. 'Strong' AI is usually labelled as artificial general intelligence (AGI) while attempts to emulate 'natural' intelligence have been called artificial biological intelligence (ABI). Leading AI textbooks define the field as the study of "intelligent agents": any device that perceives its environment and takes actions that maximize its chance of achieving its goals. The term "artificial intelligence" can also be used to describe machines that mimic "cognitive" functions that humans associate with the human mind, such as "learning" and "problem solving". (Search "artificial intelligence" on Wikipedia.com Jun. 25, 2021. CC-BY-SA 3.0 Modified. Accessed Jun. 25, 2021.)

As used herein, "segmentation" or "image segmentation" refers to the process of partitioning an image into different meaningful segments. These segments may correspond to different tissue classes, organs, pathologies, bones, or other biologically relevant structures. Medical image segmentation accommodates imaging ambiguities such as by low contrast, noise, and other imaging ambiguities.

Certain computer vision techniques can be used or adapted for image segmentation. For example, the techniques and or algorithms for segmentation may include, but are not limited to: Atlas-Based Segmentation: For many applications, a clinical expert can manually label several images; segmenting unseen images is a matter of extrapolating from these manually labeled training images. Methods of this style are typically referred to as atlas-based segmentation methods. Parametric atlas methods typically combine these training images into a single atlas image, while nonparametric atlas methods typically use all of the training images separately. Atlas-based methods usually require the use of image registration in order to align the atlas image or images to a new, unseen image.

Image registration is a process of correctly aligning images; Shape-Based Segmentation: Many methods parametrize a template shape for a given structure, often relying on control points along the boundary. The entire shape is then deformed to match a new image. Two of the most common shape-based techniques are Active Shape Models and Active Appearance Models; Image-Based Segmentation: Some methods initiate a template and refine its shape according to the image data while minimizing integral error measures, like the Active contour model and its variations; Interactive Segmentation: Interactive methods are useful when clinicians can provide some information, such as a seed region or rough outline of the region to segment. An algorithm can then iteratively refine such a segmentation, with or without guidance from the clinician. Manual segmentation, using tools such as a paint brush to explicitly define the tissue class of each pixel, remains the gold standard for many imaging applications. Recently, principles from feedback control theory have been incorporated into segmentation, which give the user much greater flexibility and allow for the automatic correction of errors; Subjective surface Segmentation: This method is based on the idea of evolution of segmentation function which is governed by an advection-diffusion model. To segment an object, a segmentation seed is needed (that is the starting point that determines the approximate position of the object in the image). Consequently, an initial segmentation function is constructed. With the subjective surface method, the position of the seed is the main factor determining the form of this segmentation function; and Hybrid segmentation which is based on combination of methods. (Search "medical image computing" on Wikipedia.com Jun. 24, 2021. CC-BY-SA 3.0 Modified. Accessed Jun. 24, 2021.)

As used herein, "medical imaging" refers to a technique and process of imaging the interior of a body for clinical analysis and medical intervention, as well as visual representation of the function of some organs or tissues (physiology). Medical imaging seeks to reveal internal structures hidden by the skin and bones, as well as to diagnose and treat disease. Medical imaging may be used to establish a database of normal anatomy and physiology to make possible identification of abnormalities. Medical imaging in its widest sense, is part of biological imaging and incorporates radiology, which uses the imaging technologies of X-ray radiography, magnetic resonance imaging, ultrasound, endoscopy, elastography, tactile imaging, thermography, medical photography, nuclear medicine functional imaging techniques as positron emission tomography (PET) and single-photon emission computed tomography (SPECT). Another form of X-ray radiography includes computerized tomography (CT) scans in which a computer controls the position of the X-ray sources and detectors. Magnetic Resonance Imaging (MRI) is another medical imaging technology. Measurement and recording techniques that are not primarily designed to produce images, such as electroencephalography (EEG), magnetoencephalography (MEG), electrocardiography (ECG), and others, represent other technologies that produce data susceptible to representation as a parameter graph vs. time or maps that contain data about the measurement locations. In certain embodiments bone imaging includes devices that scan and gather bone density anatomic data. These technologies may be considered forms of medical imaging in certain disciplines. (Search "medical imaging" on Wikipedia.com Jun. 16, 2021. CC-BY-SA 3.0 Modified. Accessed Jun. 23, 2021.) Data, including images, text, and other data associated with medical imaging is referred to as patient imaging data. As used herein, "patient imaging data" refers to data identified, used, collected, gathered, and/or generated in connection with medical imaging and/or medical imaging data. Patient imaging data can be shared between users, systems, patients, and professionals using a common data format referred to as Digital Imaging and Communications in Medicine (DICOM) data. DICOM data is a standard format for storing, viewing, retrieving, and sharing medical images.

As used herein, "medical image computing" or "medical image processing" refers to systems, software, hardware, components, and/or apparatus that involve and combine the fields of computer science, information engineering, electrical engineering, physics, mathematics and medicine. Medical image computing develops computational and mathematical methods for working with medical images and their use for biomedical research and clinical care. One goal for medical image computing is to extract clinically relevant information or knowledge from medical images. While closely related to the field of medical imaging, medical image computing focuses on the computational analysis of the images, not their acquisition. The methods can be grouped into several broad categories: image segmentation, image registration, image-based physiological modeling, and others. (Search "medical image computing" on Wikipedia.com Jun. 24, 2021. CC-BY-SA 3.0 Modified. Accessed Jun. 24, 2021.) Medical image computing may include one or more processors or controllers on one or more computing devices. Such processors or controllers may be referred to herein as medical image processors. Medical imaging and medical image computing together can provide systems and methods to image, quantify and fuse both structural and functional information about a patient in vivo. These two technologies include the transformation of computational models to represent specific subjects/patients, thus paving the way for personalized computational models. Individualization of generic computational models through imaging can be realized in three complementary directions: definition of the subject-specific computational domain (anatomy) and related subdomains (tissue types); definition of boundary and initial conditions from (dynamic and/or functional) imaging; and characterization of structural and functional tissue properties. Medical imaging and medical image computing enable the translation of models to the clinical setting with both diagnostic and therapeutic applications. (Id.) In certain embodiments, medical image computing can be used to generate a bone model, a patient-specific model, and/or a patent specific instrument from medical imaging and/or medical imaging data.

As used herein, "model" refers to an informative representation of an object, person or system. Representational models can be broadly divided into the concrete (e.g. physical form) and the abstract (e.g. behavioral patterns, especially as expressed in mathematical form). In abstract form, certain models may be based on data used in a computer system or software program to represent the model. Such models can be referred to as computer models. Computer models can be used to display the model, modify the model, print the model (either on a 2D medium or using a 3D printer or additive manufacturing technology). Computer models can also be used in environments with models of other objects, people, or systems. Computer models can also be used to generate simulations, display in virtual environment systems, display in augmented reality systems, or the like. Computer models can be used in Computer Aided Design (CAD) and/or Computer Aided Manufacturing (CAM) systems. Certain models may be identified with an adjective that identifies the object, person, or system the model represents. For example, a "bone" model is a model of a bone, and a "heart" model is a model of a heart. (Search "model" on Wikipedia.com Jun. 13, 2021. CC-BY-SA 3.0 Modified. Accessed Jun. 23, 2021.) As used herein, "additive manufacturing" refers to a manufacturing process in which materials are joined together in a process that repeatedly builds one layer on top of another to generate a three-dimensional structure or object. Additive manufacturing may also be referred to using different terms including: additive processes, additive fabrication, additive techniques, additive layer manufacturing, layer manufacturing, freeform fabrication, ASTM F2792 (American Society for Testing and Materials), and 3D printing. Additive manufacturing can build the three-dimensional structure or object using computer-controlled equipment that applies successive layers of the material(s) based on a three-dimensional model that may be defined using Computer Aided Design (CAD) software. Additive manufacturing can use a variety of materials including polymers, thermoplastics, metals, ceramics, biochemicals, and the like. Additive manufacturing may provide unique benefits, as an implant together with the pores and/or lattices can be directly manufactured (without the need to generate molds, tool paths, perform any milling, and/or other manufacturing steps).

"Repository" refers to any data source or dataset that includes data or content. In one embodiment, a repository resides on a computing device. In another embodiment, a repository resides on a remote computing or remote storage device. A repository may comprise a file, a folder, a directory, a set of files, a set of folders, a set of directories, a database, an application, a software application, content of a text, content of an email, content of a calendar entry, and the like. A repository, in one embodiment, comprises unstructured data. A repository, in one embodiment, comprises structured data such as a table, an array, a queue, a look up table, a hash table, a heap, a stack, or the like. A repository may store data in any format including binary, text, encrypted, unencrypted, a proprietary format, or the like.

"Reference" refers to any apparatus, structure, device, system, component, marking, and/or indicator organized, configured, designed, engineered, and/or arranged to serve as a source of information or a point of comparison used to support or establish knowledge, truth, or quality. (© ChatGPT January 9 Version, Modified, accessed chat.openai.com/chat Jan. 28, 2023). In certain embodiments, a reference can serve as a starting point or initial position for one or more steps in a surgical procedure. A reference may be a type of fiducial. In certain embodiments, "reference" can be with a an adjective describing the reference. For example, a "model reference" is a reference within a model such as a computer model. A model reference refers to any feature, aspect, and/or component within a model. Examples of a model reference include, but are not limited to, a point, a plane, a line, a plurality of points, a surface, an anatomical structure, a shape, or the like. An "anatomical reference" is a reference within, on, near, or otherwise associated with an anatomical structure such as a bone. A reference (e.g., model, actual, virtual, and/or real) may also be referred to as a reference feature.

"Reference feature" refers to a feature configured for use as a point, plane, axis, or line of reference (aka a reference). A reference or reference feature can be used to position, measure, orient, fixation, couple, engage, and/or align one object or structure with another object or structure. In certain embodiments, a reference or reference feature can serve as a baseline, a ground truth, a waypoint, a control point, a landmark, and/or the like. A reference feature can facilitate moving from one coordinate system or frame of reference in a virtual environment to a position, location, frame of reference, environment, or orientation on, or in, an actual object, structure, device, apparatus, anatomical structure, or the like. Advantageously, a reference feature can coordinate objects, models, or structures in a digital or virtual model or representation with corresponding objects or structures (e.g., anatomical structures) of actual physical objects or structures. Said another way, a reference feature can serve to map from a virtual or modeled object to an actual or physical object. As used herein, "feature" refers to a distinctive attribute or aspect of something. (Search "feature" on google.com. Oxford Languages, 2021. Web. 20 Apr. 2021.) A feature may include one or more apparatuses, structures, objects, systems, sub-systems, devices, or the like. A feature may include a modifier that identifies a particular function or operation and/or a particular structure relating to the feature. Examples of such modifiers applied to a feature, include, but are not limited to, "attachment feature," "alignment feature," "securing feature," "placement feature," "protruding feature," "engagement feature," "disengagement feature," "resection feature", "guide feature", "alignment feature," and the like.

As used herein, a "marking" or "marker" refers to a symbol, letter, lettering, word, phrase, icon, design, color, diagram, indicator, figure, structure, device, apparatus, surface, component, system, or combination of these designed, intended, structured, organized, configured, programmed, arranged, or engineered to communication information and/or a message to a user receiving, viewing, or encountering the marking. The marking or "marker" can include one or more of a tactile signal, a visual signal or indication, an audible signal, and the like. In one embodiment, a marking may comprise a number or set letters, symbols, or words positioned on a surface, structure, color, color scheme, or device to convey a desired message or set of information.

"Set" refers to a collection of objects. A set can have zero or more objects in the collection. Generally, a set includes one or more objects in the collection.

As used herein, a "sleeve" refers to structure that is narrow and longer longitudinally than the structure is wide. In certain embodiments, a sleeve serves to surround, enclose, wrap, and/or contain something else. In certain embodiments, a sleeve may surround, enclose, wrap, and/or contain a passage or void. (Search "sleeve" on wordhippo.com. WordHippo, 2021. Web. Accessed 15 Nov. 2021. Modified.) In certain embodiments, the term sleeve may be preceded by an adjective that identifies the structure, implement, component or instrument that may be used with, inserted into or associated with the sleeve. For example, a "pin sleeve" may be configured to accept a pin or wire such as a K-wire, a "drive sleeve" may be configured to accept a drill or drill bit, a "fixation member sleeve" may be configured to accept a fastener or fixation member.

As used herein, "image registration" refers to a method, process, module, component, apparatus, and/or system that seeks to achieve precision in the alignment of two images. As used here, "image" may refer to either or both an image of a structure or object and another image or a model (e.g., a computer based model or a physical model, in either two dimensions or three dimensions). In the simplest case of image registration, two images are aligned. One image may serve as the target image and the other as a source image; the source image is transformed, positioned, realigned, and/or modified to match the target image. An optimization procedure may be applied that updates the transformation of the source image based on a similarity value that evaluates the current quality of the alignment. An iterative procedure of optimization may be repeated until a (local) optimum is found. An example is the registration of CT and PET images to combine structural and metabolic information. Image registration can be used in a variety of medical applications: Studying temporal changes; Longitudinal studies may acquire images over several months or years to study long-term processes, such as disease progression. Time series correspond to images acquired within the same session (seconds or minutes). Time series images can be used to study cognitive processes, heart deformations and respiration; Combining complementary information from different imaging modalities. One example may be the fusion of anatomical and functional information.

Since the size and shape of structures vary across modalities, evaluating the alignment quality can be more challenging. Thus, similarity measures such as mutual information may be used; Characterizing a population of subjects. In contrast to intra-subject registration, a one-to-one mapping may not exist between subjects, depending on the structural variability of the organ of interest. Inter-subject registration may be used for atlas construction in computational anatomy. Here, the objective may be to statistically model the anatomy of organs across subjects; Computer-assisted surgery: in computer-assisted surgery pre-operative images such as CT or MRI may be registered to intra-operative images or tracking systems to facilitate image guidance or navigation. There may be several considerations made when performing image registration: The transformation model. Common choices are rigid, affine, and deformable transformation models. B-spline and thin plate spline models are commonly used for parameterized transformation fields. Non-parametric or dense deformation fields carry a displacement vector at every grid location; this may use additional regularization constraints. A specific class of deformation fields are diffeomorphisms, which are invertible transformations with a smooth inverse; The similarity metric. A distance or similarity function is used to quantify the registration quality. This similarity can be calculated either on the original images or on features extracted from the images. Common similarity measures are sum of squared distances (SSD), correlation coefficient, and mutual information. The choice of similarity measure depends on whether the images are from the same modality; the acquisition noise can also play a role in this decision. For example, SSD may be the optimal similarity measure for images of the same modality with Gaussian noise. However, the image statistics in ultrasound may be significantly different from Gaussian noise, leading to the introduction of ultrasound specific similarity measures.

Multi-modal registration may use a more sophisticated similarity measure; alternatively, a different image representation can be used, such as structural representations or registering adjacent anatomy; The optimization procedure. Either continuous or discrete optimization is performed. For continuous optimization, gradient-based optimization techniques are applied to improve the convergence speed. (Search "medical image computing" on Wikipedia.com Jun. 24, 2021. CC-BY-SA 3.0 Modified. Accessed Jun. 25, 2021.)

"Register" or "Registration" refers to an act of aligning, mating, contacting, engaging, or coupling one or more parts and/or surfaces of one object in relation to one or more parts and/or surfaces of another object. Often, the one or more parts and/or surfaces of one object include protrusions and/or depressions that are the inverse or mirror configuration of protrusions and/or depressions of one or more parts and/or surfaces of the other object.

"Registration key" refers to a structure, surface, feature, module, component, apparatus, and/or system that facilitates, enables, guides, promotes, precision in the alignment of two objects by way of registration. In one aspect a registration key can include a surface and one or more recesses and/or features of that surface that are configured to fit within corresponding recesses, projections, and/or other features of another structure such as another surface. In one aspect a registration key can include a surface and one or more projections and/or features of, extending from, or connected to that surface that are configured to fit within corresponding recesses, projections, and/or other features of another structure such as another surface. In certain aspects, the features of the registration key may be configured to fit within, or in contact, or in close contact with those of the another structure. In one embodiment, when the two structures align the registration key has served its purpose.

As used herein, a "resection" refers to a method, procedure, or step that removes tissue from another anatomical structure or body. A resection can include an osteotomy that cuts through a bone or other tissue because the osteotomy still removes at least a minimal amount of tissue. A resection is typically performed by a surgeon on a part of a body of a patient. A resection is a type of osteotomy. (Search "surgery" on Wikipedia.com May 26, 2021. CC-BY-SA 3.0 Modified. Accessed May 26, 2021.) Resection may be used as a noun or a verb. In the verb form, the term is "resect" and refers to an act of performing, or doing, a resection. Past tense of the verb resect is resected.

"Anatomical structure" refers to any part or portion of a part of a body of a person, animal, or other patient. Examples of anatomical structures, include but are not limited to, a bone, bones, soft tissue, a joint, joints, a tissue surface, a protrusion, a recess, an opening, skin, hard tissue, teeth, mouth, eyes, hair, nails, fingers, toes, legs, arms, torso, vertebrae, ligaments, tendons, organs, or the like.

"Anatomical reference" refers to any reference(s) that is, or is on, or is in, or is otherwise associated, with an anatomical structure. Examples of anatomical structures, include but are not limited to, a bone, bones, soft tissue, a joint, joints, skin, hard tissue, teeth, mouth, eyes, hair, nails, fingers, toes, legs, arms, torso, vertebrae, ligaments, tendons, organs, a hole, a post, a plurality of holes, a plurality of posts, a fastener, a suture, a clamp, an instrument, an implant, or the like.

"Bone condition" refers to any of a variety of conditions of bones of a patient. Generally, a bone condition refers to an orientation, position, and/or alignment of one or more bones of the patient relative to other anatomical structures of the body of the patient. Bone conditions may be caused by or result from deformities, misalignment, malrotation, fractures, joint failure, and/or the like. A bone condition includes, but is not limited to, any angular deformities of one or more bone segments in either the lower or upper extremities (for example, tibial deformities, calcaneal deformities, femoral deformities, and radial deformities). Alternatively, or in addition, "bone condition" can refer to the structural makeup and configuration of one or more bones of a patient. Thus bone condition may refer to a state or condition of regions, a thickness of a cortex, bone density, a thickness and/or porosity of internal regions (e.g. whether it is calcaneus or solid) of the bone or parts of the bone such as a head, a base, a shaft, a protuberance, a process, a lamina, a foramen, and the like of a bone, along the metaphyseal region, epiphysis region, and/or a diaphyseal region. "Malrotation" refers to a condition in which a part, typically a part of a patient's body has rotated from a normal position to an unnormal or uncommon position.

As used herein, a "guide" refers to a part, component, member, or structure designed, adapted, configured, or engineered to guide or direct one or more other parts, components, or structures. A guide may be part of, integrated with, connected to, attachable to, or coupled to, another structure, device, or instrument. In one embodiment, a guide may include a modifier that identifies a particular function, location, orientation, operation, type, and/or a particular structure of the guide. Examples of such modifiers applied to a guide, include, but are not limited to, "pin guide" that guides or directs one or more pins, a "cutting guide" that guides or directs the making or one or more cuts, a placement, deployment, or insertion guide that guides or directs the placement, positioning, orientation, deployment, installation, or insertion of a fastener and/or implant, a "cross fixation guide" that guides deployment of a fastener or fixation member, an "alignment guide" that guides the alignment of two or more objects or structures, a "navigation guide" that guides a user in navigating a course or process or procedure such as a surgical procedure, a "resection guide" that serves to guide resection of soft or hard tissue, such as in an osteotomy, a "reduction guide" can serve to guide reduction of one or more bone segments or fragments, an "placement guide" that serves to identify how an object can be placed in relation to another object or structure, and the like. Furthermore, guides may include modifiers applied due to the procedure or location within a patient for which the guide is to be used. For example, where a guide is used at a joint, the guide may be referred to herein as an "arthrodesis guide."

Those of skill in the art will appreciate that a resection feature may take a variety of forms and may include a single feature or one or more features that together form the resection feature. In certain embodiments, the resection feature may take the form of one or more slots or cut channels. Alternatively, or in addition, a resection feature may be referenced using other names including, but not limited to, channel, cut channels, and the like.

"Cut channel" refers to a channel, slot, hole, or opening, configured to facilitate making a cut. In certain embodiments, a cut channel is one example of a resection feature, resection member, and/or resection guide. "Rotation slot" refers to a channel, slot, hole, or opening, configured to facilitate rotating one structure in relation to another structure.

As used herein, "slot" refers to a narrow opening or groove. (search "slot" on Merriam-Webster.com. Merriam-Webster, 2021. Web. 4 Aug. 2021. Modified.)

"Hole" refers to a gap, an opening, an aperture, a port, a portal, a space or recess in a structure, a void in a structure, or the like. In certain embodiments, a hole can refer to a structure configured specifically for receiving something and/or for allowing access. In certain embodiments, a hole can pass through a structure. In other embodiments, an opening can exist within a structure but not pass through the structure. A hole can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape. As used herein, the term "hole" can include one or more modifiers that define specific types of "holes" based on the purpose, function, operation, position, or location of the "hole." As one example, a "fastener hole" refers to an "hole" adapted, configured, designed, or engineered to accept or accommodate a "fastener."

As used herein, an "opening" refers to a gap, a hole, an aperture, a port, a portal, a slit, a space or recess in a structure, a void in a structure, or the like. In certain embodiments, an opening can refer to a structure configured specifically for receiving something and/or for allowing access. In certain embodiments, an opening can pass through a structure. In such embodiments, the opening can be referred to as a window. In other embodiments, an opening can exist within a structure but not pass through the structure. In other embodiments, an opening can initiate on a surface or at an edge or at a side of a structure and extend into the structure for a distance, but not pass through or extend to another side or edge of the structure. In other embodiments, an opening can initiate on a surface or at an edge or at a side of a structure and extend into the structure until the opening extends through or extends to another side or edge of the structure. An opening can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape. As used herein, the term "opening" can include one or more modifiers that define specific types of "openings" based on the purpose, function, operation, position, or location of the "opening." As one example, a "fastener opening" refers to an "opening" adapted, configured, designed, or engineered to accept or accommodate a "fastener."

As used herein, an "interface," "user interface," or "engagement interface" refers to an area, a boundary, or a place at which two separate and/or independent structures, members, apparatus, assemblies, components, and/or systems join, connect, are coupled, or meet and act on, or communicate, mechanically and/or electronically, with each other. In certain embodiments, "interface" may refer to a surface forming a common boundary of two bodies, spaces, structures, members, apparatus, assemblies, components, or phases. (search "interface" on Merriam-Webster.com. Merriam-Webster, 2021. Web. 15 Nov. 2021. Modified.) In certain embodiments, the term interface may be used with an adjective that identifies a type or function for the interface. For example, an engagement or coupling interface may refer to one or more structures that interact, connect, or couple to mechanically join or connect two separate structures, each connected to a side of the interface. In another example, a user interface may refer to one or more mechanical, electrical, or electromechanical structures that interact with or enable a user to provide user input, instructions, input signals, data, or data values and receive output, output data, or feedback.

"Cortical bone" refers to a type of bone tissue. Cortical bone is a type of bone tissue typically found between an external surface of a bone and an interior area of the bone. Cortical bone is more dense and typically stronger structurally than other types of bone tissue. "Cortical surface" refers to a surface of cortical bone.

"Cortex" refers to an area of bone that extends from an external surface of the bone towards a center part of the bone. The cortex is typically comprised of cortical bone.

"Transosseous placement feature" refers to a placement feature that extends through one or more bones and that enables, or facilitates, placement of another device, apparatus, or instrument.

"Patient specific feature" refers to a feature, function, structure, device, guide, tool, instrument, apparatus, member, component, system, assembly, module, or subsystem that is adjusted, tailored, modified, organized, configured, designed, arranged, engineered, and/or fabricated to specifically address the anatomy, physiology, condition, abnormalities, needs, or desires of a particular patient or surgeon serving the particular patient. In one aspect, a patient specific feature is unique to a single patient and may include features unique to the patient such as a number of cut channels, a number of bone attachment features, a number of bone engagement surfaces, a number of resection features, a depth of one or more cutting channels, an angle for one or more resection channels, a surface contour, component position, component orientation, and/or other features. "Medial resection guide" refers to a resection guide designed, engineered, fabricated, or intended for use with, one, in, or about a medial part, section, surface, portion, or aspect of an anatomical structure such as a bone, digit, limb, or other anatomical structure for one or more steps of a resection procedure. "Lateral resection guide" refers to a resection guide designed, engineered, fabricated, or intended for use with, one, in, or about a lateral part, section, surface, portion, or aspect of an anatomical structure such as a bone, digit, limb, or other anatomical structure for one or more steps of a resection procedure.

"Prescription" or "Prescribed" refers to a written order, as by a physician or nurse practitioner, for the administration of a medicine, preparation of an implant, preparation of an instrument, or other intervention. Prescription can also refer to the prescribed medicine or intervention. (Search "prescription" on wordhippo.com. WordHippo, 2023. Web. Accessed 3 May 2023. Modified.)

As used herein, "end" refers to a part or structure of an area or span that lies at the boundary or edge. An end can also refer to a point that marks the extent of something and/or a point where something ceases to exist. An end can also refer to an extreme or last part lengthwise of a structure or surface. (search "end" on Merriam-Webster.com. Merriam-Webster, 2021. Web. 4 Aug. 2021. Modified.)

As used herein, "edge" refers to a structure, boundary, or line where an object, surface, or area begins or ends. An edge can also refer to a boundary or perimeter between two structures, objects, or surfaces. An edge can also refer to a narrow part adjacent to a border. (search "edge" on Merriam-Webster.com. Merriam-Webster, 2021. Web. 3 Aug. 2021. Modified.) In certain embodiments, an edge can be a one dimensional or a two dimensional structure that joins two adjacent structures or surfaces. Furthermore, an edge may be at a perimeter of an object or within a perimeter or boundary of an object.

"Bone fragment" refers to a part of a bone that is normally part of another bone of a patient. A bone fragment may be separate from another bone of a patient due to a deformity or trauma. In one aspect, the bone the bone fragment is normally connected or joined with is referred to as a parent bone.

"Joint" or "Articulation" refers to the connection made between bones in a human or animal body which link the skeletal system to form a functional whole. Joints may be biomechanically classified as a simple joint, a compound joint, or a complex joint. Joints may be classified anatomically into groups such as joints of hand, elbow joints, wrist joints, axillary joints, sternoclavicular joints, vertebral articulations, temporomandibular joints, sacroiliac joints, hip joints, knee joints, ankle joints, articulations of foot, and the like. (Search "joint" on Wikipedia.com Dec. 19, 2021. CC-BY-SA 3.0 Modified. Accessed Jan. 20, 2022.)

"Tarso-metatarsal joint" or "TMT joint" refers to a joint of a patient between a metatarsal bone and one or more cuneiform/tarsal/cuboid bones. The TMT joint may also be referred to as a "Lis Franc" or "Lisfranc" joint after a French surgeon Lisfranc.

"Cut surface" refers to a surface of an object that is created or formed by the removal of one or more parts of the object that includes the original surface. Cut surfaces can be created using a variety of methods, tools, or apparatuses and may be formed using a variety of removal actions, including, but not limited to, fenestrating, drilling, abrading, cutting, sawing, chiseling, digging, scrapping, and the like. Tools and/or methods used for forming a cut surface can include manual, mechanical, motorized, hydraulic, automated, robotic, and the like. In certain embodiments, the cut surface (s) are planar.

"Orientation" refers to a direction, angle, position, condition, state, or configuration of a first object, component, part, apparatus, system, or assembly relative to another object, component, part, apparatus, system, assembly, reference point, reference axis, or reference plane.

"Longitudinal axis" or "Long axis" refers to an axis of a structure, device, object, apparatus, or part thereof that extends from one end of a longest dimension to an opposite end. Typically, a longitudinal axis passes through a center of the structure, device, object, apparatus, or part thereof along the longitudinal axis. The center point used for the longitudinal axis may be a geometric center point and/or a mass center point.

As used herein, a "drive", "drive feature", or "drive recess" refers to an apparatus, instrument, structure, member, device, component, system, or assembly structured, organized, configured, designed, arranged, or engineered to receive a torque and transfer that torque to a structure connected or coupled to the drive. At a minimum, a drive is a set of shaped cavities and/or protrusions on a structure that allows torque to be applied to the structure. Often, a drive includes a mating tool, known as a driver. For example, cavities and/or protrusions on a head of a screw are one kind of drive and an example of a corresponding mating tool is a screwdriver, that is used to turn the screw, the drive. Examples of a drive include but are not limited to screw drives such as slotted drives, cruciform drives, square drives, multiple square drives, internal polygon, internal hex drives, penta lobular sockets, hex lobular sockets, combination drives, external drives, tamper-resistant drives, and the like. (Search 'list of screw drives' on Wikipedia.com Mar. 12, 2021. Modified. Accessed Mar. 19, 2021.)

"Thread" or "threads" refers to a helical structure used to convert between rotational and linear movement or force. A thread is a ridge wrapped around a cylinder or cone in the form of a helix, with the ridge wrapped around the cylinder being called a straight thread and the ridge wrapped around the cone called a tapered thread. Straight threads or tapered threads are examples of external threads, also referred to as male threads. Threads that a correspond to male threads are referred to as female threads and are formed within the inside wall of a matching hole, passage, or opening of a nut or substrate or other structure. A thread used with a fastener may be referred to as a screw thread and can be an important feature of a simple machine and also as a threaded fastener. The mechanical advantage of a threaded fastener depends on its lead, which is the linear distance the threaded fastener travels in one revolution. (Search 'screw thread' on Wikipedia.com Jul. 17, 2022. Modified. Accessed Aug. 1, 2022.)

"Cutting tool" refers to any tool that can be used to cut or resect another object. In particular, a cutting tool can refer to a manual or power tool for cutting or resecting tissue of a patient. Examples of cutting tools include, but are not limited to, a burr, an oscillating saw, a reciprocating saw, a grater saw, a drill, a mill, a side-cutting burr, or the like.

As used herein, a "shaft" refers to a long narrow structure, device, component, member, system, or assembly that is structured, organized, configured, designed, arranged, or engineered to support and/or connect a structure, device, component, member, system, connected to each end of the shaft. Typically, a shaft is configured to provide rigid support and integrity in view of a variety of forces including tensile force, compression force, torsion force, shear force, and the like. In addition, a shaft can be configured to provide rigid structural support and integrity in view of a loads including axial loads, torsional loads, transverse loads, and the like. A shaft may be oriented and function in a variety of orientations including vertical, horizontal, or any orientation between these and in two or three dimensions. A shaft may be made from a variety of materials including, but not limited to, metal, plastic, ceramic, wood, fiberglass, acrylic, carbon, biocompatible materials, biodegradable materials or the like. A shaft may be formed of any biocompatible materials, including but not limited to biocompatible metals such as Titanium, Titanium alloys, stainless steel, carbon fiber, combinations of carbon fiber and a metallic alloy, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others, or any combination of these materials.

"Head" refers to a device, apparatus, member, component, system, assembly, module, subsystem, circuit, or structure, organized, configured, designed, arranged, or engineered to have a prominent role in a particular feature, function, operation, process, method, and/or procedure for a device, apparatus, member, component, system, assembly, module, subsystem, circuit, or structure the includes, is coupled to, or interfaces with the head. In certain embodiments, the head may sit at the top or in another prominent position when interfacing with and/or coupled to a device, apparatus, member, component, system, assembly, module, subsystem, circuit, or structure.

As used herein, an "interface," "user interface," or "engagement interface" refers to an area, a boundary, or a place at which two separate and/or independent structures, members, apparatus, assemblies, components, and/or systems join, connect, are coupled, or meet and act on, or communicate, mechanically and/or electronically, with each other. In certain embodiments, "interface" may refer to a surface forming a common boundary of two bodies, spaces, structures, members, apparatus, assemblies, components, or phases. (search "interface" on Merriam-Webster.com. Merriam-Webster, 2021. Web. 15 Nov. 2021. Modified.) In certain embodiments, the term interface may be used with an adjective that identifies a type or function for the interface. For example, an engagement or coupling interface may refer to one or more structures that interact, connect, or couple to mechanically join or connect two separate structures, each connected to a side of the interface. In another example, a user interface may refer to one or more mechanical, electrical, or electromechanical structures that interact with or enable a user to provide user input, instructions, input signals, data, or data values and receive output, output data, or feedback.

"Cut surface" or "cut face" refers to a surface of an object that is created or formed by the removal of one or more parts of the object that includes the original surface. Cut surfaces or cut faces can be created using a variety of methods, tools, or apparatuses and may be formed using a variety of removal actions, including, but not limited to, fenestrating, drilling, abrading, cutting, sawing, chiseling, digging, scrapping, and the like. Tools and/or methods used for forming a cut surface or cut face can include manual, mechanical, motorized, hydraulic, automated, robotic, and the like.

The present disclosure discloses surgical systems and methods by which a bone condition, that can include a deformity, may be corrected or otherwise addressed. Known methods of addressing bone conditions are often limited to a finite range of discretely sized instruments. A patient with an unusual condition, or anatomy that falls between instrument sizes, may not be readily treated with such systems.

Furthermore, patient-specific instruments may be used for various other procedures on the foot, or on other bones of the musculoskeletal system. For example, patient-specific instruments and/or other instruments may be used for various procedures including resection and translation of a head of a long bone, determining where to perform an osteotomy on one or more joints or part of one or more bones, determining ligament or tendon attachment or anchoring points, determining where to form bone tunnels or position anchors, tendon or graft deployment, and the like.

FIG. 1A is a flowchart diagram depicting a method 100 for correcting a bone condition, according to one embodiment. The method 100 may be used for any of a wide variety of bone conditions, including but not limited to deformities, fractures, joint failure, and/or the like. Further, the method 100 may provide correction with a wide variety of treatments, including but not limited to arthroplasty, arthrodesis, fracture repair, and/or the like.

As shown, the method 100 may begin with a step 102 in which a CT scan (or another three-dimensional image, also referred to as medical imaging) of the patient's anatomy is obtained. The step 102 may include capturing a scan of only the particular bone(s) to be treated, or may include capture of additional anatomic information, such as the surrounding tissues. Additionally or alternatively, the step 102 may include receiving a previously captured image, for example, at a design and/or fabrication facility. Performance of the step 102 may result in possession of a three-dimensional model of the patient's anatomy, or three-dimensional surface points that can be used to construct such a three-dimensional model.

After the step 102 has been carried out, the method 100 may proceed to a step 104 in which a CAD model of the patient's anatomy (including one or more bones) is generated. The CAD model may be one example of a bone model. The CAD model may be of any known format, including but not limited to SolidWorks, Catia, AutoCAD, or DXF. In some embodiments, customized software may be used to generate the CAD model from the CT scan. The CAD model may only include the bone(s) to be treated and/or may include surrounding tissues. In alternative embodiments, the step 104 may be omitted, as the CT scan may capture data that can directly be used in future steps without the need for conversion.

In one embodiment, the CAD model generated and/or patient-specific instrumentation, implants, and/or plan for conducting an operative procedure, may be enhanced by the use of advanced computer analysis system, machine learning, and/or automated/artificial intelligence. For example, these technologies may be used to revise a set of steps for a procedure such that a more desirable outcome is achieved.

In a step 106, the CAD model and/or CT scan data may be used to model patient-specific instrumentation that can be used to correct the condition, as it exists in the patient's anatomy. In some embodiments, any known CAD program may be used to view and/or manipulate the CAD model and/or CT scan, and generate one or more instruments that are matched specifically to the size and/or shape of the patient's bone(s). In some embodiments, such instrumentation may include a targeting guide, trajectory guide, drill guide, cutting guide, tendon trajectory guide, capital fragment positioning guide, or similar guide that can be attached to one or more bones, with one or more features that facilitate work on the one or more bones pursuant to a procedure such as arthroplasty or arthrodesis. In some embodiments, performance of the step 106 may include modelling an instrument with a bone engagement surface that is shaped to match the contour of a surface of the bone, such that the bone engagement surface can lie directly on the corresponding contour.

In a step 108, the model(s) may be used to manufacture patient-specific instrumentation and/or implants. This may be done via any known manufacturing method, including casting, forging, milling, additive manufacturing, and/or the like. Additive manufacturing may provide unique benefits, as the model may be directly used to manufacture the instrumentation and/or implants (without the need to generate molds, tool paths, and/or the like beforehand). Such instrumentation may optionally include a targeting guide, trajectory guide, drill guide, cutting guide, positioner, positioning guide, tendon trajectory guide, or the like.

In addition to, or in the alternative to the step 108, the model(s) may be used to select from available sizes of implants and/or instruments or instruments having various attributes and advise the surgeon accordingly. For example, where a range of guides are available for a given procedure, analysis of the CAD data may facilitate pre-operative selection of the optimal guide and/or optimal placement of the guide on the bone. Similarly, if a range of implants and/or instruments may be used for a given procedure, analysis of the CAD data may facilitate pre-operative selection of the optimal implant(s). More particularly, properly-sized spacers, screws, bone plates, and/or other hardware may be pre-operatively selected.

Thus, the result of the step 108 may provision, to the surgeon, of one or more of the following: (1) one or more patient-specific instruments; (2) one or more patient-specific implants; (3) an instrument, selected from one or more available instrument sizes and/or configurations; (4) an implant, selected from one or more available implant sizes and/or configurations; (5) instructions for which instrument(s) to select from available instrument sizes and/or configurations; (6) instructions for which implant(s) to select from available implant sizes and/or configurations; (7) instructions for proper positioning or anchorage of one or more instruments to be used in the procedure; and (8) instructions for proper positioning or anchorage of one or more implants to be used in the procedure. These items may be provided to the surgeon directly, or to a medical device company or representative, for subsequent delivery to the surgeon.

In a step 110, the manufactured instrumentation may be used in surgery to facilitate treatment of the condition. In some embodiments, this may include placing the modelled bone engagement surface against the corresponding contour of the bone used to obtain its shape, and then using the resection feature(s) to guide resection of one or more bones. Then the bone(s) may be further treated, for example, by attaching one or more joint replacement implants (in the case of joint arthroplasty), or by attaching bone segments together (in the case of arthrodesis or fracture repair). Prior to completion of the step 110, the instrumentation may be removed from the patient, and the surgical wound may be closed.

As mentioned previously, the method 100 may be used to correct a wide variety of bone conditions. One example of the method 100 will be shown and described in connection with FIG. 1B, for correction of a bunion deformity of the foot.

In certain embodiments, one or more of a method, apparatus, and/or system of the disclosed solution can be used for training a surgeon to perform a patient-specific procedure or technique. In one embodiment, the CAD model generated and/or patient-specific instrumentation, implants, and/or plan for conducting an operative procedure can be used to train a surgeon to perform a patient-specific procedure or technique.

In one example embodiment, a surgeon may submit a CT scan of a patient's foot to an apparatus or system that implements the disclosed solution. Next, a manual or automated process may be used to generate a CAD model and for making the measurements and correction desired for the patient. In the automated process, advanced computer analysis system, machine learning and automated/artificial intelligence may be used to generate a CAD model and/or one or more patient-specific instruments and/or operation plans. For example, a patient-specific instrument may be fabricated that is registered to the patient's anatomy using a computer-aided machine (CAM) tool. In addition, a CAM tool may be used to fabricate a 3D structure representative of the patient's anatomy, referred to herein as a patient-specific synthetic cadaver. (e.g. one or more bones of a patient's foot). Next, the patient-specific instrument and the patient-specific synthetic cadaver can be provided to a surgeon who can then rehearse an operation procedure in part or in full before going into an operating room with the patient.

In certain embodiments, the patient-specific instrument or instrument can be used to preposition and/or facilitate pre-drilling holes for a plate system for fixation purposes. Such plate systems may be optimally placed, per a CT scan, after a correction procedure for optimal fixation outcome. In another embodiment, the CAD model and/or automated process such as advanced computer analysis, machine learning and automated/artificial intelligence may be used to measure a depth of the a through a patient-specific resection guide for use with robotics apparatus and/or systems which would control the depth of each cut within the guide to protect vital structures below or adjacent to a bone being cut. In another embodiment, the CAD model and/or automated process such as advanced computer analysis, machine learning and automated/artificial intelligence may be used to define desired fastener (e.g. bone screw) length and/or trajectories through a patient-specific instrument and/or implant. The details for such lengths, trajectories, and components can be detailed in a report provided to the surgeon preparing to perform a procedure.

FIG. 1B is a flowchart diagram depicting a method 120 for correcting or remediating a bone condition, according to one embodiment. The method 120 may be used to prepare for an orthopedic procedure which corrects or remediates a bone, muscle, and/or tendon condition of a patient.

As shown, the method 120 may begin with a step 122 in which a CT scan (or another three-dimensional image) of the patient's foot is obtained. The step 122 may include capturing a scan of select bones of a patient or may include capturing additional anatomic information, such as the entire foot. Additionally or alternatively, the step 122 may include receipt of previously captured image data. Capture of the entire foot in the step 122 may facilitate proper alignment of the first metatarsal with the rest of the foot (for example, with the second metatarsal). Performance of the step 122 may result in generation of a three-dimensional model of the patient's foot, or three-dimensional surface points that can be used to construct such a three-dimensional model.

After the step 122 has been carried out, the method 120 may proceed to a step 124 in which a CAD model of the relevant portion of the patient's anatomy is generated. The CAD model may optionally include the bones of the entire foot, like the CT scan obtained in the step 122. In alternative embodiments, the step 124 may be omitted in favor of direct utilization of the CT scan data, as described in connection with the step 104.

In a step 126, the CAD model and/or CT scan data may be used to model patient-specific instrumentation that can be used to correct or remediate a bone condition. Such instrumentation may include a guide. In one example, the guide can seat or abut or contact a surface of a bone and including an opening that guides a trajectory for a fastener for a procedure. In some embodiments, performance of the step 126 may include modelling the guide with a bone engagement surface that is shaped to match contours of the surfaces of the bone, such that the bone engagement surface can lie directly on the corresponding contours of the bone.

In a step 128, the model(s) may be used to manufacture patient-specific instrumentation and/or instruments. This may include manufacturing an instrument with the bone engagement surface and/or other features as described above. As in the step 108, the step 128 may additionally or alternatively involve provision of one or more instruments and/or implants from among a plurality of predetermined configurations or sizes. Further, the step 128 may additionally, or alternatively, involve provision of instructions for placement and/or anchorage of one or more instruments and/or instruments to carry out the procedure.

In a step 130, the manufactured instrument may be used in surgery to facilitate treatment of the condition. In certain embodiments, a bone engagement surface of the instrument may be placed against the corresponding contours of the bone. The instrument may include an opening and/or trajectory guide to guide insertion of a trajectory guide such as a temporary fastener such as a K-wire. The instrument may then be removed, and the remaining steps of a surgical procedure performed.

Method 100 and method 120 are merely exemplary. Those of skill in the art will recognize that various steps of the method 100 and the method 120 may be reordered, omitted, and/or supplemented with additional steps not specifically shown or described herein.

As mentioned previously, the method 120 is one species of the method 100; the present disclosure encompasses many different procedures, performed with respect to many different bones and/or joints of the body. Exemplary steps and instrumentation for the method 120 will further be shown and described in connection with the present disclosure. Those of skill in the art will recognize that the method 120 may be used in connection with different instruments; likewise, the instruments of the present disclosure may be used in connection with methods different from the method 100 and the method 120.

Figures 2A, 2B:
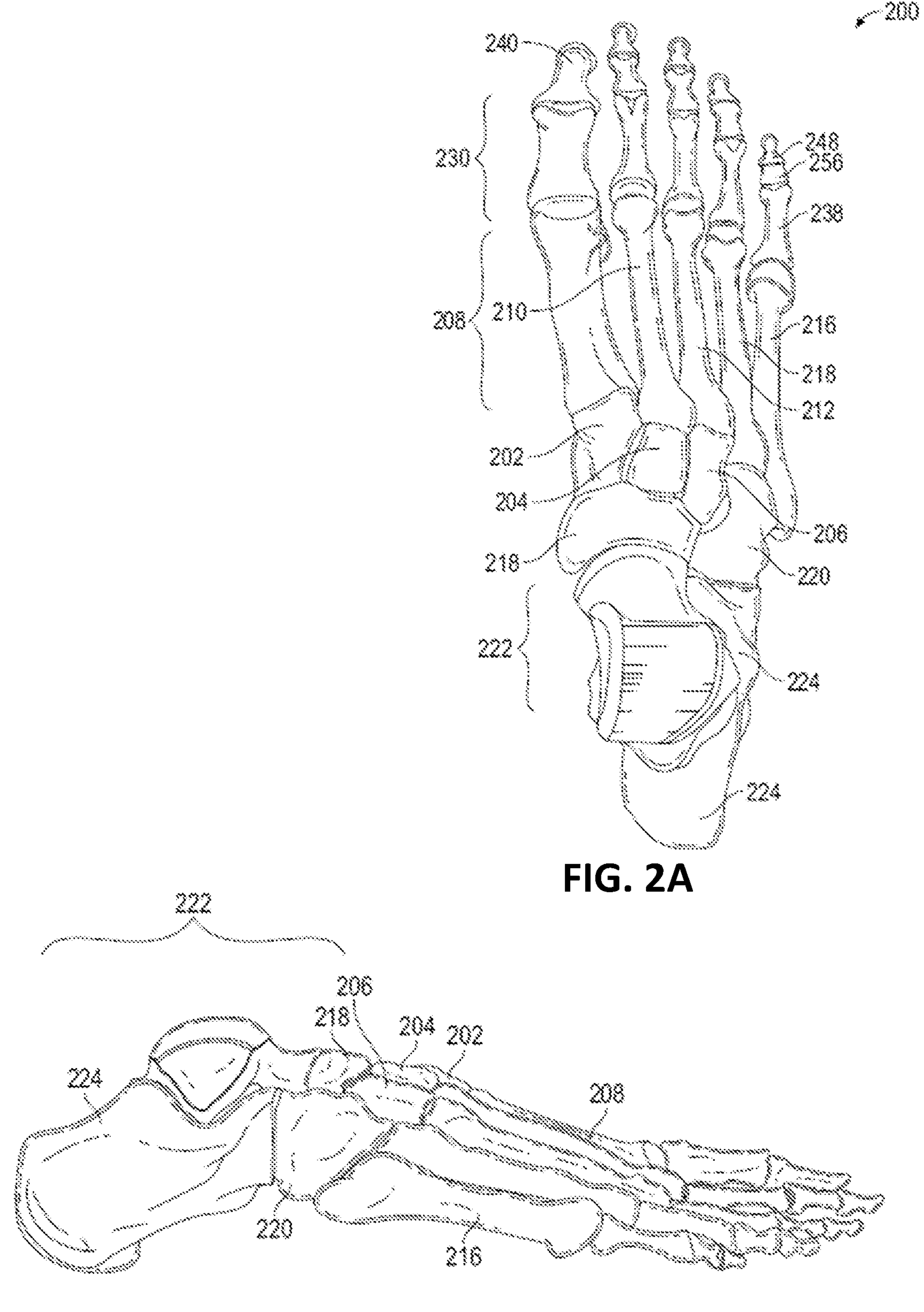
FIG. 2A is a dorsal perspective view of bones of a foot.
FIG. 2B is a lateral perspective view of bones of a foot.

FIG. 2A is a perspective dorsal view of a foot 200. The foot 200 may have a medial cuneiform 202, an intermediate cuneiform 204, lateral cuneiform 206, a first metatarsal 208, a second metatarsal 210, third metatarsal 212, fourth metatarsal 214, fifth metatarsal 216, navicular 218, cuboid 220, talus 222, and calcaneus 224, among others. The medial cuneiform 202 and the intermediate cuneiform 204 may be joined together at a first metatarsocuneiform joint, and the first metatarsal 208 and the second metatarsal 210 may be joined together at a second metatarsocuneiform joint. The foot 200 includes a set of proximal phalanges numbered first through fifth (230, 232, 234, 236, 238) and a set of distal phalanges numbered first through fifth (240, 242, 244, 246, 248) and a set of middle phalanges numbered second through fifth (250, 252, 254, 256).

FIG. 2B is a perspective lateral view of a foot 200, with bones of the foot labeled.

Figure 2C:
FIG. 2C is a medial perspective view of bones of a foot.
Figure 2C:
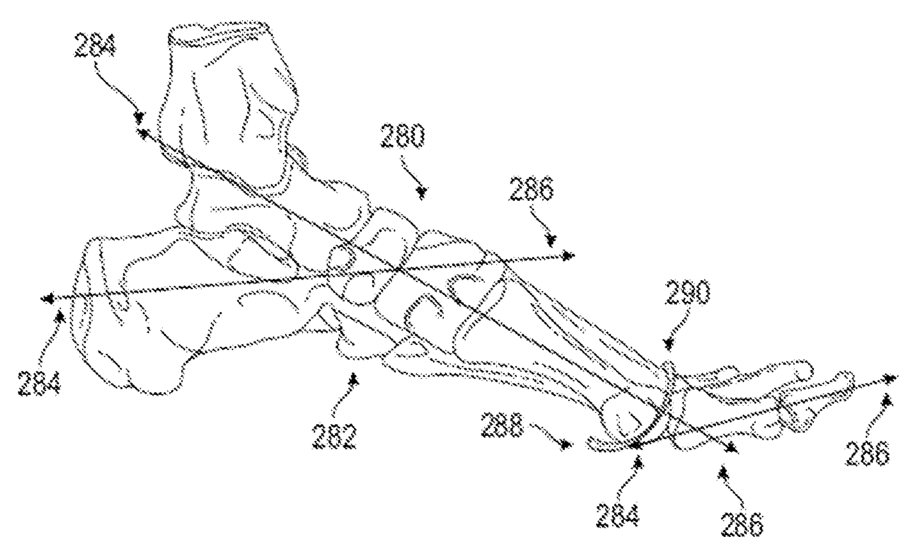
Figure 2D:
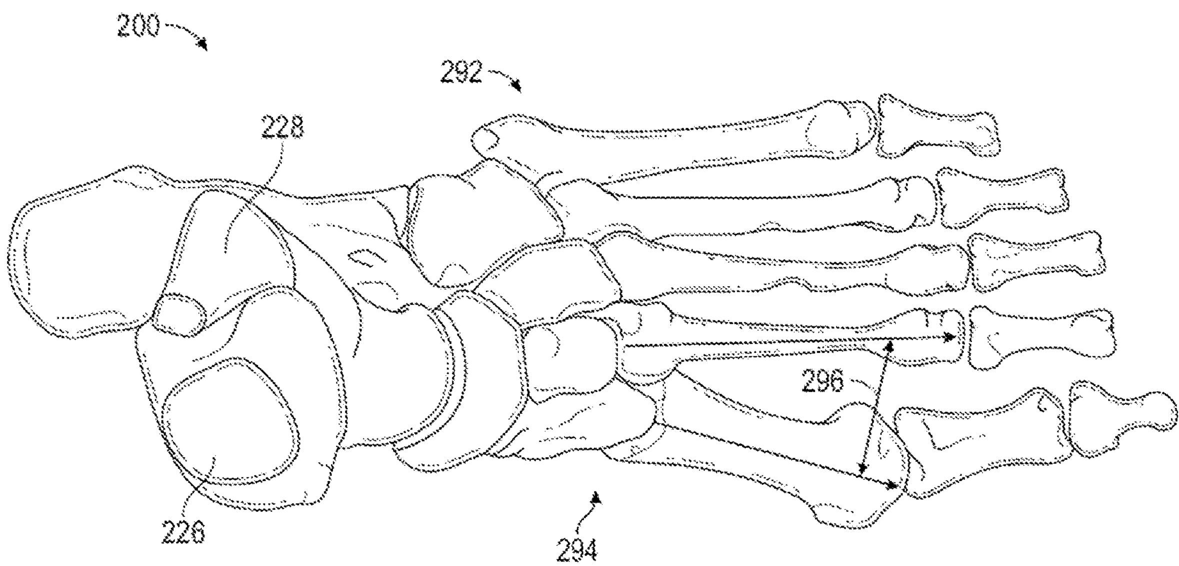
FIG. 2D is a dorsal perspective view of bones of a foot.

FIG. 2C is a perspective medial view of a foot illustrating a dorsal side 280 and a plantar side 282. The foot 200, as illustrated, may have a tibia 226 and a fibula 228, among others. Dorsal refers to the top of the foot. Plantar refers to the bottom of the foot. Proximal 284 is defined as "closer to the primary attachment point". Distal 286 is defined as "further away from the attachment point". Plantarflex or plantarflexion 288 means movement toward the plantar side 282 of a foot or hand, toward the sole or palm. Dorsiflex or dorsiflexion 290 means movement toward the dorsal side 280 of a foot or hand, toward the top. FIG. 2D is a perspective dorsal view of the foot 200. A transverse plane is the plane that shows the top of the foot. A lateral side 292 means a side furthest away from the midline of a body, or away from a plane of bilateral symmetry of the body. A medial side 294 means a side closest to the midline of a body, or toward a plane of bilateral symmetry of the body. For a Lapidus procedure, the intermetatarsal (IM) angle 296 is the angle to be corrected to remove the hallux valgus (bunion) deformity.

Figure 2E:
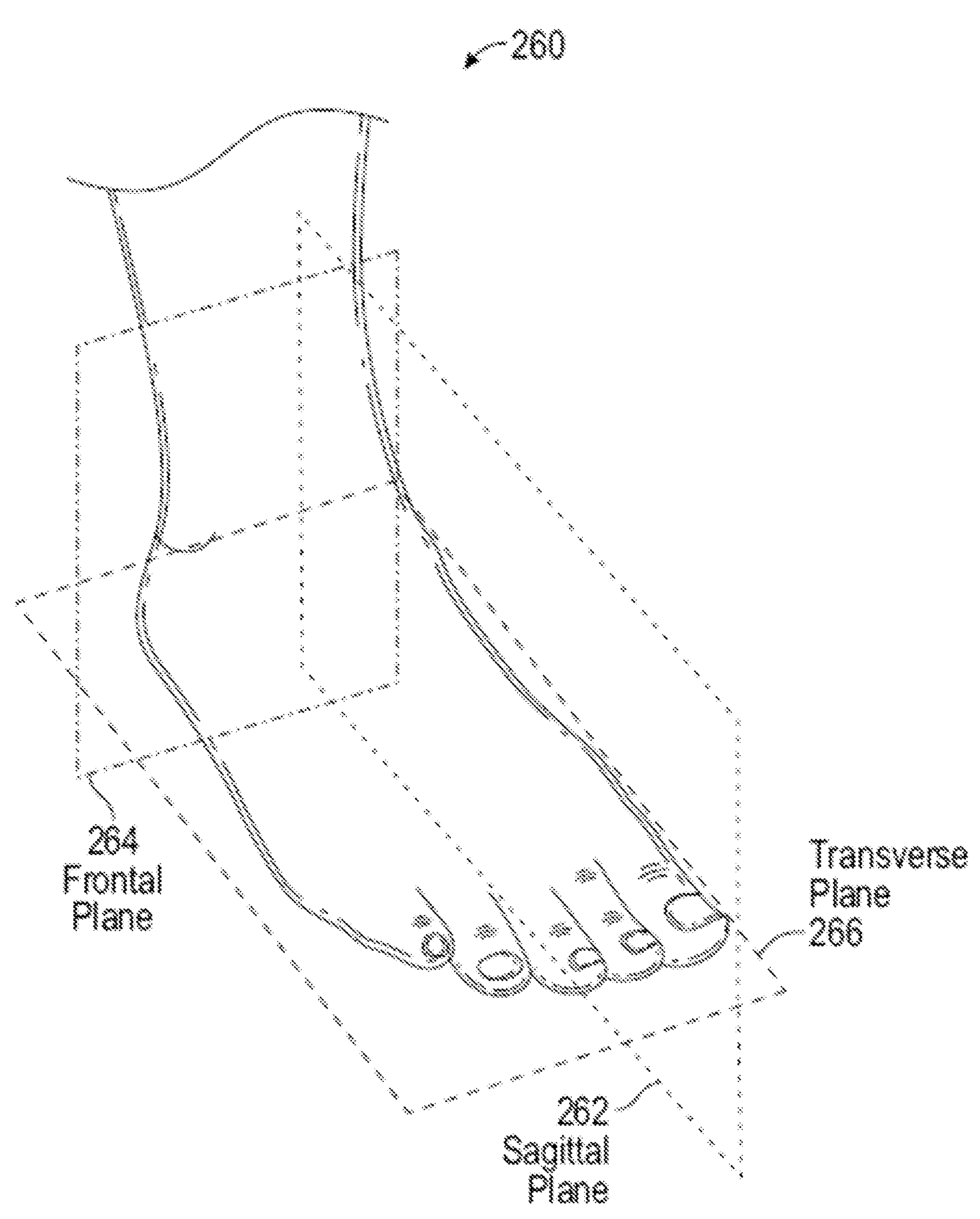
FIG. 2E is a view of a foot illustrating common planes of reference for a human foot.

FIG. 2E is a view of a foot illustrating common planes 260 of reference for a human foot. FIG. 2E illustrates a sagittal plane 262 that divides the foot into a right section and a left section half. The sagittal plane 262 is perpendicular to frontal or coronal plane 264 and the transverse plane 266. In the foot, the frontal plane 264 generally runs vertically through the ankle and the transverse plane 266 generally runs horizontally through the midfoot and toes of the foot.

Every patient and/or condition is different; accordingly, the degree of angular adjustment needed in each direction may be different for every patient. Use of a patient-specific instrument may help the surgeon obtain an optimal realignment, target, or position a bone tunnel, position one or more resections and/or fasteners and the like. Thus, providing patient-specific instruments, jigs, and/or instrumentation may provide unique benefits.

The present patient-specific instrumentation may be used to correct a wide variety of conditions. Such conditions include, but are not limited to, angular deformities of one bone in either the lower or upper extremities (for example, tibial deformities, calcaneal deformities, femoral deformities, and radial deformities). The present disclosure may also be used to treat an interface between two bones (for example, the ankle joint, metatarsal cuneiform joint, lisfranc's joint, complex Charcot deformity, wrist joint, knee joint, etc.). As one example, an angular deformity or segmental malalignment in the forefoot may be treated, such as is found at the metatarsal cuneiform level, the midfoot level such as the navicular cuneiform junction, hindfoot at the calcaneal cuboid or subtalar joint or at the ankle between the tibia and talar junction. Additionally, patient-specific instruments could be used in the proximal leg between two bone segments or in the upper extremity such as found at the wrist or metacarpal levels.

Figure 3:
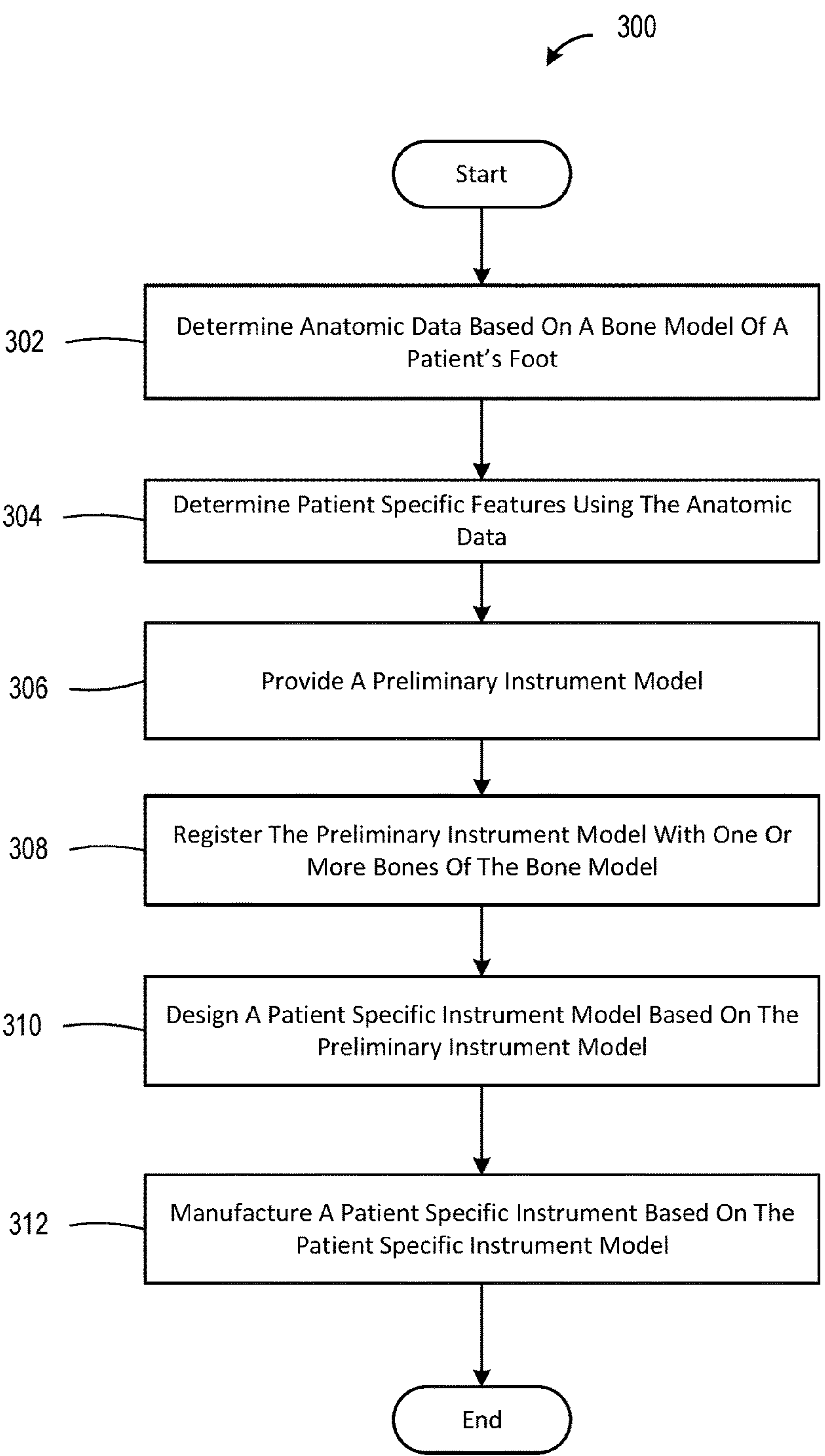
FIG. 3 is a flowchart diagram depicting a method for generating one or more patient-specific instruments, according to one embodiment.

FIG. 3 illustrates a flowchart diagram depicting a method 300 for generating one or more instruments (which may or may not be patient-specific) configured to correct or address a bone or foot condition, according to one embodiment. Prior to steps of the method 300, a bone model (also referred to as CAD model above) is generated. The bone model may be generated using medical imaging of a patient's foot and may also be referred to as an anatomic model. The medical imaging image(s) may be used by computing devices to generate patient imaging data. The patient imaging data may be used to measure and account for orientation of one or more structures of a patient's anatomy. In certain embodiments, the patient imaging data may serve, or be a part of, anatomic data for a patient.

In one embodiment, the method 300 begins after a bone model of a patient's body or body part(s) is generated. In a first step 302, the method 300 may review the bone model and data associated with the bone model to determine anatomic data of a patient's foot.

After step 302, the method 300 may determine 304 one or more angles (e.g., trajectory angle) and/or patient-specific features for a procedure using the anatomic data. "Trajectory angle" refers to a recommended angle for deployment of an instrument, graft, body part, or resection feature angle relative to a bone of a patient for a procedure. In certain embodiments, determining steps, instruments, and/or implants for a corrective procedure may employ advanced computer analysis system, expert systems, machine learning, and/or automated/artificial intelligence.

Next, the method 300 may proceed and a preliminary instrument model is provided 306 from a repository of template models. A preliminary instrument model is a model of a preliminary instrument.

As used herein, "preliminary instrument" refers to an instrument configured, designed, and/or engineered to serve as a template, prototype, archetype, or starting point for creating, generating, or fabricating a patient-specific instrument. In one aspect, the preliminary instrument may be used, as-is, without any further changes, modifications, or adjustments and thus become a patient-specific instrument. In another aspect, the preliminary instrument may be modified, adjusted, or configured to more specifically address the goals, objectives, or needs of a patient or a surgeon and by way of the modifications become a patient-specific instrument. The patient-specific instrument can be used by a user, such as a surgeon, to guide steps in a surgical procedure, such as an osteotomy, graft harvest (e.g., autograft, allograft, or xenograft), minimally invasive surgical (MIS) procedure, and/or a tendon transfer procedure. Accordingly, a preliminary instrument model can be used to generate a patient-specific instrument. The patient-specific instrument model may be used in a surgical procedure to facilitate one or more steps of the procedure, and may be used to generate a patient-specific instrument that can be used in a surgical procedure for the patient.

In certain embodiments, the preliminary instrument model may be generated based on anatomic data and/or a bone model or a combination of these, and no model or predesigned structure, template, or prototype. Alternatively, or in addition, the preliminary instrument model may be, or may originate from, a template instrument model selected from a set of template instrument models. Each model in the set of template instrument models may be configured to fit an average patient's foot. The template instrument model may subsequently be modified or revised by an automated process or manual process to generate the preliminary instrument model used in this disclosure.

As used herein, "template instrument" refers to an instrument configured, designed, and/or engineered to serve as a template for creating, generating, or fabricating a patient-specific instrument. In one aspect, the template instrument may be used, as-is, without any further changes, modifications, or adjustments and thus become a patient-specific instrument. In another aspect, the template instrument may be modified, adjusted, or configured to more specifically address the goals, objectives, or needs of a patient or a surgeon and by way of the modifications become a patient-specific instrument. The patient-specific instrument can be used by a user, such as a surgeon, to guide making one or more resections of a structure, such as a bone for a procedure. Accordingly, a template instrument model can be used to generate a patient-specific instrument model. The patient-specific instrument model may be used in a surgical procedure to address, correct, or mitigate effects of the identified deformity and may be used to generate a patient-specific instrument that can be used in a surgical procedure for the patient.

Next, the method 300 may register 308 the preliminary instrument model with one or more bones of the bone model. This step 308 facilitates customization and modification of the preliminary instrument model to generate a patient-specific instrument model from which a patient-specific instrument can be generated. The registration step 308 may combine two models and/or patient imaging data and position both models for use in one system and/or in one model.

Next, the method 300 may design 310 a patient-specific instrument and/or procedure model based on the preliminary instrument model. The design step 310 may be completely automated or may optionally permit a user to make changes to a preliminary instrument model or partially completed patient-specific instrument model before the patient-specific instrument model is complete. A preliminary instrument model and patient-specific instrument model are two examples of an instrument model. As used herein, "instrument model" refers to a model, either physical or digital, that represents an instrument, tool, apparatus, or device. Examples, of an instrument model can include a cutting instrument model, a resection instrument model, an alignment instrument model, a reduction instrument model, a patient-specific tendon trajectory instrument model, graft harvesting instrument model, minimally invasive surgical (MIS) positioner model, or the like. In one embodiment, a patient-specific instrument and a patient-specific instrument model may be unique to a particular patient and that patient's anatomy and/or condition.

The method 300 may conclude by a step 312 in which a patient-specific instrument may be manufactured based on the patient-specific instrument model. Various manufacturing tools, devices, systems, and/or techniques can be used to manufacture the patient-specific instrument.

FIG. 4 illustrates an exemplary system 400 configured to generate one or more patient-specific instruments configured to facilitate surgical procedures, according to one embodiment. The system 400 may include an apparatus 402 configured to accept, review, receive or reference a bone model 404 and provide a patient-specific instrument 406. In one embodiment, the apparatus 402 is a computing device. In another embodiment, the apparatus 402 may be a combination of computing devices and/or software components or a single software component such as a software application.

The apparatus 402 may include a determination module 410, a location module 420, a provision module 430, a registration module 440, a design module 450, and a manufacturing module 460. Each of which may be implemented in one or more of software, hardware, or a combination of hardware and software.

The determination module 410 determines anatomic data 412 from a bone model 404. In certain embodiments, the system 400 may not include a determination module 410 if the anatomic data is available directly from the bone model 404. In certain embodiments, the anatomic data for a bone model 404 may include data that identifies each anatomic structure within the bone model 404 and attributes about the anatomic structure. For example, the anatomic data may include measurements of the length, width, height, and density of each bone in the bone model. Furthermore, the anatomic data may include position information that identifies where each structure, such as a bone is in the bone model 404 relative to other structures, including bones. The anatomic data may be in any suitable format and may be stored separately or together with data that defines the bone model 404.

In one embodiment, the determination module 410 may use advanced computer analysis system such as image segmentation to determine the anatomic data. The determination module 410 may determine anatomic data from one or more sources of medical imaging data, images, files, or the like. Alternatively, or in addition the determination module 410 may use software and/or systems that implement one or more artificial intelligence methods (e.g., machine learning and/or neural networks) for deriving, determining, or extrapolating, anatomic data from medical imaging or the bone model. In one embodiment, the determination module 410 may perform an anatomic mapping of the bone model 404 to determine each unique aspect of the intended osteotomy procedure and/or bone resection and/or bone translation. The anatomic mapping may be used to determine coordinates to be used for an osteotomy procedure, position and manner of resections to be performed either manually or automatically or using robotic surgical assistance, a width for bone cuts, an angle for bone cuts, a predetermined depth for bone cuts, dimensions and configurations for resection instruments such as saw blades, milling bit size and/or speed, saw blade depth markers, and/or instructions for automatic or robotic resection operations.

In one embodiment, the determination module 410 may use advanced computer analysis system such as image segmentation to determine the anatomic data. The determination module 410 may determine anatomic data from one or more sources of medical imaging data, images, files, or the like. The determination module 410 may perform the image segmentation using 3D modeling systems and/or artificial intelligence (AI) segmentation tools. In certain embodiments, the determination module 410 is configured to identify and classify portions of bone based on a condition of the bone, based on the bone condition. Such classifications may include identifying bone stability, bone density, bone structure, bone deformity, bone structure, bone structure integrity, and the like. Accordingly, the determination module 410 may identify portions or sections or one or more bones based on a quality metric for the bone. Advantageously, that determination module 410 can identify high quality bone having a viable structure, integrity, and/or density versus lower quality bone having a nonviable structure, integrity, and/or density and a plurality of bone quality levels in between.

Accordingly, the determination module 410 can guide a surgeon to determine which areas of one or more bones of a patient are within a "soft tissue envelope" (bone of undesirable quality) as that bone relates to a particular deformity or pathology. Identifying the quality of one or more bones of the patient can aid a surgeon in determining what type of correction or adjustment is needed. For example, an ulceration that occurs due to a boney deformity can be mapped using the determination module 410 in a way that a correction can be performed to correct the deformity and reduce pressure to an area and address the structures that were causing the pressure ulceration/skin breakdown.

In addition, the determination module 410 and/or another component of the apparatus 402 can be used to perform anatomic mapping which may include advanced medical imaging, such as the use of CT scan, ultrasound, MRI, X-ray, and bone density scans can be combined to effectively create an anatomic map that determines the structural integrity of the underlying bone.

Identifying the structural integrity of the underlying bone can help in determining where bone resections (e.g., osteotomies) can be performed to preserve the densest bone in relation to conditions such as Charcot neuropathic, arthropathy where lesser dense bone can fail and collapse. It is well documented in the literature that failure to address and remove such lesser dense bone can ultimately lead to failure of a reconstruction and associated hardware.

The present disclosure provides, by way of at least the exemplary system 400, an anatomic map that can be part of anatomic data. The anatomic map can combine structural, deformity, and bone density information and can be utilized to determine the effective density of bone and help to determine where bone should be resected in order to remove the lesser dense bone while maintaining more viable bone to aid in the planning of the osteotomy/bone resection placement.

The location module 420 determines or identifies one or more recommended locations and/or trajectory angles for deployment of an instrument and/or soft tissue based on the anatomic data 412 and/or the bone model 404. In one embodiment, the location module 420 may compare the anatomic data 412 to a general model that is representative of most patient's anatomies and may be free from deformities or anomalies. The location module 420 can operate autonomously and/or may facilitate input and/or revisions from a user. The location module 420 may be completely automated, partially automated, or completely manual. A user may control how automated or manual the determining of the location and/or trajectory angles is.

The provision module 430 is configured to provide a preliminary instrument model 438. The provision module 430 may use a variety of methods to provide the preliminary instrument model. In one embodiment, the provision module 430 may generate a preliminary instrument model. In the same, or an alternative embodiment, the provision module 430 may select a template instrument model for a tendon (or tendon substitute) deployment procedure configured to enable locating the position and/or providing the trajectory provided by the location module 420. In one embodiment, the provision module 430 may select a template instrument model for a minimally invasive surgical (MIS) bunion correction procedure configured to enable locating the position and/or providing the trajectory for the fixation deployment. In one embodiment, the provision module 430 may select a template instrument model from a set of template instrument models (e.g., a library, set, or repository of template instrument models).

The registration module 440 registers the preliminary instrument model with one or more bones or other anatomical structures of the bone model 404. As explained above, registration is a process of combining medical imaging data, patient imaging data, and/or one or more models such that the preliminary instrument model can be used with the bone model 404.

The design module 450 designs a patient-specific instrument (or patient-specific instrument model) based on the preliminary instrument model. The design operation of the design module 450 may be completely automated, partially automated, or completely manual. A user may control how automated or manual the designing of the patient-specific instrument (or patient-specific instrument model) is.

The manufacturing module 460 may manufacture a patient-specific instrument 406 using the preliminary instrument model. The manufacturing module 460 may use a patient-specific instrument model generated from the preliminary instrument model. The manufacturing module 460 may provide the patient-specific instrument model to one or more manufacturing tools and/or fabrication tool (e.g., additive and/or subtractive). The patient-specific instrument model may be sent to the tools in any format such as an STL file or any other CAD modeling or CAM file or method for data exchange. In one embodiment, a user can adjust default parameters for the patient-specific instrument such as types and/or thicknesses of materials, dimensions, and the like before the manufacturing module 460 provides the patient-specific instrument model to a manufacturing tool.

Effective connection of the guide to one or more bones can ensure that surgical steps are performed in desired locations and/or with desired orientations and mitigate undesired surgical outcomes.

Figure 5:
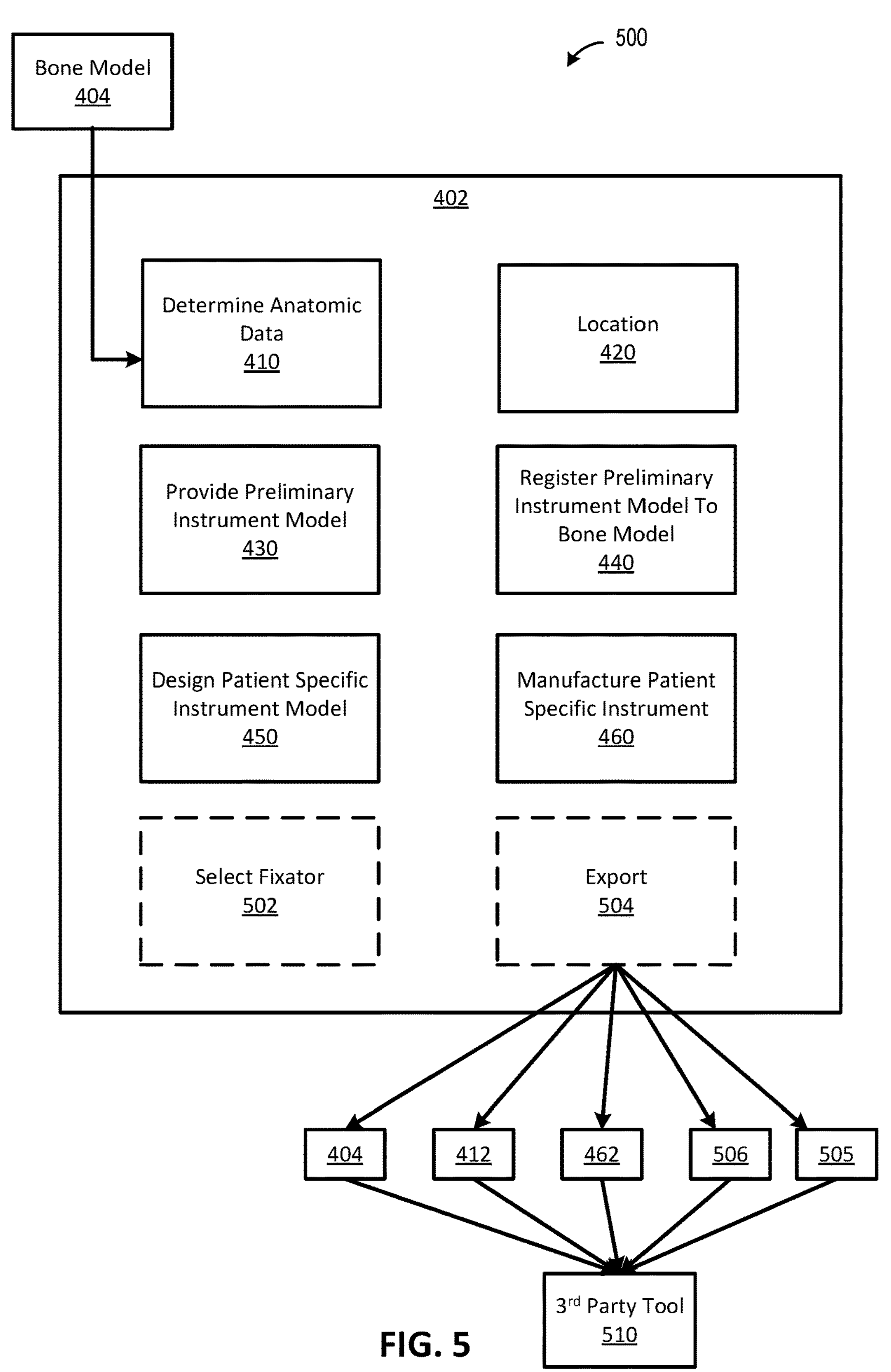
FIG. 5 illustrates an exemplary system configured to generate one or more patient-specific instruments, according to one embodiment.

FIG. 5 illustrates an exemplary system 500 configured to generate one or more patient-specific instruments configured to correct a bone condition, according to one embodiment. The system 500 may include similar components or modules to those described in relation to FIG. 4. In addition, the system 500 may include a fixator selector 502 and/or an export module 504.

The fixator selector 502 enables a user to determine which fixator(s) to use for a MIS bunion correction procedure planned for a patient. In one embodiment, the fixator selector 502 may recommend one or more fixators based on the bone model 404, the location, the trajectory, or input from a user or a history of prior MIS bunion correction procedures performed. The fixator selector 502 may select a fixator model from a set of predefined fixator models or select a physical fixator from a set of fixators. The fixators may include a plate and associated accessories such as screws, anchors, and the like.

In one embodiment, the fixator selector 502 includes an artificial intelligence or machine learning module. The artificial intelligence or machine learning module is configured to implement one or more of a variety of artificial intelligence modules that may be trained for selecting fixator(s) based on anatomic data 412 and/or other input parameters. In one embodiment, the artificial intelligence or machine learning module may be trained using a large data set of anatomic data 412 for suitable fixator(s) identified and labeled in the dataset by professionals for use to treat a particular condition. The artificial intelligence or machine learning module may implement, or use, a neural network configured according to the training such that the artificial intelligence or machine learning module is able to select or recommend suitable fixator(s).

The export module 504 is configured to enable exporting of a patient-specific instrument model 462 for a variety of purposes including, but not limited to, fabrication/manufacture of a patient-specific instrument 406 and/or fixator(s), generation of a preoperative plan, generation of a physical bone model matching the bone model 404, and the like. In one embodiment, the export module 504 is configured to export the bone model 404, anatomic data 412, a patient-specific instrument model 462, a preoperative plan 506, a fixator model 508, or the like. In this manner the custom instrumentation and/or procedural steps for a procedure (e.g., a graft harvesting procedure, minimally invasive surgical (MIS) procedure, or the like) can be used in other tools. The preoperative plan 506 may include a set of step by step instructions or recommendations for a surgeon or other staff in performing a procedure (e.g., a graft harvesting procedure, minimally invasive surgical (MIS) procedure, or the like). The preoperative plan 506 may include images and text instructions and may include identification of instrumentation to be used for different steps of the procedure (e.g., a graft harvesting procedure, minimally invasive surgical (MIS) procedure, or the like). The instrumentation may include the patient-specific instrument 406 and/or one or more fixators/fasteners. In one embodiment, the export module 504 may provide a fixator model which can be used to fabricate a fixator for the procedure.

The exports (404, 412, 462, 506, and 508) may be inputs for a variety of 3rd party tools 510 including a manufacturing tool, a simulation tool, a virtual reality tool, an augmented reality tool, an operative procedure simulation tool, a robotic assistance tool, and the like. A surgeon can then use these tools when performing a procedure or for rehearsals and preparation for the procedure. For example, a physical model of the bones, patient-specific instrument 406, and/or fixators can be fabricated, and these can be used for a rehearsal operative procedure. Alternatively, a surgeon can use the bone model 404, preliminary instrument model 438, and/or a fixator model to perform a simulated procedure using an operative procedure simulation tool.

Referring now to FIGS. 3-5, certain methods, systems, and/or apparatuses a disclosed herein for preparing for, planning, outlining, one or more surgical procedures. Alternatively, or in addition, the methods, systems, and/or apparatuses a disclosed herein can be used for preoperative development and design of instrumentation and/or for preoperative rehearsal and/or instruction of a surgeon before the surgical procedure is initiated. For example, a surgeon can use the method 300, bone model(s) 404, patient instrument(s) 406, system 400, and/or apparatus 402 to perform a mock surgical procedure virtually before an actual surgical procedure.

These techniques and/or technologies can greatly advance the medical field and provide valuable instruction and experience to a surgeon prior to an actual surgical procedure. Furthermore, these techniques and/or technologies are made effective owing to the accuracy and precision of the models because of the fidelity of the medical imaging of the patient anatomy. This virtual modeling of patient anatomy has become very accurate and helpful, particularly for hard tissue such as bones and the surfaces of these bones.

Unfortunately, the fidelity and accuracy of these models is not as advanced with respect to the modeling of soft tissue of a patient such as sinews, skin, tendons, ligaments, muscles, fat, and the like. Thus, rehearsal of a surgical procedure, particularly one that includes translating and/or reorienting one or more bone fragments has limited benefit. In such cases, because the surgeon cannot predict or know beforehand how much movement and reorientation the soft tissue of a patient will permit, the surgeon needs to be able to revise or adapt a surgical procedure intraoperatively to achieve optimal outcomes. The system, apparatus, and methods of the present disclosure enable a surgeon to make intraoperative adjustments to surgical plan based on what the surgeon learns during the surgery.

The present disclosure leverages the use of models, such as computer models, and particularly models of a specific patient to provide and/or generate instrumentation, implants, and/or surgical plans that advanced patient care. Advantageously, these models are unique and customized for a particular patient. Thus, the models reflect the actual anatomical features and aspects of the patient.

However, the utility and helpfulness of the models, methods, systems, and/or apparatuses of FIGS. 3-5, is dependent on how effectively a surgeon can navigate within, on, or in relation to one or more anatomical references or anatomical features of a patient such that the steps of the surgical procedure can be performed on a patient in the same manner as those modeled using models of the anatomy of the patient. This process of navigation is referred to as a mapping or translation between the virtual or model environment to a physical or real world environment that includes the patient anatomy and the operating field.

Advantageously, the models, methods, systems, and/or apparatuses of the present disclosure facilitate mapping or translating between a virtual or model environment and/or instrumentation to a physical or real world environment for a surgical procedure. The present disclosure provides this feature or benefit by providing an apparatus, system, and method, that enables a surgeon to identify, create, form, and/or use reference feature for a surgical procedure. The reference feature provides a reference and/or starting point on, in, or associated with anatomy of a patient such that steps, stages, features, or aspects planned and configured within the model can be accurately performed on, with, or to the anatomy of the patient. In certain embodiments, one or more steps of a surgical procedure can be done in connection with or in relation to the reference feature.

The reference feature facilitates moving from one coordinate system or frame of reference in a virtual environment to a position, location, frame of reference, environment, or orientation on, or in, an actual object, structure, device, apparatus, anatomical structure, or the like. Advantageously, the reference feature can coordinate objects, models, or structures in a digital or virtual model or representation with corresponding objects or structures (e.g., anatomical structures) of actual physical objects or structures. Said another way, the reference feature can serve to map from a virtual or modeled object to an actual or physical object.

Advantageously, the embodiment of the present disclosure include features and aspects that assist a surgeon in locating at least one reference feature, which can then be used in one or more stages of a surgical procedure. In certain embodiments, the actual instruments fabricated using the present disclosure may include one or more references (e.g., a model references). The one or more model instruments may use the one or more references to position and/or orient the one or more model instruments such that other steps of a surgical procedure can be performed in relation to those one or more model instruments and/or model references. Certain model references may key off or related to anatomical references of modeled anatomical body parts. The reference feature(s) correspond to the model references and together enable a surgeon to identify reference features on actual anatomy of a patient for a surgical procedure.

Figures 6A, 6B:
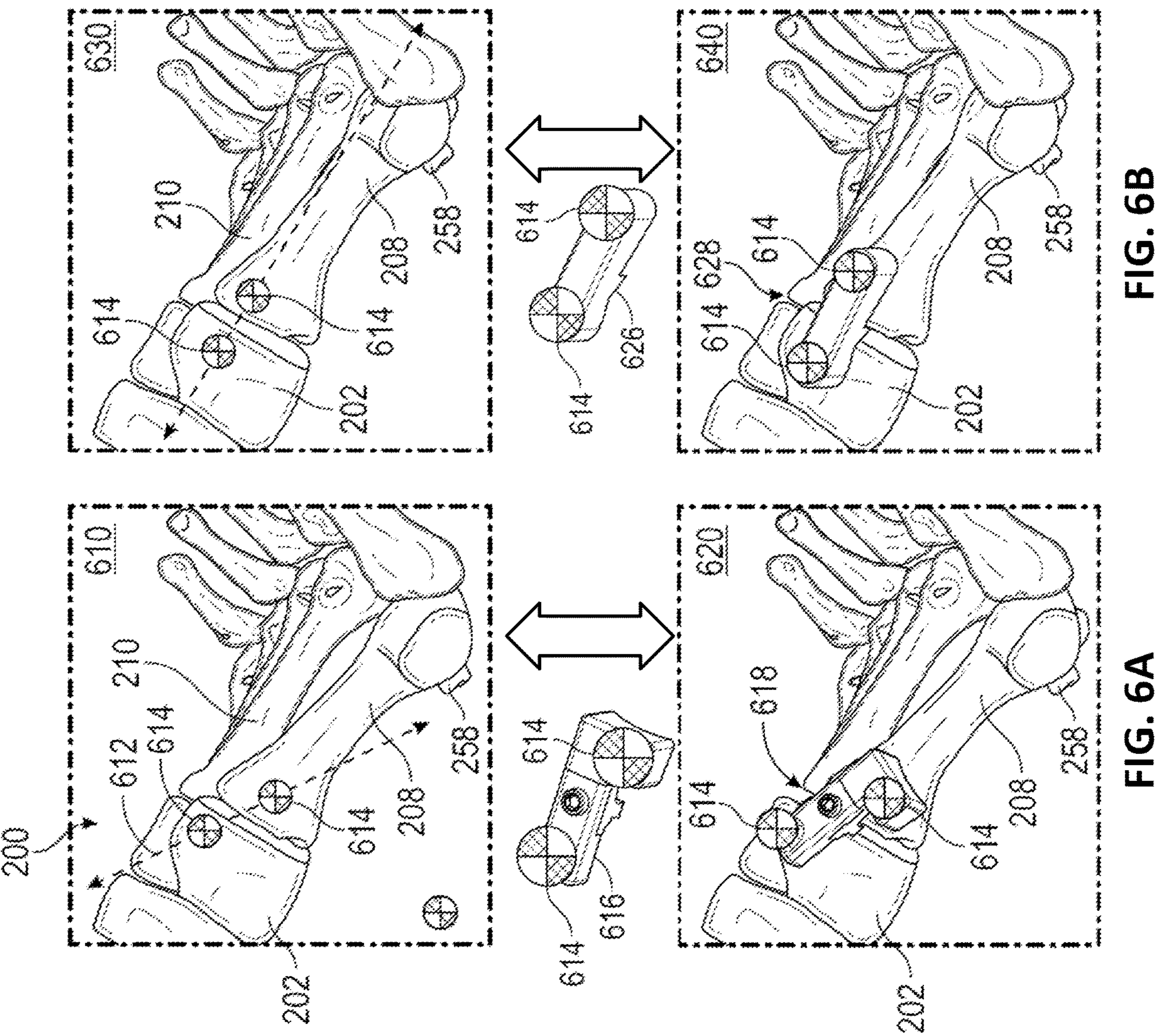
FIGS. 6A and 6B illustrates a mapping between a virtual model and physical anatomy of a patient's foot.

FIGS. 6A and 6B illustrate a couple of examples of a mapping between a virtual model and physical anatomy of a patient's foot. FIG. 6A illustrates a model or virtual pane 610 and an actual or physical pane 620.

The virtual pane 610 illustrates a view and/or representation of one or more models of bones of a specific patient. Models of soft tissue are not shown for clarity and to facilitate the description. Alternatively, or in addition, as explained above, models of soft tissue are not as reliable as desired for use in planning the surgical procedure. The virtual pane 610 includes a bone model 404 that includes a model of a medial cuneiform 202, a model of a first metatarsal 208, a model of a second metatarsal 210, etc. Virtual pane 610 illustrates that the foot 200 has a deformity. Specifically, the first metatarsal 208 extends more medial than desired; the first metatarsal 208 is not substantially parallel to the second metatarsal 210.

The physical pane 620 illustrates a view of one or more actual bones of a specific patient. Soft tissue is not shown for clarity and to facilitate the description. The physical pane 620 illustrates actual bones of the same patient used to create the models of virtual pane 610. Physical pane 620 shows a medial cuneiform 202, a first metatarsal 208, a second metatarsal 210, etc. Physical pane 620 shows the patient's foot 200 has a deformity. Specifically, the first metatarsal 208 extends more medial than desired; the first metatarsal 208 is not substantially parallel to the second metatarsal 210.

The virtual pane 630, like virtual pane 610 illustrates a view and/or representation of one or more models of bones of this specific patient. Models of soft tissue are not shown. The virtual pane 630 includes the same models as virtual pane 610 and illustrates the foot 200 after the deformity has been addressed. Specifically, the model of the first metatarsal 208 extends more parallel to the model of the second metatarsal 210 than before.

The physical pane 640, like physical pane 620 illustrates a view of the same actual bones as physical pane 620. Physical pane 640 shows the patient's foot 200 after the deformity has been addressed. Specifically, the first metatarsal 208 extends more parallel to the second metatarsal 210 than before.

In this example, a surgeon has decided to do an arthrodesis procedure on the 1$^{st}$ TMT joint (between the medial cuneiform 202 and the first metatarsal 208). In virtual pane 610, a surgeon or other user may identify an axis 612 between a model of the medial cuneiform 202 and a model of the first metatarsal 208 which the user wants to use as a reference for checking the outcome of a surgical procedure near the final steps of the procedure. It should be noted that rather than aligning the axis 612 with a long axis of the first metatarsal 208, the axis 612 in virtual pane 610 extends more medial. In one embodiment, this difference may be because the surgeon intends to reorient the first metatarsal 208 and rotate the first metatarsal 208 such that sesamoids 258 are directed more plantar once the surgical procedure is completed. Virtual pane 630 illustrates that once the procedure is completed the axis 612 will align with the long axis of the model of the first metatarsal 208 and the model of the first metatarsal 208 will be substantially parallel to the model of the second metatarsal 210.

FIGS. 6A and 6B illustrate one example of embodiment of one or more instruments that can be used to assist a surgeon in performing the surgery in a manner that most closely matches the desired or planned surgery set out using models of the bones and/or models of instruments. In particular, the present disclosure in this example provides one or more instruments that bridge the divide between the virtual environment and the physical environment that the surgeon will work with during the surgery.

Advantageously, the present disclosure provides a patient-specific instrument model 462 that can be readily fabricated to provide a patient-specific instrument 406. In this example, a model navigation guide 616 and corresponding actual patient-specific navigation guide 618 and a model positioning guide 626 and corresponding actual patient-specific positioning guide 628 are illustrated and provided. Advantageously, the patient-specific instrument model 462 and patient-specific instrument 406 share one or more common features and/or aspects that enable the patient-specific instrument 406 to serve as a navigation guide that helps a surgeon locate a desired position and/or orientation for one or more instruments in relation to anatomy of a patient during a surgical procedure.

In the illustrated embodiment, the patient-specific instrument model 462 includes one or more markers 614. The markers 614 serve to identify a location for a reference feature. In one embodiment, markers 614 may be a form of fiducials. FIGS. 6A and 6B illustrate where on a model of a patient's anatomy a marker is in panes 610/630 in relation to where those same markers will be on actual anatomy in panes 620/640.

Those of skill in the art will appreciate that the markers 614 may be implemented using a variety of different structures. In one embodiment, pin locations or holes for temporary fasteners, such as K-wires may be defined in a model navigation guide 616 and/or model positioning guide 626 that serve as markers 614 or model references. In addition, pin locations or holes for temporary fasteners may be defined in an actual patient-specific navigation guide 618 and/or actual patient-specific positioning guide 628 that serve as markers 614 or reference features. Alternatively, or in addition, the guide pins (e.g., fasteners) within the holes may serves as reference features.

Alternatively, or in addition, a patient-specific instrument model 462 may include other features that are part of, or cooperate with a model reference or anatomical reference. In one embodiment, the model instrument may include a feature such as a tissue engagement surface (e.g., a bone engagement surface) or a registration key that is configured to engage with the tissue in a single position and/or orientation. Thus, in certain embodiments, holes in a patient-specific instrument model 462 and/or other features such as tissue engagement surface can serve as a model reference or marker for a reference feature. Advantageously, the corresponding patient-specific instrument 406 includes the marker and/or other patient-specific features that ensure a surgeon positions the instrument in the desired location in relation to the actual anatomy of the patient during the surgical procedure.

In the illustrated embodiment, of FIGS. 6A and 6B, the markers 614 may be guide pin holes for guide pins that may serve as reference features for at least an initial step in a surgical procedure and/or may serve as references for one or more subsequent steps in the surgical procedure. those of skill in the art will appreciate that other embodiments of markers 614 may be used within the scope of the present disclosure. FIGS. 6A and 6B that with the patient-specific features and/or markers 614 of the present disclosure a surgeon can position the actual patient-specific navigation guide 618 and/or actual patient-specific positioning guide 628 in desired positions on the anatomy. With the instruments in position (a position that corresponds to, and/or matches, the position of the model instrument in the model), a surgeon can mark, identify, form, or create the reference features that successfully map model references to anatomical references on a patient.

Figure 7:
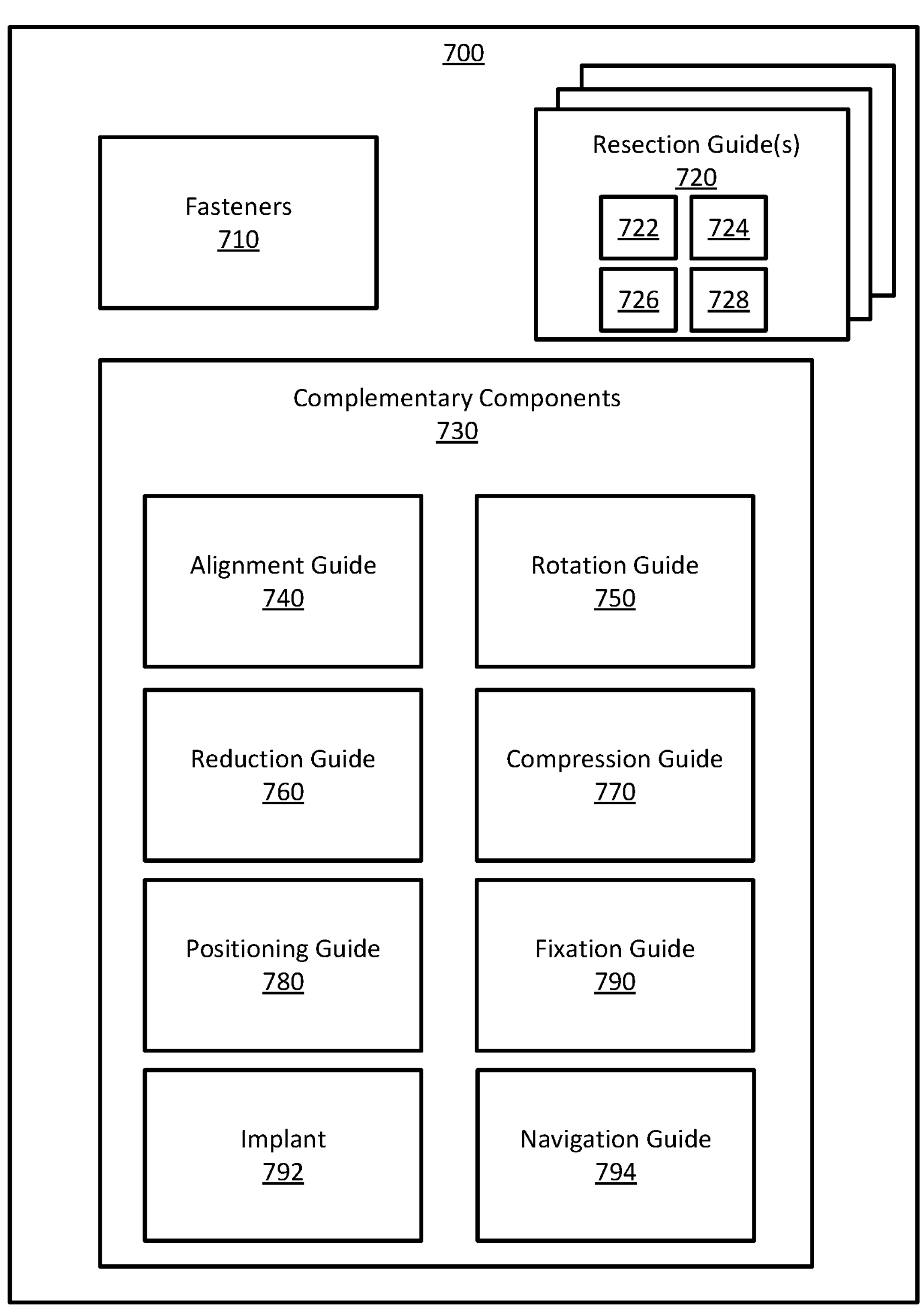
FIG. 7 illustrates an exemplary system for remediating a condition present in a patient's foot, according to one embodiment.

FIG. 7 illustrates an exemplary system 700 for remediating a condition present in a patient's foot, according to one embodiment. The system 700 can include one or more fasteners 710, one or more resection guides 720, and one or more complementary components 730. While a system 700 can be used for a variety of procedures, one or more features, components, and/or aspects of the system 700 may be particularly suited for one or more osteotomies on one or more bones of a structure such as a patient's foot, ankle, wrist, hand, shoulder, or the like.

In certain embodiments, the one or more fasteners 710 can include one or more permanent fasteners and/or one or more temporary fasteners. Typically, the fasteners 710 may be used during a variety of different steps of a procedure. Temporary fasteners are often used because they can securely hold bone or parts/fragments of bones while steps of the procedure are conducted. A common temporary fastener that can be used with system 700 is a K-wire, also referred to as a pin, guide pin, and/or anchor pin. Permanent fasteners 710 such as bone screws, bone staples, sutures, tethers or the like may also be used in a surgical procedure.

The one or more resection guides 720 assist a surgeon in performing different resection or dissection steps for an osteotomy or other procedure. In certain embodiments, a resection guide 720 includes one or more resection features 722 and one or more bone attachment features 724. The resection features 722 can take a variety of forms and/or embodiments. In one embodiment, the resection features 722 take the form of a cut channel or slot or other opening.

The resection features 722 provide a guide for a surgeon using a cutting tool to resect a bone, one or more bones, or other tissues of a patient. In certain embodiments, the resection features 722 may guide a surgeon in performing a resection, and osteotomy, and/or a dissection.

Similarly, the bone attachment features 724 can take a variety of forms and/or embodiments. The bone attachment features 724 may serve to secure the resection guide 720 and/or other instrumentation to one or more bones and/or one or more other structures. Often, a bone attachment feature 724 can take the form of a hole in and/or through the resection guide 720 together with a temporary fastener such as a K-wire, pin, or guide pin.

The bone attachment features 724 facilitate attachment (at least temporarily) of a resection guide 720 to one or more bones, or bone fragments, of a patient. The bone attachment features 724 may include any of a wide variety of fasteners or structures including, but not limited to, holes, spikes, prongs, screws, fastening devices, and/or the like. Effective connection of the resection guide 720 to one or more bones across a joint and/or to one or more bones can ensure that cut surfaces are formed in desired locations and orientations and mitigate removal of hard tissue and/or soft tissue in undesired locations and/or orientations.

In certain embodiments, a resection guide 720 may include one or more bone engagement surfaces 726 and/or one or more landmark registration features 728. In certain embodiments, a landmark registration feature 728 may extend from one or more sides or ends of a resection guide 720 and engage with one or more landmarks of a bone or joint or anatomical structure of a patient. Registration of the landmark registration feature 728 to a landmark of a bone or joint can serve to confirm and/or ensure that a surgeon has located a desired placement and/or orientation for a resection guide 720.

In certain embodiments, the bone engagement surfaces 726 are patient-specific: contoured to match a surface of: one or more bones and/or bone surfaces the resection guide 720 contacts during the procedure or one or more joints proximal to the resection guide 720 during the procedure. Alternatively, or in addition, the bone engagement surface 726 may not be patient-specific, and may, or may not, contact a bone surface during use of the resection guide 720. In one embodiment, a skin contact surface may be used in addition to, or in place of, a bone engagement surface. Those of skill in the art appreciate that one or more sides of any of the members of the system 700 may include one or more bone engagement surfaces 726. Consequently, one or more sides of the fasteners 710, the resection guide(s) 720, the complementary components 730, and/or the implants 792 may include one or more bone engagement surfaces 726.

In certain embodiments, the resection guides 720 and/or aspects of the resection guides 720 may be integrated into other components and/or instruments, such as a pin guide, a trajectory guide, an alignment guide, or the like.

The complementary components 730 serve to assist a surgeon during one or more steps of a procedure. Those of skill in the art appreciate that a number of components can serve as complementary components 730. One or more of the features, functions, or aspects of the complementary components 730 can include patient-specific features.

Examples of complementary components 730 include, but are not limited to, an alignment guide 740, a rotation guide 750, a reduction guide 760, a compression guide 770, a positioning guide 780, a fixation guide 790, and/or one or more implants 792. In general, the complementary components 730 serve to assist a surgeon in performing the function included in the name of the complementary component 730. Thus, an alignment guide 740 can help a surgeon align bones, parts of bones, or other parts of a patient as part of a procedure. A rotation guide 750 can help a surgeon rotate one or more bones, parts of bones, or other parts of a patient as part of a procedure. In one embodiment, a rotation guide 750 may hold one bone fragment stable while another bone fragment is rotated into a desired position.

A reduction guide 760 can help a surgeon position and/or orient one or more bones, parts of bones, or other parts of a patient as part of a procedure in order to reduce the bone, bones, bone parts, or other parts and/or in order to position and/or orient the bone, bones, bone parts, or other parts to a desired position and/or orientation. In certain embodiments, aspects and/or features of a reduction guide 760 can be integrated into one or more other components of an osteotomy system 700, such as components of the complementary components 730. A compression guide 770 can help a surgeon compress one or more bones, parts of bones, or other parts of a patient together or against an implant as part of a procedure. In certain embodiments, compression guide 770 can be a separate instrument such as a compressor and/or a combined compressor/distractor. The compressor/distractor can be used to compress two or more cut faces formed by an osteotomy until fixation is deployed or distract bones or parts of bones involved in a procedure. In certain embodiments, a compression guide 770 may serve a dual purpose as both a compression guide 770 and as a positioning guide 780. The same instrument may be used to both translate and/or rotate bones or bone fragments and compress two or more cut faces formed by an osteotomy until fixation can be deployed.

A positioning guide 780 (also referred to as a positioner) can help a surgeon position one or more bones, parts of bones, or other parts of a patient as part of a procedure. For example, a positioning guide 780 may hold one bone or bone fragment stable and hold one or more other bone fragments in a desired position while permanent or temporary fixation is deployed. In certain embodiments, the positioning guide 780 may hold bone fragments in a reduced position, and thus may function as both a positioning guide 780 and/or a reduction guide 760.

In certain embodiments, the positioning guide 780 may be designed and fabricated to be patient-specific. The patient-specific aspects can include a patient-specific bone engagement surface, a predefined angle for reorienting one or more bone or bone parts within one or more planes, a predefined position for bone attachment features 724 or fasteners 710, a predefined or patient-specific offset or amount of translation that is provided, or the like. Alternatively, or in addition, the positioning guide 780 may be selected from a kit, collection, or repository of a number of positioning guides 780: each having a different configuration for one or more aspects/attributes of the positioning guide 780. For example, each member of the repository/kit may include a different positioning angle (repositioning or correction angle), the angles may differ by 2 degrees for example. In such an embodiment, each positioning guide 780 may not be patient-specific to a particular patient but may provide the desired amount of positioning to meet the goals of the surgeon. In certain embodiments, a preoperative plan generated based on the present disclosure may include a recommendation for the positioning guide 780 to be used, even if the recommended positioning guide 780 is not patient-specific to the particular patient.

A fixation guide 790 can help a surgeon in completing one or more temporary or permanent fixation steps for one or more bones, parts of bones, or other parts of a patient as part of a procedure. The fixation guide 790 may include and/or may use one or more components of a fastener or fixation system including implant hardware of the fastener or fixation system.

Those of skill in the art will appreciate that the other complementary components 730 may each have functions, purposes, and/or advantages with respect to one or more anatomical parts of the patient. Alternatively, or in addition, the other complementary components 730 may each have functions, purposes, and/or advantages with respect to one or more instruments and/or one or more anatomical parts of the patient. For example, a trajectory guide may be a type of alignment guide 740 in that the trajectory guide facilitates alignment of fixation with the desired location and/or trajectory/orientation with respect to one or more anatomical parts of the patient. Alternatively, or in addition, a trajectory guide may also be considered a type of fixation guide 790 because the trajectory guide facilitates deployment of one or more fasteners 710.

Advantageously, the system 700 can help a surgeon overcome one or more of the challenges in performing an osteotomy procedure, particularly on bones of a hand or of a foot of a patient, such as on the forefoot, midfoot, or hindfoot. One challenge during an osteotomy procedure can be maintaining control of, and/or position, and/or orientation of a bone, one or more bones, and/or bone pieces/fragments, particularly once a resection or dissection is performed. Advantageously, the fasteners 710, resection guide(s) 720, and/or complementary components 730 can be configured to assist in overcoming this challenge.

Advantageously, system 700 can help a surgeon in positioning, placing, and/or orienting a resection guide accurately. Modern techniques may include preoperative planning, simulation, or even practice using computer models, 3D printed models, virtual reality systems, augmented reality systems or the like. However, simulations and models are still different from actually positioning a resection guide on a patient's bone, joint, or body part during the procedure. System 700 can include a number of features, including patient-specific features, to assist the surgeon with the positioning. In one embodiment, the resection guide 720 can include one or more landmark registration features 728.

Advantageously, the system 700 can help a surgeon in securing guides of the osteotomy system 700, such as a resection guide, as well as how to readily remove the guide (e.g., resection guide) without disturbing a reduction, shifting, reorienting, or repositioning one or more bones or parts of bones while removing the guide. In certain embodiments, the system 700 is configured to permit removal of a guide while keeping temporary fasteners in place for use in subsequent steps of an osteotomy procedure. Alternatively, or in addition, system 700 may facilitate positioning of temporary fasteners during one step of a wedge osteotomy procedure for use in a subsequent step of the wedge osteotomy procedure. Removal of a guide during an osteotomy procedure can be particularly challenging where translation and/or rotation of the bones involved in the osteotomy procedure is required for the success of the osteotomy procedure. Advantageously, system 700 accommodates translation and/or rotation of the bones during the osteotomy procedure while facilitating a successful outcome for the osteotomy procedure.

Advantageously, the components of the system 700 can be specifically designed for a particular patient. Alternatively, or in addition, the components of the system 700 can be specifically designed for a class of patients. Each of the components of system 700 can be designed, adapted, engineered and/or manufactured such that each feature, attribute, or aspect of the component is specifically designed to address one or more specific indications present in a patient. Advantageously, the cuts made for the osteotomy procedure can be of a size, position, orientation, and/or angle that provides for an optimal osteotomy with minimal risk of undesirable resection. In one embodiment, the components of system 700 can be configured such that an osteotomy is performed that enables a correction in more than one plane in relation to the parts of the body of the patient. For example, cut channels or resection features 722 in a resection guide 720 can be oriented and configured such that when the bones are fused/fixated the correction results from translation, rotation, and/or movement of bones or bone parts in two or more planes (e.g., sagittal and transverse) once the fragments or bones are reduced.

In certain embodiments, the exemplary system 700 may include a plurality of fasteners 710, resection guides 720, and/or complementary components 730. For example, a surgeon may plan to resect a plurality of osteotomies from the bone(s) in order to accomplish a desired correction. In one example, one or more wedge segments may be resected from a medial side of a patient's foot and another one or more wedge segments may be resected from a lateral side of the patient's foot. These wedge segments may extend part way into the foot, or through from one side of the foot to the other. Of course, multiple wedge segments may be formed on one side of the foot as well.

Additionally, a surgeon may use one or more components in an exemplary system 700 to make multiple cuts in the bone(s). The multiple cuts may be centered over or around an apex of a deformity or positioned at other locations within the foot such that when the multiple cuts are made, any resected segments removed, or added bone void fillers introduced, and/or bones and/or bone fragments translated and/or rotated the combined angles, surfaces, removed segments, and/or added portions cooperate to provide a desired correction. Each of the components of the exemplary system 700 can be identified, defined, and reviewed using the apparatuses, systems, and/or methods of the present disclosure.

In certain embodiments, the components of system 700 may be made as small as possible to minimize the amount of soft tissue that is opened in the patient for the osteotomy procedure. Alternatively, or in addition, walls and/or sides of the components may be beveled and/or angled to avoid contact with other hard tissue or soft tissues in the operating field for the osteotomy procedure.

Those of skill in the art will appreciate that for certain osteotomy procedures a complementary component 730 may not be needed or a given complementary component 730 may be optional for use in the osteotomy procedure. Similarly, those of skill in the art will appreciate that certain features of the fasteners 710, resection guides 720, and/or complementary components 730 can be combined into one or more of apparatus or devices or may be provided using a plurality of separate devices.

Figure 8:
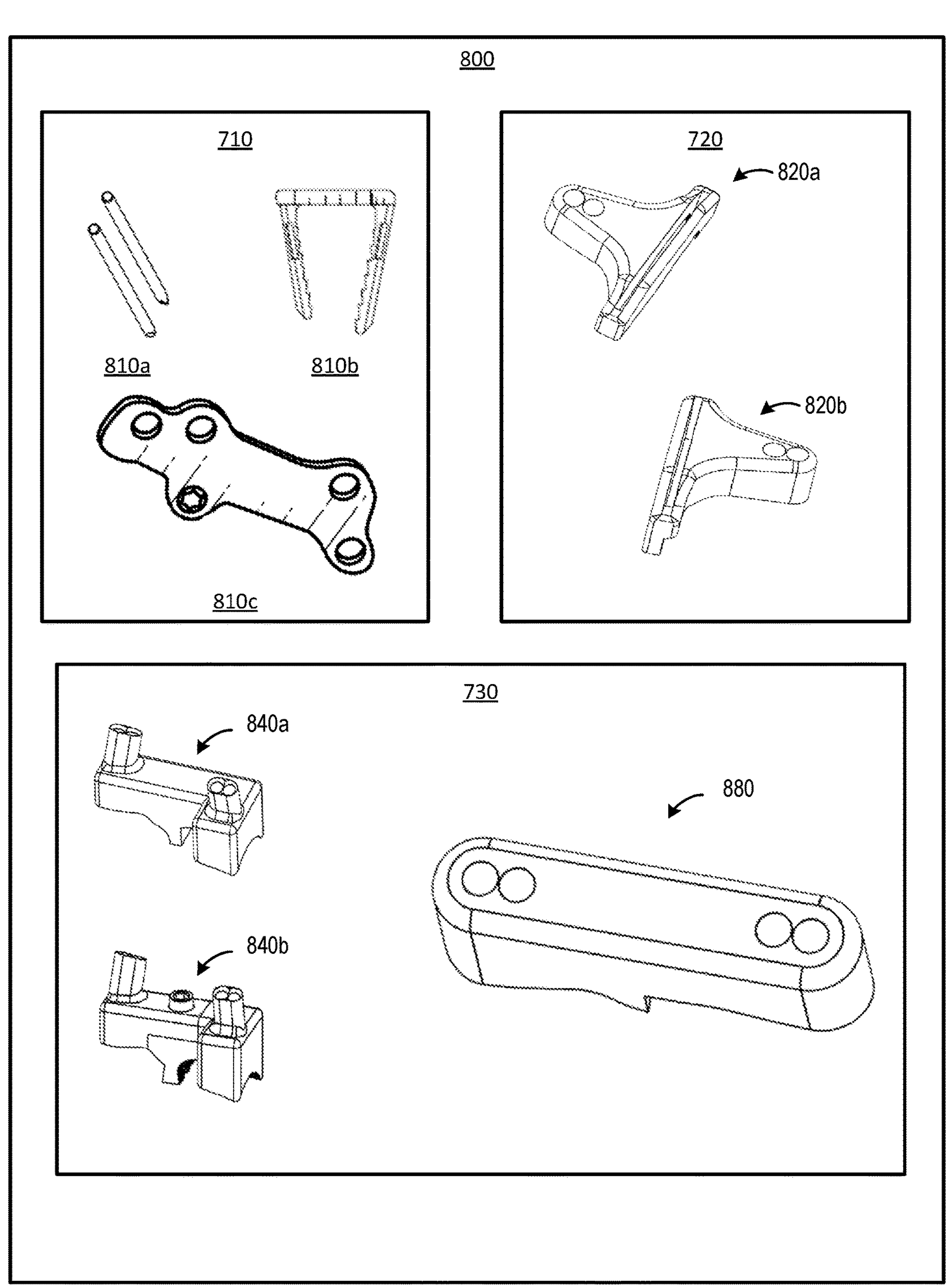
FIG. 8 illustrates an exemplary system for an osteotomy, according to one embodiment.

FIG. 8 illustrates an exemplary system 800 for an osteotomy, according to one embodiment. Those of skill in the art will appreciate that embodiments of the present disclosure may be used for a through cut osteotomy, a wedge osteotomy, one or more osteotomies for an arthrodesis, or the like. An osteotomy using the exemplary system 800 can enable reorientation of the metatarsal to a more desired configuration or orientation, in some instances. In addition, the system 800 can be designed to address a desired degree of rotation of a bone of the patient using the instrumentation of the system 800. For example, certain instruments can be designed and fabricated to enable or facilitate rotation of a first metatarsal 208 about its long axis after an osteotomy in order to move sesamoids 258 to a more plantar facing orientation. Advantageously, because the amount of rotation can be determined prior to a surgical procedure, this amount of rotation can also be adjusted and revised before instrumentation is fabricated and/or a preoperative plan is completed. Alternatively, or in addition, accommodations can be made for using instruments that may permit a surgeon to use different instruments during surgery that enables the surgeon to adapt as they learn how much movement or adjustment soft tissue around a surgical site will permit. For example, a surgeon may include a plurality of the resection guides that can be interchanged during surgery to meet the needs of the patient and/or the surgeon.

The system 800 may include one or more fasteners 918, a resection guide (a proximal resection guide 820*a* and distal resection guide 820*b*), and one or more other complementary components 830, such as a navigation guide 840 (two embodiments are illustrated navigation guide 840*a* and navigation guide 840*b*; which may also serve as a pin positioning guide 840), and a positioning guide 880. Advantageously, the apparatus, system, and/or methods of the present disclosure enable the surgeon and/or patient to preplan each aspect of the surgical procedure. For example, which fasteners 918, which style and configuration of resection guide 820*a,b*, which navigation guide 840 and/or which positioning guide 880 will be used, can all be decided before the surgical procedure is scheduled.

In the illustrated embodiment, system 800 includes one or more guide pins, pins, or k-wires 918*a*, one or more staples 918*b*, one or more bone screws (not shown), and one or more bone plates 918*c*. Certain fasteners 918 may be used for temporary fixation while others may be used for permanent fixation. In one embodiment, the fasteners 918 are configured to single use. In one embodiment, the fasteners 918 may be provided in a surgical kit and a surgeon may choose which fasteners to use during the procedure. Alternatively, or in addition, the precision and accuracy of the present disclosure may enable a surgeon to select specific fasteners 918 to use as part of planning the surgical procedure. For example, a surgeon may choose a specific size and configuration of bone plate(s) 918*c* to be used.

In the illustrated embodiment, two separate resection guides, a proximal resection guide 820*a* and a distal resection guide 820*b* may be used. While those of skill in the art will appreciate that a single resection guide 820 can be used for an osteotomy of a cuneiform and a metatarsal, using two separate resection guides can provide certain advantages. As mentioned herein, modeling of hard tissue is highly accurate and precise while modeling of soft tissue is less predictable. Consequently, a surgeon may not know with sufficient certainty how soft tissue will respond to steps of a surgical procedure. Specifically, the surgeon may not know now much translation and/or rotation of tissues such as bones the soft tissue will permit until the surgeon is performing the surgery.

Advantageously, using two separate resection guides can enable a surgeon to adapt intraoperatively to the amount of rotation and/or translation the soft tissue will permit. Specifically, one resection guide may include a resection feature with a first angle for correction, a second resection guide may include a resection feature with a second angle for correction greater than the first, a third resection guide may include a resection feature with a third angle for correction greater than the second, and so forth. These different resection guides may be part of a kit available to the surgeon during the surgery. In this manner, a surgeon can choose a resection guide with a preferred angle for correction during the surgery.

In certain embodiments, both a proximal resection guide 820*a* and a distal resection guide 820*b* can include a resection feature that is angled at an angle that is not 90 degrees with respect to a long axis of the bone being cut. Alternatively, or in addition, only one of the resection guides 820 may include a resection feature that is angled at an angle that is not 90 degrees with respect to a long axis of the bone being cut and the other resection guide 820 may include a resection feature that is angled at an angle that is 90 degrees with respect to a long axis of the bone being cut. In certain embodiments, using a resection guide 820 with a resection feature that is angled 90 degrees relative to a long axis of the bone being cut can enable a surgeon to make an easier osteotomy of a bone using the resection guide 820. In addition, in certain embodiments, the osteotomy may be more precise and more accurate than using a resection guide 820 with a resection feature that is not angled 90 degrees relative to a long axis of the bone being cut.

Either or both of the resection guides 820 may be a custom patient-specific resection guides made for a particular patient and/or for a particular surgical procedure. Various aspects of the resection guides 820 may be patient-specific, including, but not limited to, an angle and/or orientation for a resection feature of the resection guide 820, a position of the resection feature, a depth of the resection feature, a size of the resection guide 820, a configuration and/or composition of a bone contacting surface such as a bone engagement surface of the resection guide 820, and the like.

In the illustrated embodiment, the resection guides 620 are for one or more osteotomies at a TMT joint between a metatarsal and a cuneiform. The system 800 illustrates alternative embodiments of different components to show that each part of the system 800 can be custom designed based on the needs of the patient, the type of surgical procedure, and/or the preferences of the surgeon. Advantageously, in certain embodiments, practically every aspect of the features, aspects, and/or attributes of the system 800 can be specified and/or ordered.

Different aspects and/or embodiments of the components of the system 800 are described in more detail herein. In one embodiment, the system 800 includes a set of proximal guide pins 918*a*, a set of distal guide pins 918*a*, a navigation guide 840, a proximal resection guide 820*a*, a distal resection guide 820*b*, and a positioning guide 880.

Figures 9A, 9B, 9C:
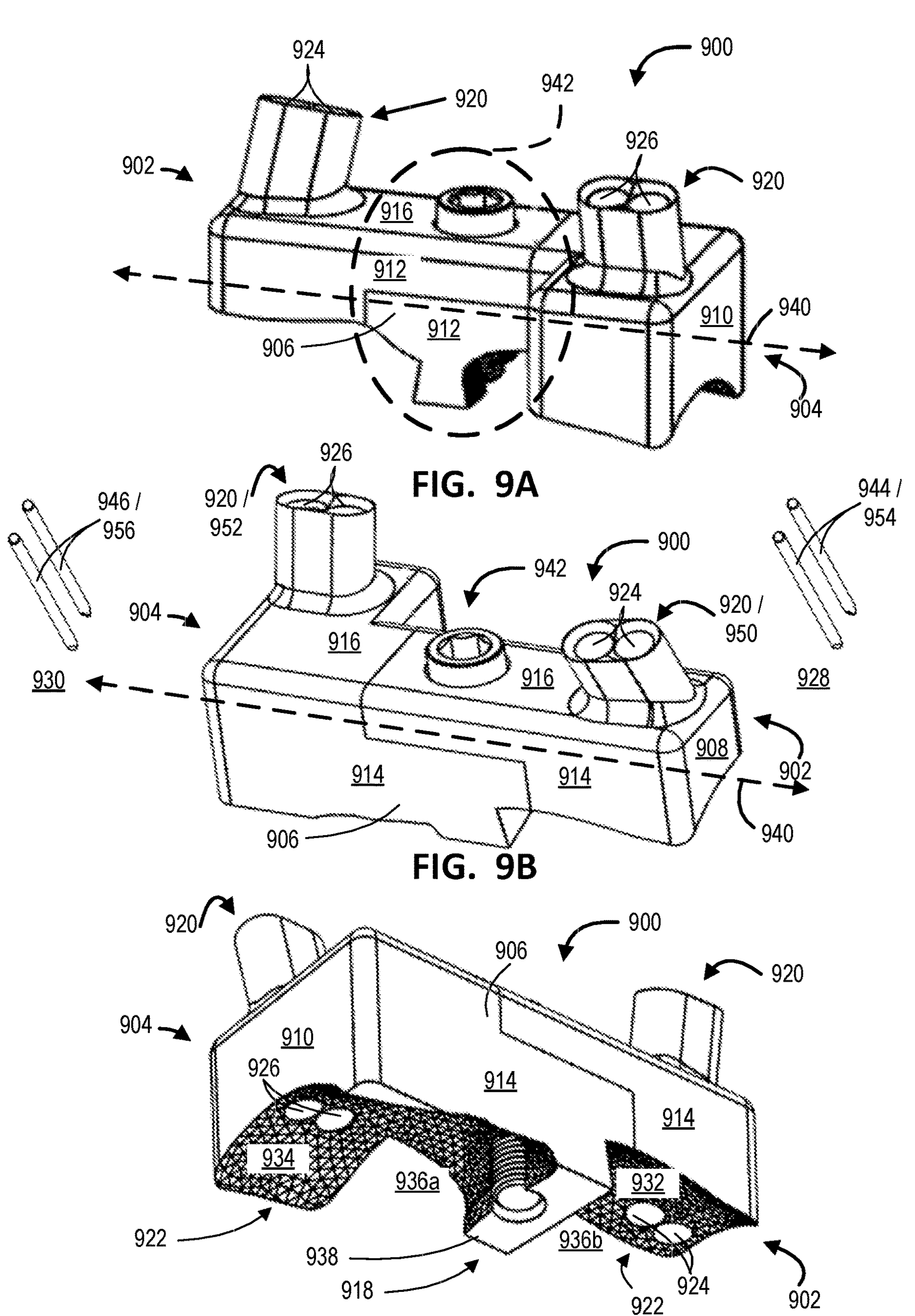
FIG. 9A illustrates a top perspective view from a medial side of a navigation guide according to one embodiment.
FIG. 9B illustrates a top perspective view from a lateral side of a navigation guide according to one embodiment.
FIG. 9C illustrates a bottom perspective view from an inferior side of a navigation guide according to one embodiment.

FIG. 9A illustrates a top perspective view from a medial side of a navigation guide 900 according to one embodiment. FIG. 9B illustrates a top perspective view from a lateral side of the navigation guide 900 according to one embodiment. FIG. 9C illustrates a bottom perspective view from an inferior side of the navigation guide 900 according to one embodiment.

The navigation guide 900 can be configured to position one or more temporary fasteners 918*a* (e.g., K-wires) for use in a procedure. Advantageously, in certain embodiments, the navigation guide 900 can include one or more features that facilitate proper positioning/registering of the navigation guide 900 to a desired location on one or more bones and/or transverse to a joint and thereby map from a virtual environment of models to a physical environment of a patient's anatomy for a surgical procedure.

The navigation guide 900 includes a proximal end 902, a distal end 904, with a body 906 between them. In one embodiment, The body 906 includes a proximal side 908, a distal side 910, a medial side 912, a lateral side 914, a superior side 916, and an inferior side 918. The proximal side 908 is the side closest to the core of the patient when the navigation guide 900 is in use. The distal side 910 is the side furthest from the core of the patient when the navigation guide 900 is in use. The medial side 912 is the side facing medially when the navigation guide 900 is in use. The lateral side 914 is the side facing laterally when the navigation guide 900 is in use. The superior side 916 is the side facing up away from the bone(s) when the navigation guide 900 is in use. The inferior side 918 is the side facing down, facing, and/or contacting the bone(s) (e.g., contacting a surface of one or more bones) when the navigation guide 900 is in use.

The navigation guide 900 may also include at least one marker 920 and a bone engagement surface 922. The marker 920 is a structure of the navigation guide 900 that facilitates translating features, aspects, structures, and/or other aspects of a virtual environment to a physical environment for a surgical procedure. In particular, the marker 920 identifies at least one location for a reference feature that can provide a reliable reference in the physical environment that maps or corresponds to the position and/or frame of reference in the virtual environment. In the illustrated embodiment, the marker 920 identifies a location for a reference feature that corresponds to a model reference of a bone (both a model bone and a physical bone) of a patient's foot.

In the illustrated embodiment, the marker 920 takes the form of a set of holes that extend from the superior side 916 to the inferior side 918 of the body 906. Specifically, in the illustrated embodiment, the marker 920 includes a set of proximal holes 924 and a set of distal holes 926. The angle and/or orientation of the set of proximal holes 924 and/or set of distal holes 926 extend through the body 906 may be patient-specific. In certain embodiments, the set of proximal holes 924 are configured to receive a set of proximal guide pins 928 and/or the set of distal holes 926 are configured to receive a set of distal guide pins 930. In the illustrated embodiment, the set of proximal holes 924 and/or set of distal holes 926 includes holes for two proximal guide pins 928 and holes for two distal guide pins 930 because use of two guide pins can prevent rotation of instruments that may slide over and/or anchor to the guide pins. Those of skill in the art will appreciate that where a set of structures is described herein this can include zero, one, two, three or more of the particular structure.

Those of skill in the art will appreciate that the marker 920 may be used to accept guide pins or may be used in other ways to identify reference features. In one embodiment, a marker 920 may be implemented as holes and those holes may be used as guides for a surgeon to drill holes, tunnels, or other openings in one or more bones of patient. The holes formed in the anatomy of the patient may then serve as reference features for a surgical procedure. In still another embodiment, the marker 920 may be a structure made from a material that is detectable by sensors on a surgical assistant such as a robotic surgical device. For example, the marker 920 may be magnetic and a robotic surgical device may sense the marker 920 and use the marker 920 to deploy guide pins or form holes in anatomy of a patient.

It should be noted that that marker 920, in certain embodiments, can include the set of proximal holes 924, the set of distal holes 926, the set of proximal guide pins 928, and/or the set of distal guide pins 930, each individually or in combination with one or more of the others. In one embodiment, the marker 920 is the set of proximal holes 924 and the set of distal holes 926. In another embodiment, the marker 920 is the set of proximal holes 924 and the set of proximal guide pins 928. In another embodiment, the marker 920 is the set of distal holes 926 and the set of distal guide pins 930. Alternatively, or in addition, the reference feature may include the set of proximal guide pins 928 and/or the set of distal guide pins 930, each individually or in combination with each other.

Advantageously, the marker 920 provides a convenient way for a surgeon to position and/or identify where one or more reference features are or should be with respect to anatomy of a patient to accurately map the virtual environment (model bones, model instruments, and the like) to the physical environment (a patient's bones, physical instruments, and the like). In the illustrated embodiment, the reference feature or reference features may be one of the sets of a set of proximal guide pins 928 and/or a set of distal guide pins 930 deployed in one or more bones of the patient.

The present disclosure enables a surgeon to accurately position the navigation guide 900 which includes the marker(s) 920 and the marker(s) 920 enable a surgeon to accurately deploy the set of proximal guide pins 928 and/or set of distal guide pins 930 which can serve as reference features for a surgical procedure. In this manner, the marker 920 serves a similar role to a fiducial used in other surgical procedures or contexts. Consequently, the navigation guide 900 can serve as a useful tool for a surgeon to ensure that their actions in the physical environment will match those prepared and/or preplanned in a virtual environment or model environment. The reference features serve as valuable resources and/or references for one or more steps of a surgical procedure.

In addition, the navigation guide 900 can include a variety of features, structures, and/or aspects that can serve or facilitate accurately positioning the navigation guide 900 with respect to anatomy of a patient. In one embodiment, a navigation guide 900 includes a bone engagement surface 922 configured to register to an anatomical structure of one or more bones, the bone engagement surface defined based on medical imaging taken of the one or more bones. Alternatively, or in addition, the navigation guide 900 may include a registration key and/or one or more bone engagement openings.

The bone engagement surface 922 can be shaped to match a first surface of a first bone and a second surface of a second bone of a joint. In one embodiment, the bone engagement surface 922 may include a custom contoured surface of the inferior side 918 to match the shapes of one or more of the surfaces of one or more bones. In the illustrated embodiment, the bone engagement surface 922 may be configured to conform to the surface(s) of a medial cuneiform 202 and/or a first metatarsal 208.

In one embodiment, the bone engagement surface 922 may have a cuneiform apposition portion 932 shaped to lie against a surface (such as a dorsal surface) of the medial cuneiform 202, and a metatarsal apposition portion 934 shaped to lie against a surface (such as a dorsal surface) of the first metatarsal 208. As illustrated, the cuneiform apposition portion 932 may be contoured to match the contour of the dorsal surface of the cuneiform on which it is to rest, and the metatarsal apposition portion 934 may similarly be contoured to match the contour of the dorsal surface of the metatarsal on which it is to rest. Thus, the navigation guide 900 may have only one stable position and orientation relative to the cuneiform and the metatarsal. Alternatively, or in addition, the cuneiform apposition portion 932 may be contoured to match the contour of a surface that is between the dorsal surface and a medial or lateral surface and/or the surface includes at least a portion of the dorsal surface of the cuneiform on which it is to rest, and the metatarsal apposition portion 934 may similarly be contoured to match the contour of a surface that is between the dorsal surface and a medial or lateral surface and/or the surface includes at least a portion of the dorsal surface of the metatarsal.

In one example, the bone engagement surface 922 can be shaped such that the bone engagement surface 922 matches a surface of a cuneiform bone and a surface of a metatarsal bone of a tarsometatarsal ("TMT") joint. The bone engagement surface 922 can be so shaped because it is fabricated from a bone model of the patient's bones. The body 906 is configured, designed, and/or fabricated to seat transverse to a joint (e.g., a TMT joint) with the bone engagement surface 922 engaging a first surface of a first bone and a second surface of a second bone.

In one embodiment, the body 906 is configured to reside on the dorsal surfaces of the first cuneiform and the first metatarsal to provide proper alignment of the body 906 with the metatarsocuneiform joint (e.g., the joint between the first metatarsal and the medial cuneiform bone, aka a TMT joint). In another embodiment, the body 906 is configured to reside or sit between the medial surfaces and the dorsal surfaces, or on the medial surfaces of the first cuneiform and the first metatarsal to provide proper alignment of the body 906 with the metatarsocuneiform joint (e.g., the joint between the first metatarsal and the medial cuneiform bone) for an osteotomy.

In certain embodiments, the bone engagement surface 922 may include a cuneiform apposition portion 932 and a metatarsal apposition portion 934. As shown, the cuneiform apposition portion 932 may be contoured to match the contour of the surface of the first cuneiform on which it is to rest, and the metatarsal apposition portion 934 may similarly be contoured to match the contour of the surface of the first metatarsal on which it is to rest. Thus, the body 906 may have only one stable position and orientation relative to the first cuneiform and the first metatarsal during a surgical osteotomy for correcting the condition.

Advantageously, the fidelity of the patient imaging data enables the bone model, preliminary cutting guide model, and patient specific instrument (e.g., patient-specific cutting guide, patient specific pin guide, patient specific alignment guide, navigation guide, resection guides, etc.) to uniquely match a particular patient. Consequently, the bone engagement surface 922 can engage the surfaces of the bones of a joint in a single configuration. Such a close matching fit facilitates the surgical osteotomy.

FIG. 9C illustrates an inferior view towards the inferior side 918 of the navigation guide 900. In the illustrated embodiment, the navigation guide 900 includes a bone engagement opening 936 formed on the inferior side 918 of the body 906. The bone engagement opening 936 is an opening in a side of the body 906 configured to match a size, contour, and/or configuration of a bone. Advantageously, the length, width, and/or depth of the bone engagement opening 936 are configured to match the shape of the bone that fills the bone engagement opening 936 when the navigation guide 900 is deployed and used.

In the illustrated embodiment, the bone engagement opening 936 is on the inferior side 918 of the body 906. The bone engagement opening 936 is configured to receive at least a portion of a bone when the navigation guide 900 is deployed for use. In one embodiment, the bone engagement opening 936 is the opening near, or on, the inferior side 918 and may be bordered by a part of the inferior side 918 opposite the superior side 916, part of the inferior side 918 opposite the lateral side 914, and/or part of the inferior side 918 opposite the medial side 912. In certain embodiments, the medial side 912 and/or lateral side 914 may extend in an inferior direction as shown.

In certain embodiments, the bone engagement opening 936 includes the bone engagement surface 922. Where the bone engagement opening 936 includes the bone engagement surface 922 the matching of the bone engagement surface 922 to one or more surfaces of one or more bones can provide a further assurance to a surgeon that the navigation guide 900 is precisely positioned in a position desired. As illustrated in FIG. 9C, the bone engagement opening(s) 936, bone engagement surface 922, and/or a registration key can cooperate such that the navigation guide 900 fits like a puzzle piece onto and/or within anatomy of a patient. Consequently, a surgeon can have high assurance that the navigation guide 900 has been positioned in the location desired and/or designed and/or preplanned. In another embodiment, the bone engagement opening 936 may not include a bone engagement surface 922 and instead the bone engagement opening 936 may include a recess, cavity, depression, or the like and a smooth surface on an inferior side 918 of the body 906.

FIG. 9C illustrates that the bone engagement opening 936 may be in two parts bone engagement opening 936*a* and bone engagement opening 936*b*. Each respective bone engagement opening 936*a* and bone engagement opening 936*b* may be configured to receive a different bone. The bone engagement opening 936*a* may be configured to receive a cuneiform and the bone engagement opening 936*b* may be configured to receive a metatarsal.

In certain embodiments, a navigation guide 900 may include a registration key 938. The registration key 938 serves to further guide a surgeon to position the navigation guide 900 in a desired location with respect to anatomy of a patient. In certain embodiments, the registration key 938 may include one or more structures of the inferior side 918 that extend down into, or on, one or more of the adjacent joints and/or between the bones. The registration key 938 facilitates a desired alignment and placement of a navigation guide 900 on one or more joints and/or between bones. In one embodiment, the registration key 938 includes a protrusion that engages an opening between two bones of a joint. The registration key 938 may be on an inferior side 918 of the body 906. The registration key 938 can be formed by a variety of structures, including recesses, planar parts of an inferior side 918, angled parts of an inferior side 918, one or more projections added to an inferior side 918, openings in guide features, and the like.

Referring to FIGS. 9A and 9B, the navigation guide 900 includes a longitudinal axis 940 and a coupler 942 between the proximal end 902 and the distal end 904. The coupler 942 is configured to hold or keep the proximal end 902 and the distal end 904 together until a user operates the coupler 942 to separate the proximal end 902 and the distal end 904. Thus, the coupler 942 can temporarily hold the proximal end 902 and the distal end 904 and also release the proximal end 902 and the distal end 904 when needed. Those of skill in the art will appreciate that the coupler 942 can be implemented in a variety of ways using a variety of structures. In the illustrated embodiment, the coupler 942 implemented using a threaded shaft with a head and a driver and a set of holes in the body 906. At least one of the holes of the set of holes has internal threads configured to engage the external threads of the shaft.

As explained herein, the present disclosure enables fabrication of patient-specific instrumentation. FIGS. 9A-9C illustrate a patient-specific navigation guide 900 configured to guide a surgeon for an arthrodesis procedure on a tarsometatarsal ("TMT") joint of a patient. Specifically, the navigation guide 900 may be configured with a body 906 that spans a TMT joint between a metatarsal bone (e.g., a first metatarsal 208) and a cuneiform (e.g., a medial cuneiform 202). Accordingly, the inferior side 918 is configured to interface with the cuneiform bone and the metatarsal bone of the patient. In particular, the bone engagement surface 922 and/or bone engagement opening 936 are configured to interface with surfaces the cuneiform and metatarsal (e.g., a dorsal surface of each bone). In the illustrated embodiment, the reference feature is the set of proximal guide pins 928 deployed in the cuneiform and the set of distal guide pins 930 deployed in the metatarsal.

The reference feature can serve as a guide to a surgeon for a number of steps in a surgical procedure. In one embodiment, the reference feature includes a first reference feature and second reference feature. The first reference feature may include the set of proximal guide pins 928 deployed in a bone such as a cuneiform and the second reference feature may include the set of distal guide pins 930 deployed in a bone such as a metatarsal. Having two or more reference features can be advantageous because if a condition of a patient prevents deployment of one reference feature or the other, the second reference feature can serve as a backup. Furthermore, where a surgical procedure involves more than one bone, one reference feature can be established in a first bone and a second reference feature can be established in a second bone. Further, different stages of a surgical procedure may use one reference feature and not the other. Thus, having two reference features can facilitate certain stages of the surgical procedure.

Advantageously, providing two or more reference features can facilitate stages of a surgical procedure such as when bone fragments are to be aligned and/or reduced and/or when resections or osteotomies are to be performed on different bones of the patient. In one embodiment, a first reference feature may include a proximal alignment feature 944 and a second reference feature may include a distal alignment feature 946.

The proximal alignment feature 944 and the distal alignment feature 946 may be engaged in later steps of a surgical procedure by an instrument such as a positioning guide 880 to translate and/or rotate the one or more bones into a desired final position for reduction.

Typically, in an osteotomy for a condition such as a hallux valgus, it is desirable to rotate the first metatarsal 208 to address the condition. The first metatarsal 208 may be rotated for example to re-position distal plantar sesamoids from a lateral orientation to a more plantar orientation. Research has shown that performing such re-orientation mitigates recurrence of a hallux valgus condition. In such situations, the distal alignment feature 946 may serve as a reference and/or anchor for a positioning guide 880 that may cause the first metatarsal 208 to rotate and/or translate as the positioning guide 880 is deployed.

Similarly, the proximal alignment feature 944 may serve as a second anchor for the positioning guide 880. Before and after an osteotomy of a cuneiform or a metatarsal, the proximal alignment feature 944 and the distal alignment feature 946 may not be aligned with each other along a longitudinal axis of the first metatarsal 208. However, the positioning guide 880 may include distal and proximal holes that engage with the proximal alignment feature 944 and the distal alignment feature 946 such that sliding the positioning guide 880 towards the bones along proximal alignment feature 944 and the distal alignment feature 946 brings the bones and these two features into alignment with each other along the longitudinal axis of the first metatarsal 208.

Referring now to FIGS. 9A, 9B, and 9C, the illustrated embodiment includes two markers 920 that each are implemented using structures that serve multiple purposes. In addition, to identifying a location for reference features that may serve as alignment features, the markers 920 function as bone attachment features and reference features used with the bone attachment features may also serve as resection guide anchors.

In the illustrated embodiment, the navigation guide 900 includes a marker 920 that serves as a set of proximal bone attachment features 950 and a marker 920 that serves as a set of distal bone attachment features 952. The set of proximal bone attachment feature 950 and set of distal bone attachment feature 952 may include holes through the body 906 or guide pins that are deployed using those holes or a combination of both the holes and the guide pins deployed using those holes. The set of proximal bone attachment features 950 and/or set of distal bone attachment features 952 serve to hold the navigation guide 900 securely to the bone(s) as a set of proximal guide pins 928 and/or a set of distal guide pins 930 are deployed. Keeping the navigation guide 900 securely in place ensures that the guide pins are deployed where desired, particularly based on a preoperative plan.

Alternatively, or in addition, the set of proximal bone attachment feature 950 are configured to identify a location for a proximal reference feature (e.g., a set of proximal guide pins 928) and the set of distal bone attachment feature 952 are configured to identify a location for a distal reference feature (e.g., a set of distal guide pins 930). In certain embodiments, the proximal reference feature may be positioned and/or located on a cuneiform of a patient's foot and the distal reference feature may be positioned and/or located on a metatarsal of a patient's foot. The proximal reference feature may correspond to a proximal model reference (e.g., a set of model guide pins) on a cuneiform model of the cuneiform of the patient. The set of proximal bone attachment feature 950 are configured to receive the set of proximal guide pins 928 that serve as the proximal reference feature. The distal reference feature may correspond to a distal model reference (e.g., a set of model guide pins) on a metatarsal model of the metatarsal of the patient. The set of distal bone attachment feature 952 are configured to receive the set of distal guide pins 930 that serve as the distal reference feature.

As discussed above, reference features may be used for multiple purposes during a surgical procedure. Using reference features for multiple purposes can be advantageous because the bones of a patient (particularly in a foot or hand) are small and surgical procedures are more successful the fewer number of guide pins are used and the smaller the guide pins are. Using reference features such as guide pins for multiple purposes can reduce the number of guide pins used and/or reduce the number of holes formed in bones of the patient. These advantages can improve patient care and successful outcomes.

In the illustrated embodiment, a proximal/first reference feature (e.g., a set of proximal guide pins 928) and a distal/second reference feature (e.g., a set of distal guide pins 930) can be used as alignment features for a positioning guide and can also serve as anchors for other instruments during a surgical procedure. In the illustrated embodiment, the proximal/first reference feature serves as a proximal alignment feature 944 and as a proximal resection guide anchor 954 and the distal/second reference feature serves as a distal alignment feature 946 and as a distal resection guide anchor 956.

A guide anchor is an anchor for a resection guide (described herein). The guide anchor serves to hold a resection guide in place during an osteotomy. In one embodiment, a guide anchor is strategically placed guide pins that pass through a resection guide and hold the resection guide securely to a bone of a patient for the osteotomy. A proximal resection guide anchor 954 is a guide anchor that is proximal during a surgical procedure. A distal resection guide anchor 956 is a guide anchor that is distal during a surgical procedure. In certain embodiments, a proximal resection guide anchor 954 may be deployed in a cuneiform and a distal resection guide anchor 956 may be deployed in a metatarsal. Advantageously, because the surgical procedure is preplanned using medical imaging of bones of a patient the same guide pins that serve as a proximal reference feature and those that serve as a distal reference feature can also serve as a proximal resection guide anchor 954 and a proximal alignment feature 944 and as a distal resection guide anchor 956 and a distal alignment feature 946. Those of skill in the art will appreciate that a reference feature can serve as an alignment feature or a resection guide anchor or both depending on the embodiment. Advantageously, the navigation guide 900 may identify where to position the first reference feature and the second reference feature for use for resection or cutting of one or more bones and for alignment and repositioning of bone fragments after the osteotomies.

Referring to FIG. 9C, the navigation guide 900 can include a registration key 938 on the inferior side 918 of the body 906. In the illustrated embodiment, the registration key 938 includes a protrusion that engages an opening between a cuneiform and a metatarsal of a tarsometatarsal ("TM") joint. FIG. 9C illustrates that the navigation guide 900 can include a bone engagement surface 922 configured to register to an anatomical structure of at least one of the cuneiform, the metatarsal, and the TMT joint, the bone engagement surface 922 is defined based on medical imaging taken of the metatarsal and the cuneiform of the patient's foot.

FIGS. 9A, 9B, 9C illustrate that the set of proximal holes 924 and set of distal holes 926 are not aligned when measured along a length of the longitudinal axis 940. As discussed, this positioning is intentional because while the holes are not aligned initially, the implementation of the procedure will prepare the bones such that as the procedure completes guide pins deployed in the holes will be aligned with each other along a length of the longitudinal axis 940. Accordingly, the set of proximal holes 924 and/or set of distal holes 926 are not aligned with respect to a longitudinal axis of one of the bones of a patient.

Figure 9D:
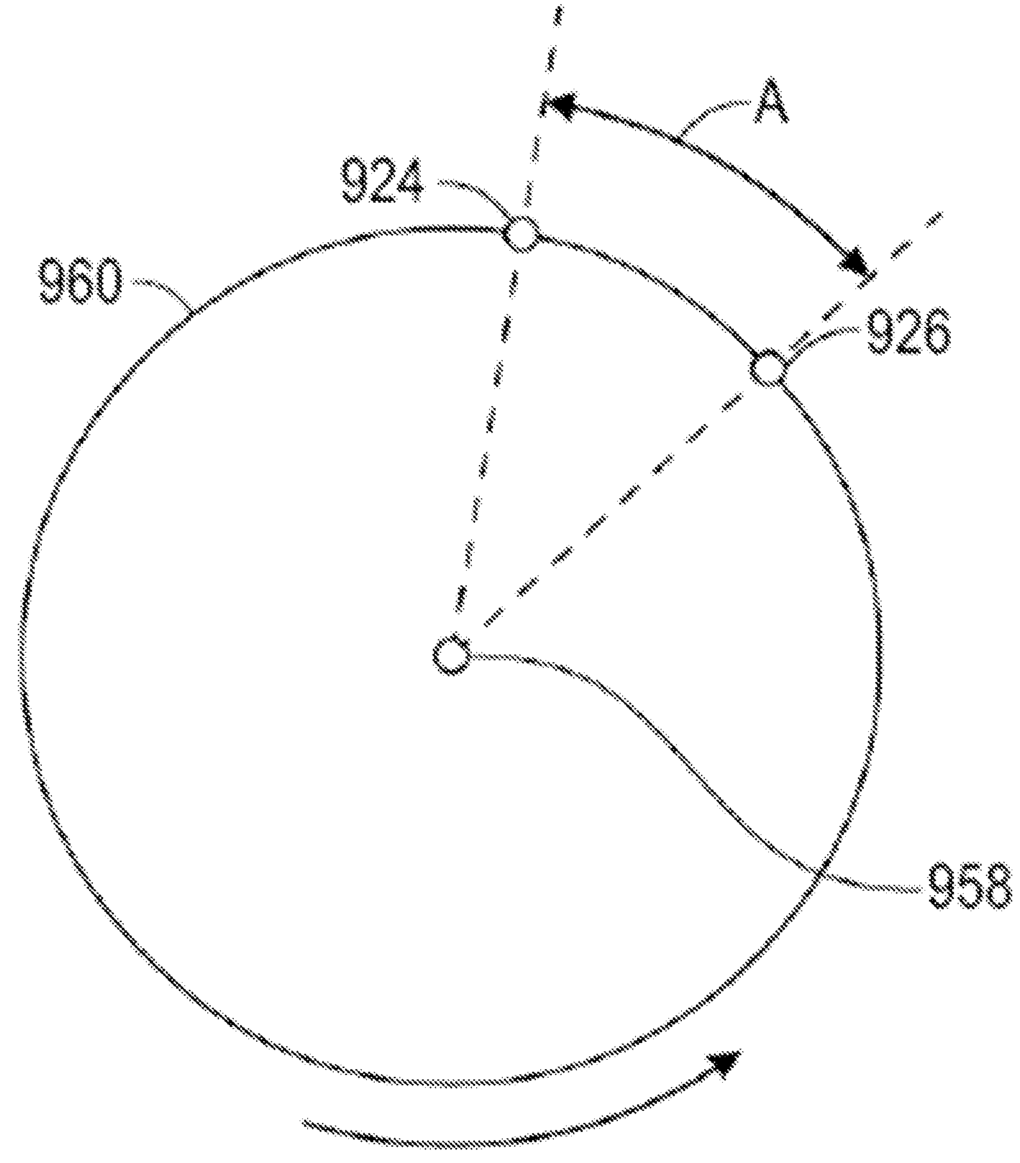
FIG. 9D illustrates a diagram representative of a cross-sectional view of cuneiform and a first metatarsal from a cuneiform looking towards a distal head of the metatarsal

FIG. 9D illustrates a diagram representative of a cross-sectional view of cuneiform and a first metatarsal from a cuneiform looking towards a distal head of the metatarsal. FIG. 9D further illustrates the offset relationship between the set of proximal holes 924 and the set of distal holes 926. FIG. 9D illustrates an axis 958 that corresponds to a long axis of a long bone such as a metatarsal. The circle 960 represents an approximate perimeter viewed along the axis 958.

FIGS. 9A-9C illustrate the relationship between the set of proximal holes 924 and the set of distal holes 926. Specifically, the proximal set of holes is spaced from the distal set of holes longitudinally along a long axis of the bone (e.g., metatarsal). FIG. 9D illustrates that the proximal set of holes (e.g., set of proximal holes 924) is offset about the long axis 958 by an angle alpha A from the distal set of holes (e.g., set of distal holes 926). Angle A represents the number of degrees of offset between the set of proximal holes 924 and the set of distal holes 926 measured about circle 960. In certain embodiments, angle A may range between about 3 and about 100 degrees. It should be noted that in certain embodiments, Angle A can also represent a number of degrees between the first position for a metatarsal prior to an osteotomy and the surgical procedure and a second position that the bone will be rotated to about the longitudinal axis 958 to reduce and complete the surgical procedure.

Figure 10A:
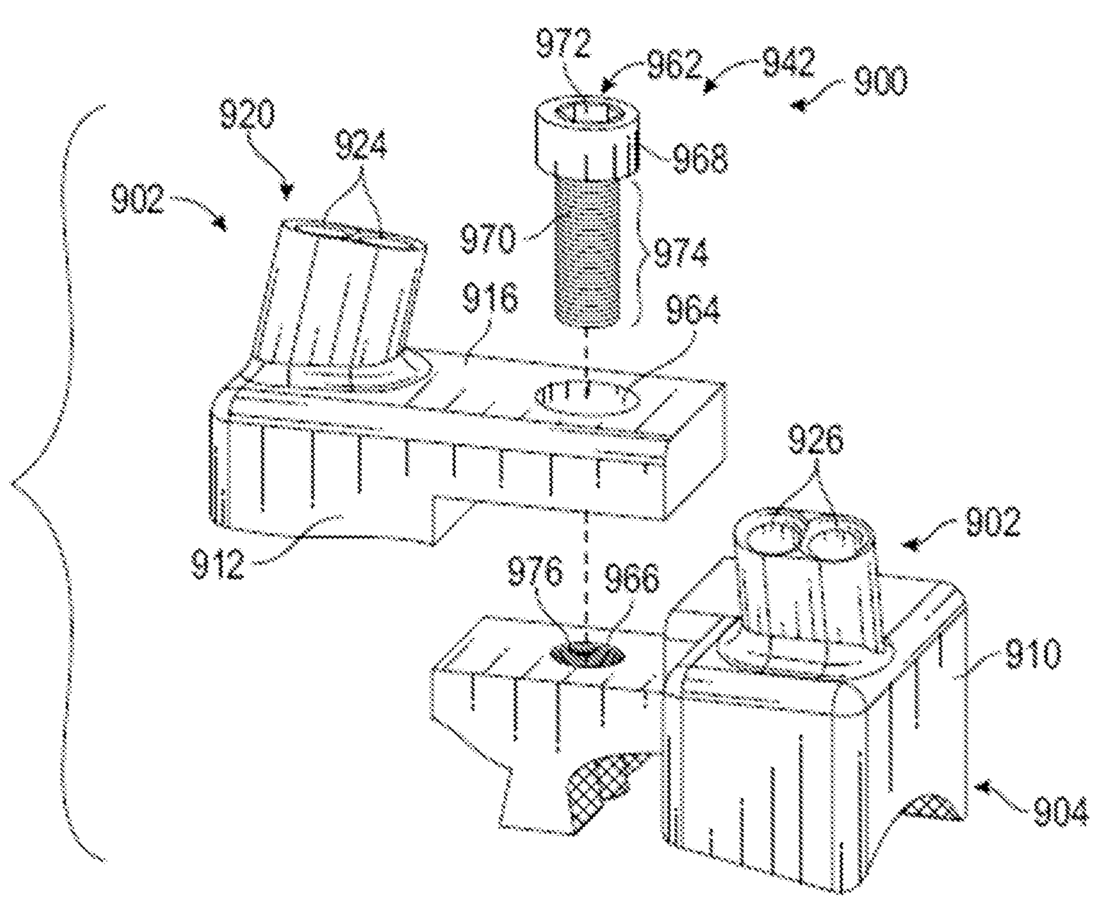
FIG. 10A illustrates an exploded view of a navigation guide according to one embodiment.

FIG. 10A illustrates an exploded view of a navigation guide 900 according to one embodiment. In the illustrated embodiment, the navigation guide 900 includes a coupler 942. Those of skill in the art will appreciate that a variety of structures and/or techniques may be used to implement or realize a coupler with the scope of the present disclosure. FIG. 10A illustrates just one example.

In the illustrated embodiment, the coupler 942 includes a bolt 962, a head opening 964 in one of the proximal end 902 and the distal end 904, and a shaft opening 966 in the other one of the proximal end 902 and the distal end 904. In the illustrated embodiment, the head opening 964 is in the proximal end 902 and the shaft opening 966 is in the distal end 904.

The bolt 962 may include a head 968 and a shaft 970. The head 968 may include a drive feature 972. The shaft 970 may include a set of threads 974 on an external surface of the shaft 970.

The head opening 964 is configured to contact and/or accept at least part of a head 968 of the bolt 962. The shaft opening 966 is configured to accept at least part of a shaft 970 of the bolt 962. In one embodiment, the shaft opening 966 includes internal threads 976 configured to engage the set of threads 974 on the external surface of the shaft 970.

In one embodiment, the coupler 942 may be deployed by a fabricator of the coupler 942. Thus, initially the proximal end 902 and the distal end 904 may be joined by the coupler 942 and the navigation guide 900 ready for use by a user or surgeon. Advantageously, the coupler 942 is configured to be operated to separate the proximal end 902 from the distal end 904. In the illustrated embodiment, this may be accomplished by engaging the drive feature 972 and rotating the shaft 970 in a direction opposite a direction in which the threads have been engaged with each other. Once the shaft 970 is backed out of the shaft opening 966, the proximal end 902 and/or distal end 904 can be separated. If the proximal end 902 and/or distal end 904 are separated after deployment of the set of proximal guide pins 928 and the set of distal guide pins 930, separation of the proximal end 902 and/or distal end 904 can permit removal of the proximal end 902 and/or distal end 904 without removing the set of proximal guide pins 928 and/or the set of distal guide pins 930. Of course, those of skill in the art will appreciate that rather than use a coupler 942, the navigation guide 900 may be removed by removing one or the other or both of the set of proximal guide pins 928 and/or the set of distal guide pins 930.

Figure 10B:
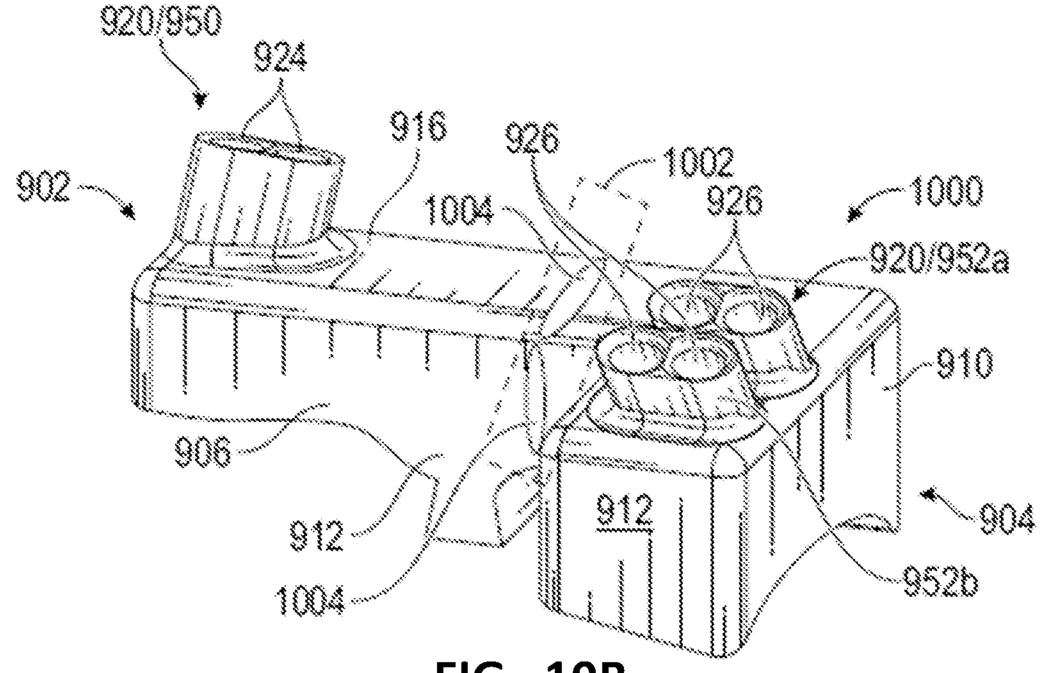
FIG. 10B illustrates a top perspective view from a medial side of a navigation guide according to one embodiment.

FIG. 10B illustrates a top perspective view from a medial side of a navigation guide 1000 according to one embodiment. The navigation guide 1000 may have many structures, features, and functions, operations, and configuration similar or identical to those of the navigation guide 900 described herein, like parts are identified with the same reference numerals. The Accordingly, the navigation guide 1000 may include a body 906, a markers 920, set of proximal holes 924, and set of distal holes 926. Etc.

The navigation guide 1000 may differ from the navigation guide 900 because the navigation guide 1000 may not include a specific coupler 942. Instead, the navigation guide 1000 may include another feature that enables the separation of guide pins in the set of proximal holes 924 and/or the set of distal holes 926 from each other. In the illustrated embodiment, this feature is a frangible section 1002 between the proximal end 902 and the distal end 904. The frangible section 1002 may be configured to separate the proximal end 902 from the distal end 904 by dividing the body 906 in response to a force delivered by a user to the frangible section 1002. Alternatively, or in addition, the frangible section 1002 may separate one or the other of the set of proximal holes 924 or the set of distal holes 926 from the body 906 in response to a force delivered by a user to the frangible section 1002.

Those of skill in the art will appreciate that a variety of techniques and/or technologies may be used to implement the frangible section 1002. For example, the body 906 in the frangible section 1002 may be made of a material that can readily broken and/or that is biocompatible for use in a body of a patient. Examples of such materials include, but are not limited to, Polylactic Acid (PLA), Polyglycolic Acid (PGA), Poly(lactic-co-glycolic acid) (PLGA), Magnesium Alloys, Bioabsorbable Metals, Biocompatible Ceramics, and the like.

Alternatively, or in addition, in the illustrated embodiment, the frangible section 1002 may also include structures that facilitate breaking apart the navigation guide 1000 when needed. For example, the frangible section 1002 may include openings 1004 (of a shape such as oval) that can facilitate breaking about the frangible section 1002.

FIG. 10B illustrates one example of a navigation guide 1000 that may not include an explicit coupler, but instead includes another aspect or feature that enables separation of the proximal end 902 and the distal end 904. The force required to break up the frangible section 1002 can be of a variety of different types such as a strike force, a prying force, a torque, cutting, drilling, or the like. Further, a variety of different instruments may be used to break the frangible section 1002 such as a cutting tool, a mallet, a clamp, a probe, an osteotome, a bone rongeur, or the like. In one embodiment, the breaking of the frangible section 1002 separates the proximal end 902 from the distal end 904 or the set of proximal holes 924 from the set of distal holes 926 in a manner that does not leave any shards or parts of the frangible section 1002 behind in the patient. Alternatively, or in addition, the frangible section 1002 is made of a material that can biodegrade safely in the patient if left behind. Of course, certain shards may be removed as part of the surgical procedure.

The navigation guide 1000 illustrates another difference from the embodiment of the navigation guide 900. The navigation guide 1000 includes a plurality of bone attachment features. The plurality of bone attachment features may be implemented on a proximal end 902 and/or a distal end 904. In the illustrated embodiment, the plurality of bone attachment features are implemented in a plurality of sets of distal bone attachment features 952*a,b*. The plurality of sets of bone attachment features are each configured to receive a set of distal guide pins 930. The plurality of sets of bone attachment features enable a surgeon to decide intraoperatively which bone attachment features to deploy guide pins into. Alternatively, or in addition, a surgeon may choose to deploy guide pins into multiple bone attachment features of the plurality of sets of bone attachment features.

As illustrated in FIG. 10B, each set of distal bone attachment features 952*a,b* are positioned radially about a plane perpendicular to a long axis 940 of the metatarsal at a different angle relative to the set of proximal bone attachment features 950. These different angles may be predetermined to provide different amounts of rotation of a metatarsal in a subsequent step of the surgical procedure. In certain embodiments, the different angles may differ by about 5 degrees relative to each other.

Figures 11A, 11B, 11C, 11D:
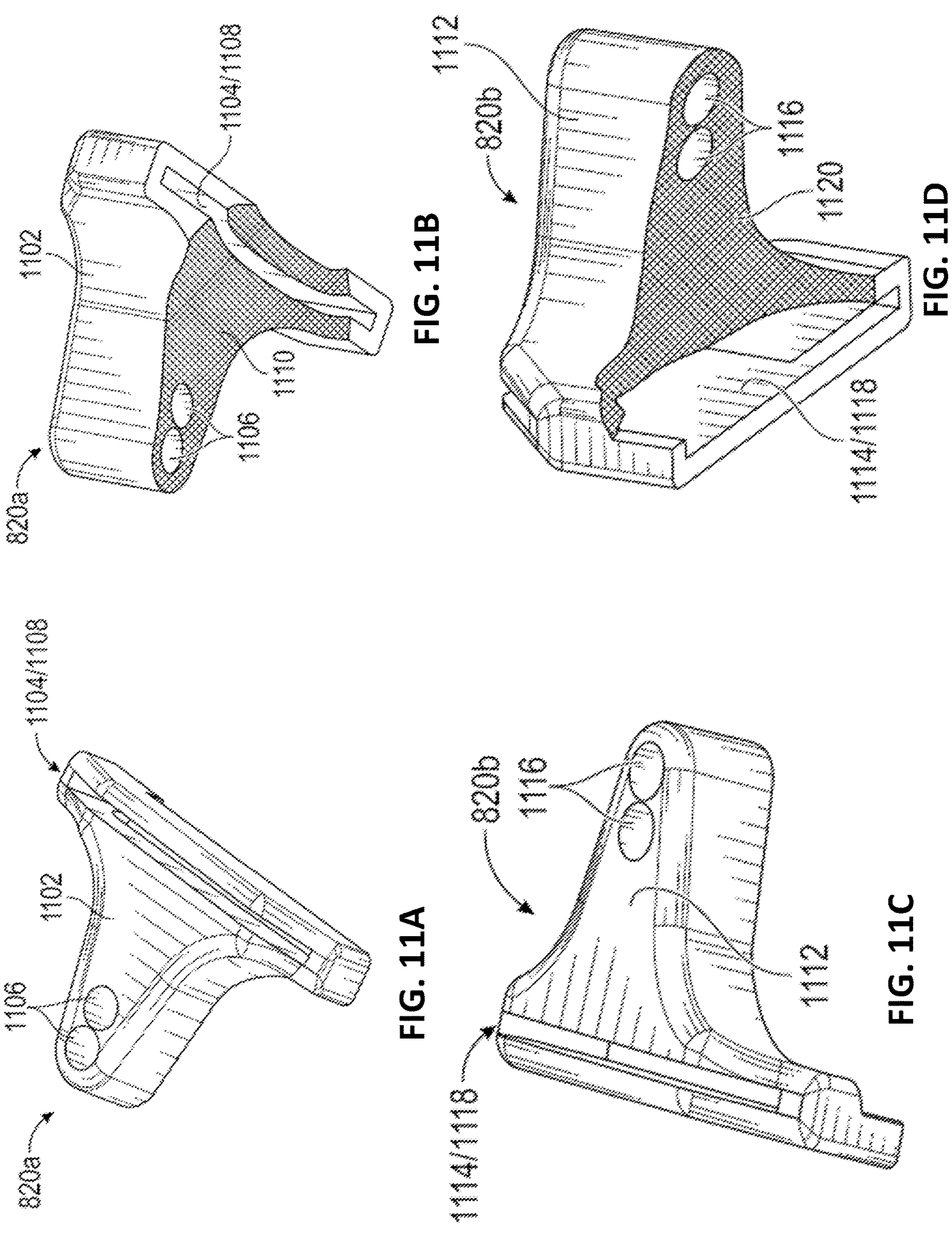
FIG. 11A illustrates a top perspective view of a proximal resection guide according to one embodiment.
FIG. 11B illustrates a bottom perspective view of a proximal resection guide according to one embodiment.
FIG. 11C illustrates a top perspective view of a distal resection guide according to one embodiment.
FIG. 11D illustrates a bottom perspective view of a distal resection guide according to one embodiment.

FIG. 11A illustrates a top perspective view of a proximal resection guide 820*a* according to one embodiment. In one embodiment, the proximal resection guide 820*a* is configured to address the deformity. The proximal resection guide 820*a* can be configured to engage the set of proximal guide pins 928 (e.g., K-wires) positioned using the navigation guide 900.

The proximal resection guide 820*a* includes a body 1102, a resection feature 1104, and one or more openings 1106. The resection feature 1104 guides resection of tissue such as a bone. In particular, the resection feature 1104 can guide a surgeon in performing an osteotomy. Advantageously, the position, size, depth, and angle of the resection feature 1104 relative to the a long axis of the tissue such as a bone can be preplanned, predetermined, such that forming a cut face using the resection feature 1104 will enable implementation of a correction that addresses a condition of a patient. Such planning and precision is possible because the proximal resection guide 820*a* can be designed based on medical imaging of the patient's anatomy.

In the illustrated embodiment, the proximal resection guide 820*a* may be patient-specific and specifically designed for use in doing an osteotomy on a cuneiform of a patient. Consequently, the resection feature 1104 may be referred to as a cuneiform resection feature 1104. In one embodiment, the cuneiform resection feature 1104 may be configured to guide resection of the cuneiform to form a cut face of the cuneiform for a correction of a condition present in a patient's foot.

The cuneiform resection feature 1104 may be specifically designed for one particular patient. Alternatively, or in addition, the cuneiform resection feature 1104 may be designed for use with all patients and may enable a predefined osteotomy such as forming a cut face perpendicular to a long axis of a bone being cut. In such an embodiment, another resection feature (e.g., distal resection guide 820*b*) may be angled in order to implement a desired correction.

The one or more openings 1106 are positioned and/or angled through the body 1102 to slide over, engage, or accept guide pins. In particular, the one or more openings 1106 may be configured to engage with the set of proximal guide pins 928. In certain embodiments, the set of proximal guide pins 928 may be positioned prior to deploying the proximal resection guide 820*a* and the one or more openings 1106 may engage a set of proximal guide pins 928 already secured to a bone, such as a cuneiform.

FIG. 11B illustrates a bottom perspective view of a proximal resection guide 820*a* according to one embodiment. Advantageously, in certain embodiments, the proximal resection guide 820*a* can also include a bone engagement surface 1110. FIG. 11B illustrates one example of a bone engagement surface 1110. The bone engagement surface 1110 can facilitate proper positioning/registering of the proximal resection guide 820*a* to a desired location on one or more bones and/or transverse to a joint, such as a TMT. The bone engagement surface 1110 may cooperate with the guide pins (e.g., set of proximal guide pins 928) to ensure secure positioning of the proximal resection guide 820*a*. Advantageously, the fidelity of the medical imaging and modeled surface of the bone as well as the fidelity of the bone engagement surface 1110 enable the surgeon to accurately position the proximal resection guide 820*a*.

FIG. 11C illustrates a top perspective view of a distal resection guide 820*b* according to one embodiment. In one embodiment, the distal resection guide 820*b* is configured to address the deformity. The distal resection guide 820*b* can be configured to engage the set of distal guide pins 930 (e.g., K-wires) positioned using the navigation guide 900 or another guide or manually.

The distal resection guide 820*b* includes a body 1112, a resection feature 1114, and one or more openings 1116. The resection feature 1114 guides resection of tissue such as a bone. In particular, the resection feature 1114 can guide a surgeon in performing an osteotomy. Advantageously, the position, size, depth, and angle of the resection feature 1114 relative to the a long axis of the tissue such as a bone can be preplanned, predetermined, such that forming a cut face using the resection feature 1114 will enable implementation of a correction that addresses a condition of a patient. Such planning and precision is possible because the distal resection guide 820*b* can be designed based on medical imaging of the patient's anatomy.

In the illustrated embodiment, the distal resection guide 820*b* may be patient-specific and specifically designed for use in doing an osteotomy on a metatarsal of a patient, such as a proximal end of a metatarsal. Consequently, the resection feature 1114 may be referred to as a metatarsal resection feature 1118. In one embodiment, the metatarsal resection feature 1118 may be configured to guide resection of the metatarsal to form a cut face of the metatarsal for a correction of a condition present in a patient's foot.

The metatarsal resection feature 1118 may be specifically designed for one particular patient. Alternatively, or in addition, the metatarsal resection feature 1118 may be designed for use with all patients and may enable a predefined osteotomy such as forming a cut face perpendicular to a long axis of a bone being cut. In such an embodiment, another resection feature (e.g., proximal resection guide 820*a*) may be angled in order to implement a desired correction.

A resection feature can take a variety of forms. Often the resection feature includes one or more openings that are sized to receive a cutting tool and provide clearance and/or allowance for the cutting tool to cut tissue of the patient.

The one or more openings 1116 are positioned and/or angled through the body 1112 to slide over, engage, or accept guide pins. In particular, the one or more openings 1116 may be configured to engage with the set of distal guide pins 930. In certain embodiments, the set of distal guide pins 930 may be positioned prior to deploying the distal resection guide 820*b* and the one or more openings 1116 may engage a set of distal guide pins 930 already secured to a bone, such as a metatarsal.

FIG. 11D illustrates a bottom perspective view of a distal resection guide 820*b* according to one embodiment. Advantageously, in certain embodiments, the distal resection guide 820*b* can also include a bone engagement surface 1120. FIG. 11B illustrates one example of a bone engagement surface 1120. The bone engagement surface 1120 can facilitate proper positioning/registering of the distal resection guide 820*b* to a desired location on one or more bones and/or transverse to a joint, such as a TMT. The bone engagement surface 1120 may cooperate with the guide pins (e.g., set of distal guide pins 930) to ensure secure positioning of the distal resection guide 820*b*. Advantageously, the fidelity of the medical imaging and modeled surface of the bone as well as the fidelity of the bone engagement surface 1120 enable the surgeon to accurately position the distal resection guide 820*b*.

Referring to FIGS. 11A-11D, embodiments of the present disclosure may use one or the other or both of the proximal resection guide 820*a* and the distal resection guide 820*b* for a surgical procedure. In certain embodiments, using two separate resection guides 820 may be advantageous because use of separate resection guides 820 provide for space/clearance within an opening in the skin of the patient for placement and use of each separate guide 820. For example, each guide 820 may be used in sequence separately one after the other with the first removed while the second is in use. This can provide more room for performing each osteotomy on two adjacent bones.

Those of skill in the art will appreciate that the resection guides 820 of the present disclosure can be designed and/or fabricated with a variety of features and/or aspects. For example, in one embodiment, the one or more openings 1106 and/or one or more openings 1116 may extend through the body 1102 and/or body 1112 at a right angle to a surface of the body 1102 and/or body 1112. Alternatively, or in addition, the resection feature 1104 and/or resection feature 1114 may extend through the body 1102 and/or body 1112 at a right angle to a surface of the body 1102 and/or body 1112. Or, one of the proximal resection guide 820*a* and the distal resection guide 820*b* may include openings perpendicular to a surface of the body and the other may have openings that are angled at a non-perpendicular angle relative to the surface of the body. Or, one of the proximal resection guide 820*a* and the distal resection guide 820*b* may include a resection feature perpendicular to a surface of the body and the other may have a resection feature that is angled at a non-perpendicular angle relative to the surface of the body. Those of skill in the art will appreciate that any permutation of angled orientations between the openings and the a resection features of the proximal resection guide 820*a* and/or the distal resection guide 820*b* can be used since these guides are fabricated to satisfy a preoperative plan for a correction for the patient.

The resection guide provides an accurate and precise guide for performing one or more osteotomies on a bone of a patient. In particular, the resection guide is specifically designed and engineered for one or more osteotomies at or near an end of a metatarsal bone and/or a cuneiform bone of the patient. Advantageously, the variability and flexibility provided for the design of the resection guide enable an innumerable set of resection guides that can be fabricated.

In particular, a unique resection guide can be designed, developed and fabricated for each patient (e.g. patient-specific). The ability of a surgeon and/or technician to predetermine where, and how to orient the resection feature(s) provides for an infinite number of different combinations for making a variety of different osteotomies in a bone. Consequently, a surgeon can predetermine an angle to the osteotomy to define or set to achieve a desired type and/or amount of correction for a bone. Furthermore, the surgeon can make this predetermination based on medical imaging taken of the patient's foot such that the resection guide is unique to a particular patient. In one embodiment, a surgeon may specify aspects of the resection guide in a prescription for the design and/or fabrication of the resection guide. Depending on the nature of the correction to be performed a surgeon and/or a technician may define a resection guide to produce one of a uniplanar correction, a biplanar correction, and a triplane correction.

In another embodiment, the resection guide is designed to approach and engage a metatarsal from the medial side of the bone. Furthermore, a surgeon can define a length and width for the bone engagement surface 1110, 1120. Advantageously, a surgeon can define, alter, or adjust the bone engagement surface 1110, 1120 to suit their preferences, the needs of the patient, or the like. By adjusting the bone engagement surface 1110, 1120, a surgeon can impact how the resection guide 820*a,b* seats on the bones during the surgical procedure. In one embodiment, a surgeon may want a loose fit while another surgeon may want a tighter fit. Alternatively, or in addition, a surgeon can choose to position the resection guide 820 at another position on a particular surface of a bone. Those of skill in the art will appreciate that changing the position of the resection guide 820 can change the makeup and configuration of bone engagement surface 848 because the surface contacting the resection guide 820 will change. In one embodiment, the surgeon may alter predefined configurations or choose a configuration from a set of optional configurations. Alternatively, or in addition, a surgeon may define a resection guide 820 from scratch.

One challenge in performing osteotomies on such small bones as those of a hand or foot, is how to make accurate and precise cuts on such small bones/structures. Embodiments such as the resection guide 820*a,b*, can be used to help address this challenge. For example, the resection guide 820*a,b* may include a landmark registration feature that facilitates positioning the resection guide in a predetermined position on a bone.

FIG. 12A illustrates a top perspective view of a positioning guide 1200 from a medial side according to one embodiment. The positioning guide 1200 may be similar to or the same as the positioning guide 880. The positioning guide 1200 serves to position one or more bones in relation to another anatomical structure. For example, the positioning guide 1200 may position a metatarsal and/or a cuneiform relative to each other, in particular following an osteotomy to each these bones. Advantageously, a positioning guide 1200 can facilitate placing both bones into a precise relationship relative to each other that matches or sufficiently satisfies the arrangement predetermined in a preoperative plan. Used as designed, a positioning guide 1200 can provide a surgeon with assurance that the repositioning and/or reduction of the bones as planned is being implemented.

A positioning guide 1200 can include a positioning guide body 1202 having a proximal end 1204, a distal end 1206, a superior side 1208, an inferior side 1210, a medial side 1212, a lateral side 1214, a proximal side 1216, and a distal side 1218. In one embodiment, the positioning guide 1200 may also include a set of proximal holes 1220, a set of distal holes 1222, a bone engagement surface 1224, and/or a registration key 1226 (or landmark registration feature).

The set of proximal holes 1220 may extend from the superior side 1208 to the inferior side 1210. The set of proximal holes 1220 are configured to accept and/or slide over a proximal alignment feature 944. The set of distal holes 1222 may extend from the superior side 1208 to the inferior side 1210. The set of distal holes 1222 are configured to accept and/or slide over a distal alignment feature 946. Advantageously, in one embodiment, a surgeon may use the positioning guide 1200 after performing an osteotomy on two bones of a TMT joint. The set of proximal holes 1220 and the set of distal holes 1222 are positioned in the positioning guide body 1202 and relative to each other such that as the positioning guide 1200 slides along the proximal alignment feature 944 and distal alignment feature 946 towards the bones (e.g., a cuneiform and a metatarsal) one or both of these bones move (translate and/or rotate) in a way that closes an osteotomy that has been performed on one of the bones. In certain embodiments, deploying the positioning guide 1200 on the proximal alignment feature 944 and the distal alignment feature 946 closes an osteotomy on a cuneiform and a metatarsal of a TMT joint. In this manner, the positioning guide 1200 facilitates translating and/or rotating the bones for a reduction and in preparation for permanent fixation.

Alternatively, or in addition, the set of proximal holes 1220 and the set of distal holes 1222 are positioned in the positioning guide body 1202 and relative to each other such that bone fragments connected to the proximal alignment feature 944 and distal alignment feature 946 are not only brought into contact with each other, they are also compressed against each other. In one embodiment, moving the positioning guide 1200 along the proximal alignment feature 944 and distal alignment feature 946 towards the metatarsal and the cuneiform compresses a cut face of the metatarsal against a cut face of the cuneiform. For example, to provide sufficient compression for a successful union of the two bones through the healing process.

FIG. 12B illustrates a bottom perspective view of a positioning guide 1200 according to one embodiment. FIG. 12B illustrates the bone engagement surface 1224 of the positioning guide 1200. In certain embodiments, the bone engagement surface 1224 is designed and/or fabricated in a similar manner to the other bone engagement surfaces described herein (e.g., bone engagement surface 922, bone engagement surface 1110, bone engagement surface 1120). Those of skill in the art will appreciate that any of the components of the systems (e.g., system 400, system 500, system 800) of the present disclosure may include a bone engagement surface while one or more other components may not. In one embodiment, at least one of a navigation guide 900, a proximal resection guide 820*a*, a resection guide 820*b*, and a positioning guide 1200 (e.g., positioning guide 880) comprises a bone engagement surface configured to register to an anatomical structure of a patient's foot.

In the illustrated embodiment, the positioning guide 1200 is configured to span an osteotomy of a TMT and includes a bone engagement surface 1224 that engages a surface of a cuneiform and a bone engagement surface 1224 that engages a surface of a metatarsal. These may be two separate bone engagement surfaces or a single bone engagement surface 1224 that extends to both bones.

Advantageously, the bone engagement surface 1224 is configured to match the surface of the two bones when reduced and prepared for permanent fixation. Those of skill in the art will appreciate that the composition of the bone engagement surface 1224 after one or more osteotomies can be very different and unique from a composition of the surface of both bones prior to an osteotomy and/or prior to translation or rotation of the bones into a final position for fixation. Because the bone engagement surface 1224 can match the surfaces of the two bones in a corrected relationship, a surgeon can be assured that the bones are where desired when the bone engagement surface 1224 engages a surface of both bones in the reduced condition.

Furthermore, the registration key 1226 is fabricated to match any protrusions and/or recesses that are formed by the osteotomy (ies) and the repositioning of the bones. Thus, the seating and/or registration of the registration key 1226 to the bone(s) can confirm and/or assure a surgeon that the bones are where desired and the surgical procedure is prepared for a fixation stage.

FIG. 12C illustrates a perspective view of a positioning guide 1200 from a lateral side according to one embodiment.

Figure 13:
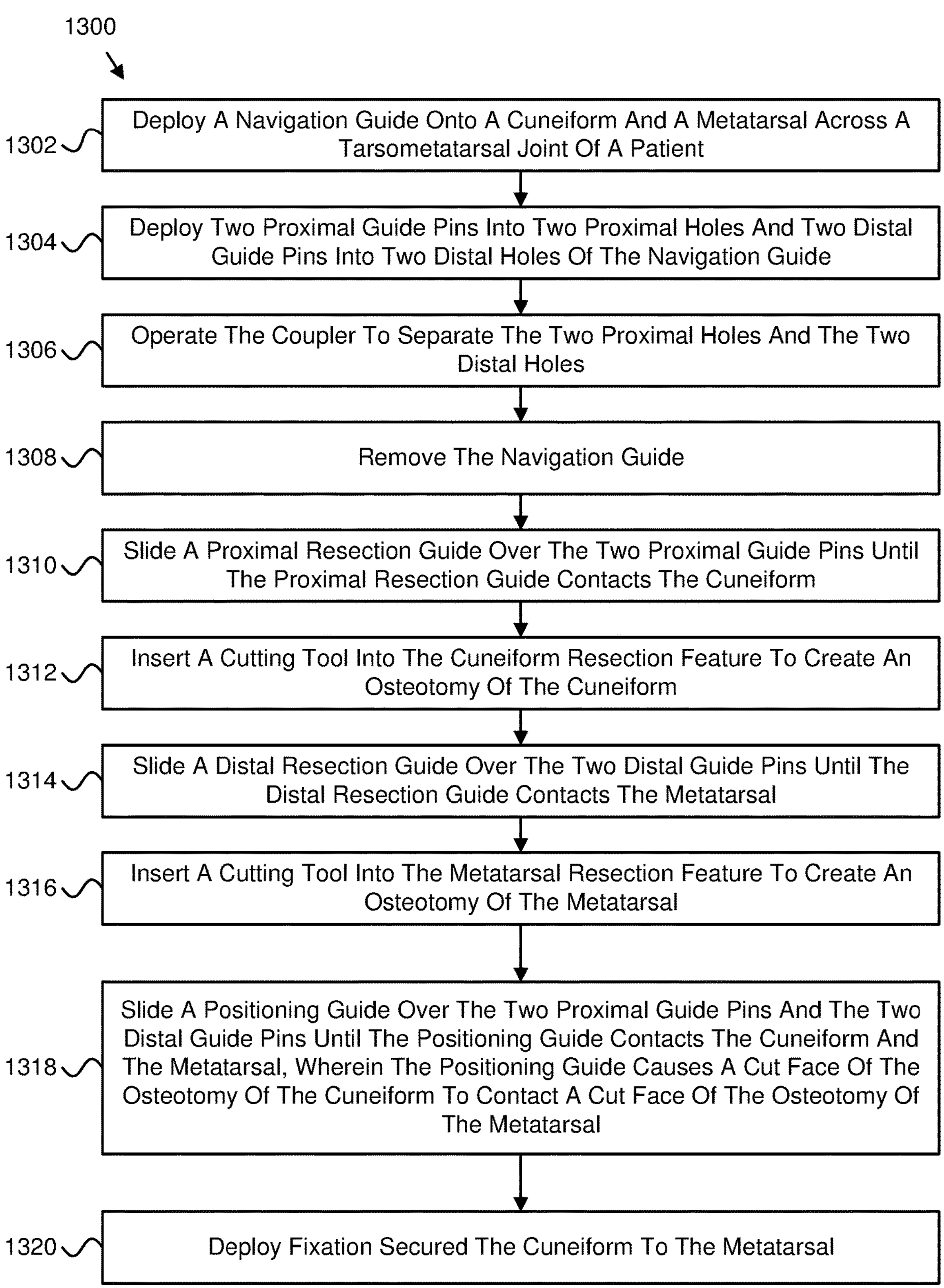
FIG. 13 is a flowchart diagram depicting a method for remediating a condition, according to one embodiment.

FIG. 13 is a flowchart diagram depicting a method for remediating a condition, according to one embodiment. FIG. 13 is a flowchart of an example method 1300. In some implementations, one or more method steps of FIG. 13 may be performed by a surgeon using one or more of the components described herein. As shown in FIG. 13, method 1300 may include deploying a navigation guide onto a cuneiform and a metatarsal across a tarsometatarsal (TMT) joint of a patient, the navigation guide including: two proximal holes configured to accept and identify a location for two proximal guide pins that provide a proximal reference feature on the cuneiform for a proximal model reference on a cuneiform model of the cuneiform; two distal holes configured to accept and identify a location for two distal guide pins that provide a distal reference feature on the metatarsal for a distal model reference on a metatarsal model of the metatarsal; a coupler configured to connect the two proximal holes and the two distal holes across the TMT until an user operates the coupler to separate the two proximal holes and the two distal holes (block 1302). For example, a surgeon may deploy a navigation guide onto a cuneiform and a metatarsal across a tarsometatarsal ("TMT") joint of a patient, the navigation guide including: two proximal holes configured to accept and identify a location for two proximal guide pins that provide a proximal reference feature on the cuneiform for a proximal model reference on a cuneiform model of the cuneiform; two distal holes configured to accept and identify a location for two distal guide pins that provide a distal reference feature on the metatarsal for a distal model reference on a metatarsal model of the metatarsal; a coupler configured to connect the two proximal holes and the two distal holes across the TMT joint until an user operates the coupler to separate the two proximal holes and the two distal holes, as described above.

As also shown in FIG. 13, method 1300 may include deploying the two proximal guide pins into the two proximal holes and the two distal guide pins into the two distal holes (block 1304). For example, a surgeon may deploy the two proximal guide pins into the two proximal holes and the two distal guide pins into the two distal holes, as described above.

As further shown in FIG. 13, method 1300 may include operating the coupler to separate the two proximal holes and the two distal holes (block 1306). For example, a surgeon may operate the coupler to separate the two proximal holes and the two distal holes, as described above.

As also shown in FIG. 13, method 1300 may include removing the navigation guide (block 1308). For example, a surgeon may remove the navigation guide once proximal guide pins are separated from distal guide pins, as described above.

As further shown in FIG. 13, method 1300 may include sliding a proximal resection guide over the two proximal guide pins until the proximal resection guide contacts the cuneiform, the proximal resection guide having a cuneiform resection feature configure to guide resection of the cuneiform (block 1310). For example, a surgeon may slide a proximal resection guide over the two proximal guide pins until the proximal resection guide contacts the cuneiform, the proximal resection guide having a cuneiform resection feature configure to guide resection of the cuneiform, as described above.

As also shown in FIG. 13, method 1300 may include inserting a cutting tool into the cuneiform resection feature to create an osteotomy of the cuneiform (block 1312). For example, a surgeon may insert a cutting tool into the cuneiform resection feature to create an osteotomy of the cuneiform, as described above.

As further shown in FIG. 13, method 1300 may include sliding a distal resection guide over the two distal guide pins until the distal resection guide contacts the metatarsal, the distal resection guide having a metatarsal resection feature configure to guide resection of the metatarsal (block 1314). For example, a surgeon may slide a distal resection guide over the two distal guide pins until the distal resection guide contacts the metatarsal, the distal resection guide having a metatarsal resection feature configure to guide resection of the metatarsal, as described above.

As also shown in FIG. 13, method 1300 may include inserting a cutting tool into the metatarsal resection feature to create an osteotomy of the metatarsal (block 1316). For example, a surgeon may insert a cutting tool into the metatarsal resection feature to create an osteotomy of the metatarsal, as described above.

As further shown in FIG. 13, method 1300 may include sliding a positioning guide over the two proximal guide pins and the two distal guide pins until the positioning guide contacts the cuneiform and the metatarsal, where the positioning guide causes a cut face of the osteotomy of the cuneiform to contact a cut face of the osteotomy of the metatarsal (block 1318). For example, a surgeon may slide a positioning guide over the two proximal guide pins and the two distal guide pins until the positioning guide contacts the cuneiform and the metatarsal, where the positioning guide causes a cut face of the osteotomy of the cuneiform to contact a cut face of the osteotomy of the metatarsal, as described above.

As also shown in FIG. 13, method 1300 may include deploying fixation secured the cuneiform to the metatarsal (block 1320). For example, a surgeon may deploy fixation to secure the cuneiform to the metatarsal, as described above.

Method 1300 may include additional implementations, such as any single implementation or any combination of implementations described below and/or in connection with one or more other methods or processes described elsewhere herein. In a first implementation, the distal resection guide may include a first distal resection guide configured such that sliding the first distal resection guide further may include replacing the first distal resection guide with a second resection guide. The second resection guide may be configured to guide resection of the metatarsal at an angle that extends more distal from a proximal end of the metatarsal than the metatarsal resection feature of the first distal resection guide.

Although FIG. 13 shows example blocks or steps of a process 1300, in some implementations, A method 1300 may include additional steps, fewer steps, different steps, or differently arranged steps than those depicted in FIG. 13. Additionally, or alternatively, two or more of the steps of a method 1300 may be performed in parallel.

FIGS. 14A-14F illustrate different views of one or more stages in a surgical procedure that includes one or more embodiments of the present disclosure. Reference is made to FIGS. 8, 9A-D, 14A-14F and FIG. 13. In the illustrated embodiment, the metatarsal is a patient's first metatarsal 208.

Figures 14A, 14B, 14C, 14D, 14E, 14F:
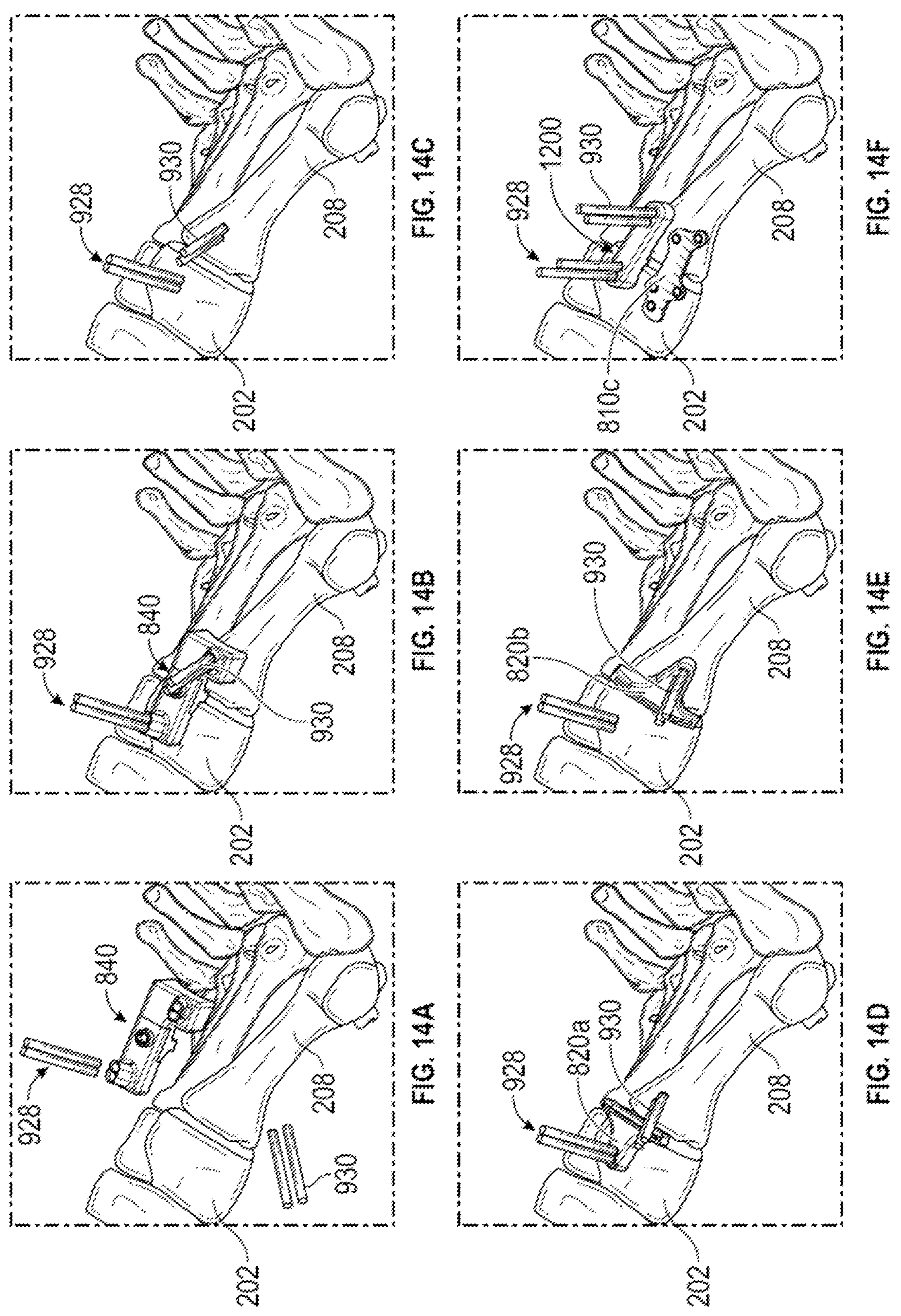
FIGS. 14A-14F illustrate different views of one or more stages in a surgical procedure that includes one or more embodiments of the present disclosure.

FIG. 14A illustrates a stage of the method 1300 in which a navigation guide (e.g., navigation guide 840, navigation guide 900, navigation guide 1000) is being deployed 1302 onto a TMT between a medial cuneiform 202 and a first metatarsal 208. In the illustrated embodiment, the surgeon has made an incision that permits placement of the navigation guide 840 on a first TMT of a patient. The set of proximal guide pins 928 and set of distal guide pins 930 are also illustrated and will be deployed shortly.

FIG. 14B illustrates a stage in the surgical procedure in which the navigation guide has been placed in a desired position across the TMT. Advantageously, a surgeon may leverage a bone engagement surface and/or bone engagement opening of the navigation guide to position the navigation guide where needed. Once the navigation guide is in place, a surgeon deploys 1304 a set of proximal guide pins 928 into a set of proximal holes 924 and a set of distal guide pins 930 into a set of distal holes 926. In this manner, markers of the navigation guide have been used to position the set of proximal guide pins 928 (a proximal reference feature on a medial cuneiform 202) and the set of distal guide pins 930 (a distal reference feature on a first metatarsal 208). In one embodiment, before deploying the set of proximal guide pins 928 and set of distal guide pins 930, a surgeon may use fluoroscopy to check the position of the navigation guide relative to the parts of the bone. Advantageously, at this stage the set of proximal guide pins 928 and the set of distal guide pins 930 are positioned for use in subsequent stages. Next, a surgeon may operate 1306 a coupler or severe a frangible portion of the navigation guide to separate the set of proximal guide pins 928 from the set of distal guide pins 930 and remove 1308 the navigation guide. In one embodiment, a surgeon may remove the bolt 962 to operate the coupler.

In one embodiment, FIG. 14C illustrates the TMT after method step 1308 is completed. The navigation guide has been removed. The set of proximal guide pins 928 are positioned in the medial cuneiform 202 and the set of distal guide pins 930 are positioned in the first metatarsal 208. The initial and accurate positioning of the set of proximal guide pins 928 and the set of distal guide pins 930 can be an important step in a surgical procedure because other steps and/or instruments may rely on accurate positioning of these pins to perform their respective desired functions and aspects. A surgeon can now proceed with the procedure with confidence that the reference features will provide accurate guidance that corresponds to the preplanned and desired correction, based on the medical imaging of the patient's foot.

In one embodiment, FIG. 14D illustrates a stage in which a proximal resection guide 820*a* has been slid 1310 over the set of proximal guide pins 928 until the proximal resection guide 820*a* contacts the medial cuneiform 202. The proximal resection guide 820*a* is securely in a desired location for an osteotomy of the medial cuneiform 202. Next a surgeon may operate the resection guide 800*a* by inserting 1312 a cutting tool such as a rectangular oscillating blade attached to a manual, mechanical, pneumatic, or electric driver into a resection feature to cut the medial cuneiform 202 for the osteotomy.

In one embodiment, FIG. 14E illustrates a stage in which a distal resection guide 820*b* has been slid 1314 over the set of distal guide pins 930 until the distal resection guide 820*b* contacts the first metatarsal 208. Those of skill in the art will appreciate that in certain embodiments prior to deploying the distal resection guide 820*b* a surgeon may remove the proximal resection guide 820*a*. The distal resection guide 820*b* is securely in a desired location for an osteotomy of the first metatarsal 208. Next a surgeon may operate the distal resection guide 820*b* by inserting 1316 a cutting tool such as a rectangular oscillating blade attached to a manual, mechanical, pneumatic, or electric driver into a resection feature to cut the first metatarsal 208 for the osteotomy.

Referring still to FIG. 14E, in certain embodiments, a surgeon may decide to change the corrective surgical procedure intraoperatively or for another reason decide to use a different distal resection guide 820*b* than the one originally planned. For example, suppose a surgeon wants to create an osteotomy of the first metatarsal 208 that is at a greater or lesser angle that that of the originally planned distal resection guide 820*b*. In such an instance, the proximal resection guide 820*a* may be referred to as a first distal resection guide 820*b* and a surgeon may replace the first distal resection guide 820*b* with a second distal resection guide 820*b* configured to guide resection of the first metatarsal 208 at a different angle than the first distal resection guide 820*b*. The second distal resection guide 820*b* may include a second metatarsal resection feature different from a metatarsal resection feature of the first distal resection guide 820*b*.

For example, the second distal resection guide 820*b* may be configured to guide resection of the first metatarsal 208 at an angle that extends more distal from a proximal end of the first metatarsal 208 than a metatarsal resection feature of the first distal resection guide 820*b*. In this manner, a surgeon has flexibility to change a preoperative plan as circumstances during the surgery indicate a need to do so, for example based on a condition and/or allowances of soft tissue of the patient.

In one embodiment, FIG. 14F illustrates a stage in which a positioning guide 1200 has been slid 1318 over the set of proximal guide pins 928 and the set of distal guide pins 930 until the positioning guide 1200 contacts the medial cuneiform 202 and the first metatarsal 208. This sliding action of the positioning guide 1200 causes unaligned guide pins to move into alignment which causes a cut face of the osteotomy of the cuneiform 202 to contact a cut face of the osteotomy of the metatarsal 208. FIG. 14F illustrates that deployment of the positioning guide 1200 has repositioned one or more of the medial cuneiform 202 and the first metatarsal 208 such that the bones are now reduced and in a state prepared for fixation. In certain embodiments, a surgeon may use flouroscopy to confirm the reduction. In certain embodiments, the deployment of the positioning guide 1200 may also apply compression for facilitating a union of the two bones. FIG. 14F also illustrates an example bone plate 810*c* that may be next be deployed 1320 to secure and/or connect the resected medial cuneiform 202 to the resected first metatarsal 208.

Those of skill in the art will appreciate that embodiments of the system disclosed herein can be used on humans and animals and on bones that are relatively small in comparison to other bones of the body (e.g., bones of the foot and hand). Advantageously, the embodiments of the system seek to minimize the number of fasteners or pins placed within the bones of a patient by planning a surgical procedure such that pins or fasteners placed in one stage are and/or can be reused in subsequent stages. Consequently, pins initially deployed can remain in the bone or bone fragment as instruments are deployed and/or subsequent stages of the surgical procedure are performed.

Advantageously, because the present disclosure uses a bone model of the patient's bones the sizes, dimensions, lengths and configurations of the components of the example systems can each be changed, adapted, revised, and/or customized to meet the needs and/or preferences of the patient and/or surgeon. Advantageously, using the apparatus, systems, and/or methods of the present disclosure the surgeon may have a preoperative plan that identifies which specific bone screw (length, width, diameter, thread, pitch, etc.) to use for the fasteners.

Advantageously, the present disclosure provides an apparatus, system, and/or method that can remediate a condition in a patient's foot. Those of skill in the art will appreciate that the methods, processes, apparatuses, systems, devices, and/or instruments of the present disclosure can be used to address a variety of conditions in a variety of procedures and/or parts of the body of the patient.

Conventionally, correction methods, systems, and/or instrumentation for a condition such as, for example, a bunion and/or a hallux valgus, face several challenges. One example is how to cut the bone such that the cut faces have a desired angle in relation to each other. Advantageously, the present disclosure can address many, if not all, of these challenges to assist a surgeon in performing the surgical procedure and improve the quality of patient care and outcomes.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the methods and systems of the present disclosure set forth herein without departing from it spirit and scope.

What is claimed is:

1. A system for remediating a condition present in a patient's foot, the system comprising:

a set of proximal guide pins;

a set of distal guide pins;

a navigation guide comprising:
a proximal end;
a distal end;
a body between the proximal end and the distal end, the body comprising:
a superior side, an inferior side, a medial side, a lateral side, a proximal side, and a distal side;
a set of proximal bone attachment features configured to identify a location for a proximal reference feature on a cuneiform of the patient's foot that corresponds to a proximal model reference on a cuneiform model of the cuneiform and to receive the set of proximal guide pins that define the proximal reference feature;
a set of distal bone attachment features configured to identify a location for a distal reference feature on a metatarsal of the patient's foot that corresponds to a distal model reference on a metatarsal model of the metatarsal and to receive the set of distal guide pins that define the distal reference feature;
wherein the set of proximal guide pins serve as a proximal resection guide anchor and as a proximal alignment feature and the set of distal guide pins serve as a distal resection guide anchor and as a distal alignment feature;
a registration key on the inferior side of the body, the registration key comprising a protrusion configured to engage both the cuneiform and the metatarsal of a foot joint;
a proximal resection guide configured to engage the set of proximal guide pins, the proximal resection guide comprising a cuneiform resection feature configured to guide resection of the cuneiform to form a cut face of the cuneiform for a correction of a condition present in a patient's foot;
a distal resection guide configured to engage the set of distal guide pins, the distal resection guide comprising a metatarsal resection feature configured to guide resection of the metatarsal to form a cut face of the metatarsal for the correction of the condition present in the patient's foot;
a positioning guide configured to engage the proximal alignment feature and the distal alignment feature as the positioning guide is deployed, the positioning guide configured to translate and rotate the metatarsal such that the cut face of the metatarsal contacts the cut face of the cuneiform; and
wherein the proximal alignment feature corresponds to the set of proximal guide pins used as the proximal resection guide anchor and the distal alignment feature corresponds to the set of distal guide pins used as the distal resection guide anchor.

2. The system of claim 1, wherein the navigation guide comprises a bone engagement surface configured to register to an anatomical structure of at least one of the cuneiform, the metatarsal, and the foot joint, the bone engagement surface defined based on medical imaging taken of the metatarsal and the cuneiform of the patient's foot.

3. The system of claim 1, wherein at least one of the navigation guide, the proximal resection guide, the distal resection guide, and the positioning guide comprises a bone engagement surface configured to register to an anatomical structure of the patient's foot.

4. The system of claim 1, wherein the navigation guide comprises a coupler between the proximal end and the distal end of the navigation guide, the coupler comprising:
a bolt comprising a head and a shaft, the head comprising a drive feature and the shaft comprising a set of threads on an external surface of the shaft;
a head opening in one of the proximal end and the distal end configured to receive the head of the bolt; and
a shaft opening in the other one of the proximal end and the distal end configured to receive the shaft of the bolt, the shaft opening comprising internal threads configured to engage the set of threads on the external surface of the shaft.

5. The system of claim 1, wherein the navigation guide comprises a plurality of sets of distal bone attachment features, each set of distal bone attachment features configured to be positioned radially about a long axis of the metatarsal at a different angle relative to the set of proximal bone attachment features.

6. The system of claim 5, wherein the different angles differ by about 5 degrees, +/−1 degree, relative to each other.

7. The system of claim 1, wherein the positioning guide comprises:
a positioning guide body comprising:
a set of proximal holes configured to accept and slide over the proximal alignment feature;
a set of distal holes configured to accept and slide over the distal alignment feature; and
wherein the set of proximal holes and the set of distal holes are configured such that translation of the positioning guide body along the proximal alignment feature and the distal alignment feature applies a compressive force to the metatarsal and the cuneiform to close an osteotomy formed in at least one of the metatarsal and the cuneiform.

8. The system of claim 7, wherein the set of proximal holes and the set of distal holes are positioned in the positioning guide body such that translating the positioning guide body along the proximal alignment feature and distal alignment feature causes the positioning guide body to apply a compressive force that compresses the cut face of the metatarsal against the cut face of the cuneiform.

9. A system for remediating a condition present in a patient's foot, the system comprising:
a set of proximal guide pins;
a set of distal guide pins;
a navigation guide comprising:
a proximal end;
a distal end;
a body between the proximal end and the distal end, the body comprising:
a superior side, an inferior side, a medial side, a lateral side, a proximal side, and a distal side;
a set of proximal bone attachment features configured to identify a location for a proximal reference feature on a cuneiform of the patient's foot that corresponds to a proximal model reference on a cuneiform model of the cuneiform and to receive the set of proximal guide pins that define the proximal reference feature;
a set of distal bone attachment features configured to identify a location for a distal reference feature on a metatarsal of the patient's foot that corresponds to a distal model reference on a metatarsal model of the metatarsal and to receive the set of distal guide pins that define the distal reference feature;
wherein the set of distal bone attachment features comprise a plurality of sets of distal bone attachment features, each set of distal bone attachment features configured to be positioned radially about a long axis of the metatarsal at a different angle relative to the set of proximal bone attachment features;

wherein the set of proximal guide pins serve as a proximal resection guide anchor and as a proximal alignment feature and the set of distal guide pins serve as a distal resection guide anchor and as a distal alignment feature;

a registration key on the inferior side of the body, the registration key comprising a protrusion configured to engage both the cuneiform and the metatarsal near a foot joint;

a proximal resection guide configured to engage the set of proximal guide pins, the proximal resection guide comprising a cuneiform resection feature configured to guide resection of the cuneiform to form a cut face of the cuneiform for a correction of a condition present in a patient's foot;

a distal resection guide configured to engage the set of distal guide pins, the distal resection guide comprising a metatarsal resection feature configured to guide resection of the metatarsal to form a cut face of the metatarsal for the correction of the condition present in the patient's foot; and a positioning guide configured to engage the proximal alignment feature and the distal alignment feature as the positioning guide is deployed, the positioning guide configured to translate and rotate the metatarsal such that the cut face of the metatarsal contacts the cut face of the cuneiform.

10. The system of claim 9, wherein the navigation guide comprises a bone engagement surface configured to register to an anatomical structure of at least one of the cuneiform, the metatarsal, and the foot joint, the bone engagement surface defined based on medical imaging taken of the metatarsal and the cuneiform of the patient's foot.

11. The system of claim 9, wherein at least one of the navigation guide, the proximal resection guide, the distal resection guide, and the positioning guide comprises a bone engagement surface configured to register to an anatomical structure of the patient's foot.

12. The system of claim 9, wherein the navigation guide comprises a coupler between the proximal end and the distal end of the navigation guide, the coupler comprising:

a bolt comprising a head and a shaft, the head comprising a drive feature and the shaft comprising a set of threads on an external surface of the shaft;

a head opening in one of the proximal end and the distal end configured to receive the head of the bolt; and a shaft opening in the other one of the proximal end and the distal end configured to receive the shaft of the bolt, the shaft opening comprising internal threads configured to engage the set of threads on the external surface of the shaft.

13. The system of claim 9, wherein the different angles for each member of the set of distal bone attachment features differ by about 5 degrees, +/−1 degree, relative to each other.

14. The system of claim 9, wherein the positioning guide comprises:

a positioning guide body comprising:

a set of proximal holes configured to accept and slide over the proximal alignment feature;

a set of distal holes configured to accept and slide over the distal alignment feature; and wherein the set of proximal holes and the set of distal holes are configured such that translation of the positioning guide body along the proximal alignment feature and the distal alignment feature applies a compressive force to the metatarsal and the cuneiform to close an osteotomy formed in at least one of the metatarsal and the cuneiform.

15. The system of claim 14, wherein the set of proximal holes and the set of distal holes are positioned in the positioning guide body such that translating the positioning guide body along the proximal alignment feature and distal alignment feature causes the positioning guide body to apply a compressive force that compresses the cut face of the metatarsal against the cut face of the cuneiform.

* * * * *